United States Patent
Tiebes et al.

(10) Patent No.: US 6,949,551 B2
(45) Date of Patent: Sep. 27, 2005

(54) DIHALOPROPENE COMPOUNDS, PROCESSES FOR THEIR PREPARATION, COMPOSITIONS COMPRISING THEM AND THEIR USE AS PESTICIDES

(75) Inventors: Jörg Tiebes, Frankfurt (DE); Ralf Braun, Ramberg (DE); Joachim Dickhaut, Heidelberg (DE); Harald Jakobi, Frankfurt (DE); Stephen Lindell, Kelkheim-Fischbach (DE); Vincent L. Salgado, Oberursel (DE); Eva Wojtech, Bad Soden/Ts. (DE); Daniela Jans, Bad Homburg v. d. H. (DE); Jutta Maria Waibel, Frankfurt (DE); Waltraud Hempel, Liederbach (DE); Ronald Wilhelm, Hofheim (DE)

(73) Assignee: Bayer Cropscience S.A., Lyons (FR)

( * ) Notice: Subject to any disclaimer, the term of this patent is extended or adjusted under 35 U.S.C. 154(b) by 124 days.

(21) Appl. No.: 10/289,398

(22) Filed: Nov. 7, 2002

(65) Prior Publication Data

US 2004/0029886 A1 Feb. 12, 2004

(30) Foreign Application Priority Data

Nov. 10, 2001 (DE) ......................................... 101 55 385

(51) Int. Cl.[7] ..................... C07C 43/225; C07C 205/34; C07D 239/34; A01N 43/54; A01N 43/40
(52) U.S. Cl. .................... 514/252.1; 514/269; 514/345; 514/406; 514/640; 514/721; 544/326; 544/408; 546/290; 548/366.1; 564/253; 568/661
(58) Field of Search .......................... 564/253; 546/265, 546/290; 514/277, 640, 252.1, 269, 345, 406, 721; 504/250, 244; 568/661; 544/326, 408; 548/366.1

(56) References Cited

FOREIGN PATENT DOCUMENTS

| EP | 0787710 B1 | 7/1999 |
|----|------------|--------|
| WO | 96/11909 A1 | 4/1996 |
| WO | 97/27173 A3 | 7/1997 |
| WO | 97/27173 A2 | 7/1997 |
| WO | 97/28112 A1 | 8/1997 |

Primary Examiner—Venkataraman Balasubramanian
(74) Attorney, Agent, or Firm—Burns, Doane, Swecker & Mathis, LLP

(57) ABSTRACT

Dihalopropene compounds, process for their preparation, compositions comprising them and their use as pesticides What is described are dihalopropene compounds of the formula (I)

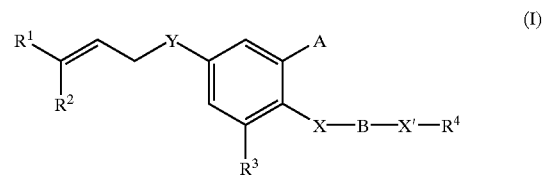

in which $R^1$ and $R^2$ are halogen, Y is —O—, —S— or —NH—, X is —O—, —S(O)$_r$— or —NR$^5$— (where r=0, 1, 2 and $R^5$ is hydrogen or $C_1$–$C_8$-alkyl), X' is a direct C—C bond, —O—, —S(O)$_r$— or —NR$^5$— (where $R^5$ is as defined above), $R^3$ is hydrogen, halogen, nitro, cyano, $C_1$–$C_8$-alkyl, $C_1$–$C_8$-haloalkyl, $C_1$–$C_8$-alkoxy, $C_1$–$C_8$-haloalkoxy, $C_3$–$C_{10}$-cycloalkyl or has one of the meanings defined for A, A has the meaning given in the description (inter alia aryl, heterocyclyl), B is a divalent bridge having the meanings given in the description (inter alia alkylene) and $R^4$ is a monovalent $C_6$–$C_{14}$-aryl radical or nitrogen-containing heteroaryl radical having at least one ring heteroatom which has the meanings given in the description.

These compounds can be used for preparing pesticides.

35 Claims, No Drawings

DIHALOPROPENE COMPOUNDS, PROCESSES FOR THEIR PREPARATION, COMPOSITIONS COMPRISING THEM AND THEIR USE AS PESTICIDES

The invention relates to dihalopropene compounds, to a process for their preparation, to compositions comprising them and to their use for controlling animal pests, in particular arthropods, such as insects and acarids, and helminthes.

Owing to the enormous damage caused by insects, for example by feeding on useful plants, stored food, wood and textiles, or else by transferring diseases to man, domestic animals and useful plants, the use of insecticides or repellents remains indispensable. Insecticides are an important component of integrated pest control, and their contribution is decisive with respect to harvest yields and yield continuity all over the world.

The insecticidal and/or acaricidal action of compounds from the class of the dihalopropene compounds is known per se.

Compounds from this class of substances and their insecticidal and/or acaricidal action are described in EP-A-787,710, WO-A-96/11,909, WO-A-97/27,173 and WO-A-97/28,112.

However, since the ecological and economic demands made on modern insecticides are increasing continually, for example with respect to toxicity, selectivity, application rates, formation of residues and favorable manufacture, and there can furthermore be problems, for example with resistance, there is a constant need to develop novel insecticides which, at least in some areas, have advantages over those of the prior art.

It has been found that compounds of the formula (I) have a good activity spectrum against animal pests and at the same time good compatibility with plants and favorable toxicological properties with respect to mammals and aquatic animals.

Accordingly, the invention provides compounds of the formula (I)

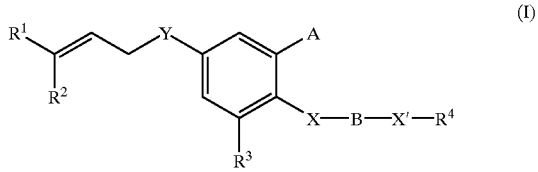

(I)

in which $R^1$ and $R^2$ independently of one another are halogen,

Y is —O—, —S— or —NH—,

X is —O—, —S(O)$_r$— or —NR$^5$—, where r=0, 1 or 2 and $R^5$ is hydrogen or $C_1$–$C_8$-alkyl, X' is a direct C—C bond, —O—, —S(O)$_r$— or —NR$^5$—, where r and $R^5$ are as defined above, $R^3$ is hydrogen, halogen, nitro, cyano, $C_1$–$C_8$-alkyl, $C_1$–$C_8$-haloalkyl, $C_1$–$C_8$-alkoxy, $C_1$–$C_8$-haloalkoxy or $C_3$–$C_{10}$-cycloalkyl or has one of the meanings defined for A, A is one of the groups —OR$^6$, —SR$^6$, —NR$^7$R$^8$, —S(=O) $R^6$, —S(=O)$_2$R$^6$, —C(=Z)-R$^6$, —C(=Z)-OR$^6$, —C(=Z)-SR$^6$, —C(=Z)-NR$^7$R$^8$, —C(=Z)-O—N=C(NH$_2$)—R$^6$, —O—C(=Z)-R$^6$, —O—C(=Z)-OR$^6$, —O—C(=Z)-SR$^6$, —O—C(=Z)-NR$^7$R$^8$, —S—C(=Z)-R$^6$, —S—C(=Z)-OR$^6$, —S—C(=Z)-SR$^6$, —S—C(=Z)-NR$^7$R$^8$, —NR$^9$—C (=Z)-R$^6$, —NR$^9$—C(=Z)-OR$^6$, —NR$^9$—C(=)-SR$^6$ or —NR$^9$—C(=Z)-NR$^7$R$^8$, or A is $C_2$–$C_8$-alkenyl which is unsubstituted or substituted by one or more radicals, these radicals being halogen, cyano, nitro, hydroxyl, $C_1$–$C_8$-alkyl, $C_1$–$C_8$-haloalkyl, $C_1$–$C_8$-alkoxy, $C_1$–$C_8$-haloalkoxy, tri-($C_1$–$C_8$-alkyl)silyl, aryl-($C_1$–$C_8$)-dialkylsilyl, diaryl-($C_1$–$C_8$)-alkylsilyl, triarylsilyl, —COOR$^6$, —CO—NR$^7$R$^8$, $C_6$–$C_{14}$-aryl and/or heteroaryl having one to three ring heteroatoms, where these radicals for their part may be substituted by one or more radicals selected from the group consisting of halogen, cyano, nitro, hydroxyl, $C_1$–$C_8$-alkyl, $C_1$–$C_8$-haloalkyl, $C_1$–$C_8$-alkoxy and $C_1$–$C_8$-haloalkoxy; or A is $C_2$–$C_8$-alkynyl which is unsubstituted or substituted by one or more radicals, these radicals being halogen, cyano, nitro, hydroxyl, $C_1$–$C_8$-alkyl, $C_1$–$C_8$-haloalkyl, $C_1$–$C_8$-alkoxy, $C_1$–$C_8$-haloalkoxy, tri-($C_1$–$C_8$-alkyl)silyl aryl-($C_1$–$C_8$)-dialkylsilyl, diaryl-($C_1$–$C_8$)-alkylsilyl, triarylsilyl, —COOR$^6$, —CO—NR$^7$R$^8$, $C_6$–$C_{14}$-aryl and/or heteroaryl having one to three ring heteroatoms, where these radicals for their part may be substituted by one or more radicals selected from the group consisting of halogen, cyano, nitro, hydroxyl, $C_1$–$C_8$-alkyl, $C_1$–$C_8$-haloalkyl, $C_1$–$C_8$-alkoxy and $C_1$–$C_8$-haloalkoxy; or A is $C_6$–$C_{14}$-aryl which is unsubstituted or substituted by one or more radicals, these radicals being halogen, cyano, hydroxyl, nitro, $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_2$–$C_8$-alkenyl, $C_2$–$C_8$-haloalkenyl, $C_2$–$C_8$-alkynyl, $C_2$–$C_8$-haloalkynyl, $C_2$–$C_8$-alkyloxyalkylene, $C_2$–$C_8$-alkyl-thioalkylene, $C_3$–$C_8$-alkanoyloxyalkylene, $C_1$–$C_8$-aminoalkylene, phenyloxyalkylene, phenylthioalkylene, $C_3$–$C_8$-cycloalkyl, $C_6$–$C_{14}$-aryl, heteroaryl having one to three ring heteroatoms, —COOR$^6$, —CO—NR$^7$R$^8$ and/or —S(O)$_r$—R$^3$, where r and $R^3$ are as defined above, where the aryl and/or the heteroaryl radicals for their part may be substituted by one or more radicals selected from the group consisting of halogen, cyano, nitro, hydroxyl, $C_1$–$C_8$-alkyl, $C_1$–$C_8$-haloalkyl, $C_1$–$C_8$-alkoxy and $C_1$–$C_8$-haloalkoxy; or A is a heterocyclic radical having one to three ring heteroatoms and preferably two to eight ring carbon atoms which is unsubstituted or substituted by one or more radicals, these radicals being halogen, cyano, hydroxyl, nitro, $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_2$–$C_8$-alkenyl, $C_2$–$C_8$-haloalkenyl, $C_2$–$C_8$-alkynyl, $C_2$–$C_8$-haloalkynyl, $C_2$–$C_8$-alkyloxyalkylene, $C_2$–$C_8$-alkylthioalkylene, $C_3$–$C_8$-alkanoyloxyalkylene, $C_1$–$C_8$-aminoalkylene, phenyloxyalkylene, phenylthioalkylene, $C_3$–$C_8$-cycloalkyl, $C_6$–$C_{14}$-aryl, heteroaryl having one to three ring heteroatoms, —COOR$^6$, —CO—NR$^7$R$^8$ and/or —S(O)$_r$—R$^3$, where r and $R^3$ are as defined above, where the aryl and/or the heteroaryl radicals for their part may be substituted by one or more radicals selected from the group consisting of halogen, cyano, nitro, hydroxyl, $C_1$–$C_8$-alkyl, $C_1$–$C_8$-haloalkyl, $C_1$–$C_8$-alkoxy and $C_1$–$C_8$-haloalkoxy; or A is $C_1$–$C_8$-alkyl which is substituted by one to six groups, its substituents being selected from the group consisting of hydroxyl, amino, N—($C_1$–$C_8$-alkyl)amino, N,N-bis-($C_1$–$C_8$-alkyl)amino, $C_1$–$C_8$-alkoxy, $C_1$–$C_8$-haloalkoxy, $C_1$–$C_8$-acyloxy and $C_1$–$C_8$-haloacyloxy, or where two substituents together may also form an alkylene chain which may contain one or more oxygen, nitrogen and/or sulfur atoms, for example an acetal, lactone or lactam ring system, Z is =O, =S, =N—R$^{33}$, =N—O—R$^{33}$ or =N—NR$^{33}$R$^{34}$, $R^6$, $R^7$, $R^8$, $R^9$, $R^{33}$ and $R^{34}$ independently of one another are hydrogen, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl, $C_4$–$C_{10}$-cycloalkynyl, $C_6$–$C_{14}$-aryl or heteroaryl having one to three ring heteroatoms which for their part may be substituted by halogen, hydroxyl, cyano, nitro, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl, $C_4$–$C_{10}$-cycloalkynyl, $C_6$–$C_{14}$-aryl, halogen-substituted $C_6$–$C_{14}$-aryl, heteroaryl having one to three ring heteroatoms or halogen-substituted heteroaryl having one to three ring heteroatoms, amino, N—($C_1$–$C_8$-alkyl)amino, N,N-bis-($C_1$–$C_8$-alkyl)amino, tri-($C_1$–$C_8$-alkyl)silyl, aryl-($C_1$–$C_8$)-dialkylsilyl, diaryl-($C_1$–$C_8$)-alkylsilyl, triarylsilyl, $C_1$–$C_8$-alkoxy and/or $C_1$–$C_8$-haloalkoxy, B is a divalent bridge and is alkylene having one to twelve carbon atoms, cycloalkylene having three to fourteen carbon atoms, alkylene-cycloalkylene having four to twenty-six carbon atoms, alkylene-cycloalkylene-alkylene having five to thirty-eight carbon atoms, where these bridges may have one to three ethylenically unsaturated bonds and/or may be interrupted by —O—, —S—, —C(=O)O— or —NR$^5$— groups, where R$^5$ is as defined above and where the bridge may be unsubstituted or substituted by one to ten substituents selected from the group consisting of $C_1$–$C_3$-alkyl, trifluoromethyl and trichloromethyl, and $R^4$ is a monovalent $C_6$–$C_{14}$-aryl radical or nitrogen-containing heteroaryl radical having at least one, preferably one to three, ring heteroatom which is unsubstituted or substituted by one to four radicals selected from the group consisting of halogen, cyano, nitro, thiocyanato, isocyanato, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl, $C_4$–$C_{10}$-cycloalkynyl, $C_6$–$C_{14}$-aryl, nitrogen-containing heteroaryl having one to three ring heteroatoms, where these substituents for their part may be substituted by radicals selected from the group consisting of halogen, cyano, nitro, $C_1$–$C_8$-alkyl, $C_1$–$C_8$-haloalkyl, $C_1$–$C_8$-alkoxy, $C_1$–$C_8$-haloalkoxy, —C(=Z)-R$^6$, —C(=Z)-OR$^6$, —C(=Z)-SR$^6$, —C(=Z)-NR$^7$R$^8$, —C(=Z)-O—N=C(NH$_2$)—R$^6$, —O—C(=Z)-R$^6$, —O—C(=Z)-OR$^6$, —O—C(=Z)-SR$^6$, —O—C(=Z)-NR$^7$R$^8$, —S—C(=Z)-R$^6$, —S—C(=Z)-OR$^6$, —S—C(=Z)-SR$^6$, —S—C(=Z)-NR$^7$R$^8$, —NR$^9$—C(=Z)-R$^6$, —NR$^9$—C(=Z)-OR$^6$, —NR$^9$—C(=Z)-SR$^6$, —NR$^9$—C(=Z)-NR$^7$R$^8$, —OR$^6$, —SR$^6$, —S(=O)R$^6$, —S(=O)$_2$R$^6$, NR$^7$R$^8$, where Z, R$^6$, R$^7$, R$^8$ and R$^9$ are as defined above.

The term "halogen" includes fluorine, chlorine, bromine and/or iodine. Preferred are fluorine, chlorine and/or bromine.

The term "($C_1$–$C_8$)-alkyl" is to be understood as meaning an unbranched or branched aliphatic and saturated hydrocarbon radical having one to eight carbon atoms, such as, for example, the methyl, ethyl, propyl, isopropyl, 1-butyl, 2-butyl, isobutyl, tert-butyl, n-pentyl, 2-methylbutyl, 1,1-dimethylpropyl, n-hexyl, n-heptyl, n-octyl or 2-ethylhexyl radical. Preference is given to methyl.

"($C_1$–$C_8$)-haloalkyl" is to be understood as meaning an alkyl group mentioned under the term "($C_1$–$C_8$)-alkyl" in which one or more hydrogen atoms are replaced by the same number of identical or different halogen atoms, preferably by chlorine or fluorine, such as the trifluoromethyl, the 1- or 2-fluoroethyl, the 2,2,2-trifluoroethyl, the chloromethyl, the fluoromethyl, the difluoromethyl or the 1,1,2,2-tetrafluoroethyl group.

"($C_1$–$C_8$)-alkoxy" is to be understood as meaning alkoxy groups whose hydrocarbon radicals have the meanings given under the terms "($C_1$–$C_8$)-alkyl".

"($C_1$–$C_8$)-haloalkoxy" is to be understood as meaning an alkoxy group mentioned under the term "($C_1$–$C_8$)-alkoxy" in which one or more hydrogen atoms are replaced by the same number of identical or different halogen atoms, preferably by chlorine or fluorine, such as the trifluoromethyloxy, the 1- or 2-fluoroethyloxy, the 2,2,2-tri-fluoroethyloxy, the chloromethyloxy, the fluoromethyloxy, the difluoromethyloxy or the 1,1,2,2-tetrafluoroethyloxy group.

"($C_1$–$C_8$)-alkylthio" is to be understood as meaning alkylthio groups whose hydrocarbon radicals have the meanings given under the terms "($C_1$–$C_8$)-alkyl".

"($C_1$–$C_8$)-haloalkylthio" is to be understood as meaning an alkylthio group mentioned under the term "($C_1$–$C_8$)-alkylthio" in which one or more hydrogen atoms are replaced by the same number of identical or different halogen atoms, preferably by chlorine or fluorine, such as the trifluoromethylthio, the 1- or 2-fluoroethylthio, the 2,2,2-trifluoroethylthio, the chloromethylthio, the fluoromethylthio, the difluoromethylthio or the 1,1,2,2-tetrafluoroethylthio group.

"($C_3$–$C_{10}$)-cycloalkyl" is to be understood as meaning monocyclic and saturated alkyl radicals having three to ten ring carbon atoms. Examples are cyclopropyl, cyclobutyl, cyclopentyl, cyclohexyl, cycloheptyl or cyclooctyl. The term furthermore comprises bicyclic and saturated alkyl radicals, such as the norbornyl or bicyclo[2.2.2]octyl radical, or else fused and saturated systems, such as, for example, the decahydronaphthyl radical.

The term "tri-($C_1$–$C_8$-alkyl)silyl" denotes a silicon atom which carries three identical or different alkyl radicals according to the above definition. Analogously, "aryl-($C_1$–$C_8$)-dialkylsilyl" denotes a silicon atom which carries an aryl radical and two identical or different alkyl radicals according to the above definition, "diaryl-($C_1$–$C_8$)-alkylsilyl" denotes a silicon atom which carries one alkyl radical and two identical or different aryl radicals according to the above definition, and "triarylsilyl" denotes a silicon atom which carries three identical or different aryl radicals according to the above definition.

Examples of radicals —COOR$^6$ are the carboxyl groups or esters thereof with mono-valent aliphatic, cycloaliphatic, aromatic or heterocyclic alcohols according to the definitions given above for R$^6$. Preferred are the carboxyl group, the methyl, ethyl or propyl esters, the cyclohexyl esters and the phenyl esters, where in the aliphatic, cycloaliphatic, aromatic or heterocyclic radicals one or more hydrogen atoms may be replaced by halogen, in particular by fluorine or chlorine. One example is the trifluoromethyl group.

Examples of radicals —CO—NR$^7$R$^8$ are the carboxamide groups whose nitrogen atom may be mono- or disubstituted by monovalent aliphatic, cycloaliphatic, aromatic or heterocyclic radicals according to the definitions given above for R$^7$ and R$^8$. Preference is given to the carboxamide group, the N-methyl-, N-ethyl- or N-propyl-carboxamide group and to the corresponding disubstituted derivatives, such as the N,N-dimethyl-, N,N-diethyl- or N,N-dipropylcarboxamide group and the corresponding asymmetrically substituted groups, where in the aliphatic, cycloaliphatic, aromatic or heterocyclic radicals one or two hydrogen atoms may be replaced by halogen, in particular by fluorine or chlorine. One example is the trifluoromethyl group.

The term "($C_6$–$C_{14}$)-aryl" is to be understood as meaning a carbocyclic, i.e. constructed of carbon atoms, aromatic radical having 6 to 14, in particular 6 to 12, ring carbon atoms. Examples are monocyclic aromatic radicals, such as phenyl, polycyclic fused aromatic radicals, such as naphthyl or anthracyl, or polycyclic aromatic radicals which are attached via C—C bonds or bridges such as —O— or —S—, such as biphenylyl. Preference is given to phenyl.

The term "heterocyclic radical having one to three ring heteroatoms" denotes a cyclic radical which may be completely saturated, partially unsaturated or fully unsaturated or aromatic and which is interrupted by at least one to three identical or different heteroatoms, preferably from the group consisting of nitrogen, sulfur and oxygen, where, however, two oxygen atoms may not be directly adjacent and at least one carbon atom has to be present in the ring. Preferred are radicals having four, five, six or seven ring atoms, in particular five or six ring atoms.

The terms "$C_2$–$C_8$-alkenyl" or "$C_3$–$C_8$-alkenyl" and "$C_2$–$C_8$-alkynyl" or "$C_3$–$C_8$-alkynyl" denote a straight-chain or branched hydrocarbon radical having two to eight and three to eight carbon atoms, respectively, which hydrocarbon radical contains at least one multiple bond which may be located in any position of the unsaturated radical in question.

Accordingly, "($C_2$–$C_8$)-alkenyl" denotes, for example, the vinyl, allyl, 2-methylpropenyl, 1- or 2-butenyl, pentenyl, 2-methylpentenyl, hexenyl, heptenyl or octenyl group.

Accordingly, "($C_2$–$C_8$)-alkynyl" denotes, for example, the ethynyl, propargyl, 2-methylpropynyl, 2-butynyl, pentynyl, 2-methylpentynyl, hexynyl, heptynyl or octynyl group.

"($C_2$–$C_8$)-haloalkenyl" and "($C_2$–$C_8$)-haloalkynyl" are to be understood as meaning alkenyl and alkynyl groups, respectively, mentioned under the terms "($C_2$–$C_8$)-alkenyl" and "($C_2$–$C_8$)-alkynyl", respectively, in which one or more hydrogen atoms are replaced by the same number of identical or different halogen atoms, preferably by chlorine or fluorine, such as the 1- or 2-fluoroethenyl or -ethynyl group or the 1- or 2-chloroethenyl or -ethynyl group.

"$C_2$–$C_8$-alkyloxyalkylene" is to be understood as meaning alkyl radicals having two to eight carbon atoms and containing one or more oxygen atoms in the alkyl chain. Examples are methoxymethylene, methoxyethylene, methoxypropylene, methoxybutylene, ethoxymethylene, ethoxyethylene, ethoxypropylene and ethoxybutylene.

"$C_2$–$C_8$-alkylthioalkylene" is to be understood as meaning alkyl radicals having two to eight carbon atoms and containing one or more sulfur atoms in the alkyl chain. Examples are methylthiomethylene, methylthioethylene, methylthiopropylene, methylthiobutylene, ethylthiomethylene, ethylthioethylene, ethylthiopropylene and ethylthiobutylene.

"$C_3$–$C_8$-alkanoyloxyalkylene" is to be understood as meaning alkyl radicals having three to eight carbon atoms and containing one or more carbonyloxy groups, preferably one carbonyloxy group, in the alkyl chain. Examples are methanoyloxymethylene, methanoyloxyethylene, methanoyloxypropylene, methanoyloxybutylene, ethanoyloxymethylene, ethanoyloxyethylene, ethanoyloxypropylene and ethanoyloxybutylene.

"$C_1$–$C_8$-aminoalkylene" is to be understood as meaning alkyl radicals having one to eight carbon atoms and containing one or more amino groups in the alkyl chain or as substituents on the alkyl chain. The amino groups for their part may be mono- or dialkylsubstituted. The amino groups may be terminal or located within the chain. Examples are aminomethylene, 2-aminoethylene, 3-aminopropylene, 4-aminobutylene, methylaminomethylene, 2-methylaminoethylene, 3-methylaminopropylene and 4-methylaminobutylene.

"Phenyloxyalkylene" is to be understood as meaning alkyl radicals substituted by one or more phenyloxy groups. One example is phenyloxymethylene.

"Phenylthioalkylene" is to be understood as meaning alkyl radicals substituted by one or more phenylthio groups. One example is phenylthiomethylene.

The term "$C_1$–$C_8$-alkyl substituted by one to six groups" denotes a $C_1$–$C_8$-alkyl radical in which one to six hydrogen atoms are substituted by hydroxyl groups, by unsubstituted amino groups, by amino groups which are substituted on the nitrogen by one or two $C_1$–$C_8$-alkyl groups, by $C_1$–$C_8$-alkoxy groups, by $C_1$–$C_8$-haloalkoxy groups, by $C_1$–$C_8$-acyloxy groups, by $C_1$–$C_8$-haloacyloxy groups or by combinations of these groups.

Here, the terms "$C_1$–$C_8$-alkyl groups", "$C_1$–$C_8$-alkoxy groups" and "$C_1$–$C_8$-haloalkoxy groups" are as defined above.

"$C_1$–$C_8$-acyloxy groups" is to be understood as meaning monovalent radicals of saturated carboxylic acids having one to eight carbon atoms. Examples are the formyl, acetyl, propionyl, butyryl, 2-methylbutyryl, pivaloyl or octanoyl groups.

"$C_1$–$C_8$-haloacyloxy groups" is to be understood as meaning monovalent radicals of saturated carboxylic acids having one to eight carbon atoms in which one or more hydrogen atoms are substituted by halogen atoms. Examples are the chloroformyl, monochloroacetyl, dichloroacetyl, trichloroacetyl, monochloropropionyl, dichloropropionyl, trichloropropionyl, tetrachloropropionyl, pentachloropropionyl, monochlorobutyryl, dichlorobutyryl, trichlorobutyryl, tetrachlorobutyryl, pentachlorobutyryl, hexachlorobutyryl and heptachlorobutyryl groups and the corresponding brominated derivatives and brominated and chlorinated derivatives.

"($C_4$–$C_{10}$)-cycloalkenyl" is to be understood as meaning monocyclic alkyl radicals which contain at least one multiple bond and four to ten ring carbon atoms. Examples are cyclobutenyl, cyclopentenyl, cyclohexenyl, cycloheptenyl, cyclooctenyl and cyclodecenyl. These radicals furthermore include bicyclic alkyl radicals which contain at least one multiple bond, such as the norbornenyl or bicyclo[2.2.2] octenyl radical, or else fused systems which contain at least one multiple bond, such as, for example, the tetra-, hexa- or octahydronaphthyl radical.

"($C_4$–$C_{10}$)-cycloalkynyl" denotes, for example, the cyclooctynyl, cyclononynyl or cyclodecynyl radical.

The term "divalent bridge" is to be understood as meaning divalent alkylene radicals having one to twelve carbon atoms, divalent cycloalkylene radicals having three to fourteen carbon atoms, and combinations thereof, such as alkylene-cycloalkylene having four to twenty-six carbon atoms, alkylene-cycloalkylene-alkylene having five to thirty-eight carbon atoms. These alkylene and/or cycloalkylene radicals may have one to three ethylenically unsaturated bonds, and/or they can be interrupted by one or more oxygen atoms, sulfur atoms, nitrogen atoms or groups containing oxygen atoms. The alkylene radicals can be straight-chain or branched.

These alkylene and/or cycloalkylene radicals may furthermore have one to ten substituents. These substituents are $C_1$–$C_3$-alkyl groups and/or trichloromethyl and/or trifluoromethyl. Examples of $C_1$–$C_3$-alkyl groups are methyl, ethyl, n-propyl and isopropyl. Preference is given to methyl, trichloromethyl and trifluoromethyl.

The term "nitrogen-containing heteroaryl radical having at least one, preferably one to three, ring heteroatoms" denotes a heteroaromatic radical which may be interrupted by at least one or a plurality of identical or different heteroatoms, in particular atoms selected from the group consisting of nitrogen, sulfur and oxygen, where at least one heteroatom has to be a nitrogen atom, but where two oxygen atoms may not be directly adjacent and where at least one carbon atom has to be present in the ring. These are preferably radicals having five or six ring atoms, of which one, two or three are nitrogen atoms.

Preference is given to compounds of the formula I in which $R^1$ and $R^2$ are each chlorine or bromine.

Preference is also given to compounds of the formula I in which Y is —O—.

Very particular preference is given to compounds of the formula I in which $R^1$ and $R^2$ are each chlorine and Y is —O—.

Preference is furthermore given to compounds of the formula I in which X is —O—, —S— or —NH— and X' is a direct C—C bond, —O—, —S— or —NH—, in particular to compounds of the formula I in which X and X' are each —O— or X is —O— and X' is a direct C—C bond.

Preference is given to compounds of the formula I in which $R^3$ is hydrogen, fluorine, chlorine, bromine, methyl, trifluoromethyl, monochloromethyl, dichloromethyl, trichloromethyl, methoxy, trifluoromethoxy, monochloromethoxy, dichloromethoxy, trichloromethoxy, nitro, cyano, cyclohexyl, phenyl or a monovalent radical derived from thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine, piperidine, pyrrolidine, oxazoline, tetrahydrofuran, tetrahydropyran, isoxazolidine or thiazolidine.

Very particular preference is given to compounds of the formula I in which $R^3$ is methyl, trifluoromethyl, cyano, chlorine or bromine.

Preference is given to compounds of the formula I in which Z is =O, =N—OH, =N—OCH$_3$ or =N—CH$_2$—CH=CH$_2$.

Particularly preferred radicals A are the groups —C(=O)—CH$_3$, —C(=N—OCH$_3$)—CH$_3$, —C(=N—OH)—CH$_3$, —C(=O)—OCH$_3$, —C(=O)—CH=CH—N(CH$_3$)$_2$, —C(=O)—NH—C$_2$H$_5$, —C(=O)—NH$_2$, —C(=O)—N(CH$_3$)$_2$, —C(=O)—NH—CH$_2$—CH$_2$—OH, —C(=O)—NH—CH(CH$_3$)—CH$_2$—OH, —C(=O)—CHBr$_2$, —C(=O)—N(CH$_3$)—O—CH$_3$, —C(=N—O—CH$_2$—CH=CH$_2$)—CH$_3$, —C(=S)—NH$_2$, —C(=O)—O—C$_6$H$_5$, —C(=O)—O—C$_3$H$_7$, —C(=O)-imidazolyl, —C(=O)-3-ethyl-1,2,4-oxadiazol-5-yl, —C(=O)-2Δ-oxazolin-2-yl, —C(=O)-1-methylpyrazol-3-yl, —C(=O)-ethyn-2-yl, —C(=O)-1-hydroxyethyn-2-yl, —C(=O)-1-trimethylsilylethyn-2-yl, —C(=O)-1-hexylethyn-2-yl, —C(=O)-1-(2-chlorophenyl)ethyn-2-yl, —C(=O)-1-methoxyethyn-2-yl and —C(=O)-ethen-2-yl.

Preference is given to compounds of the formula I in which A is C$_2$–C$_8$-alkenyl, C$_2$–C$_8$-alkynyl, phenyl, pyridyl or pyrimidyl which are unsubstituted or substituted by one or more halogen atoms, cyano groups, nitro groups, hydroxyl groups, C$_1$–C$_3$-alkoxy radicals or C$_1$–C$_3$-haloalkoxy radicals, C$_1$–C$_3$-alkoxy radicals, C$_1$–C$_3$-haloalkoxy radicals which for their part are unsubstituted or substituted by one or more halogen atoms, cyano groups, nitro groups, hydroxyl groups, C$_1$–C$_3$-alkoxy radicals or C$_1$–C$_3$ haloalkoxy radicals, or is —OR$^6$, —SR$^6$, —NR$^7$R$^8$, —S(=O)R$^6$, —S(=O)$_2$R$^6$, —C(=Z)-R$^6$, —C(=Z)-OR$^6$, —C(=Z)-SR$^6$, —C(=Z)-NR$^7$R$^8$, —O—C(=Z)-R$^6$, —O—C(=)-OR$^6$, —O—C(=)-SR$^6$, —O—C(=Z)-NR$^7$R$^8$, —S—C(=Z)-R$^6$, —S—C(=Z)-OR$^6$, —S—C(=Z)-SR$^6$, —S—C(=Z)-NR$^7$R$^8$, —NR$^9$—C(=Z)-R$^6$, —NR$^9$—C(=Z)-OR$^6$, —NR$^9$—C(=Z)-SR$^6$ or —NR$^9$—C(=Z)-NR$^7$R$^8$, where Z, R$^6$, R$^7$, R$^8$ and R$^9$ are as defined in Claim 1, or is C$_1$–C$_8$-alkyl which is substituted by one or more hydroxyl groups, C$_1$–C$_3$-alkoxy radicals, C$_1$–C$_3$-haloalkoxy radicals, C$_1$–C$_3$-acyloxy radicals or C$_1$–C$_3$-haloacyloxy radicals, or is a group of the formulae Q$^1$–Q$^{10}$

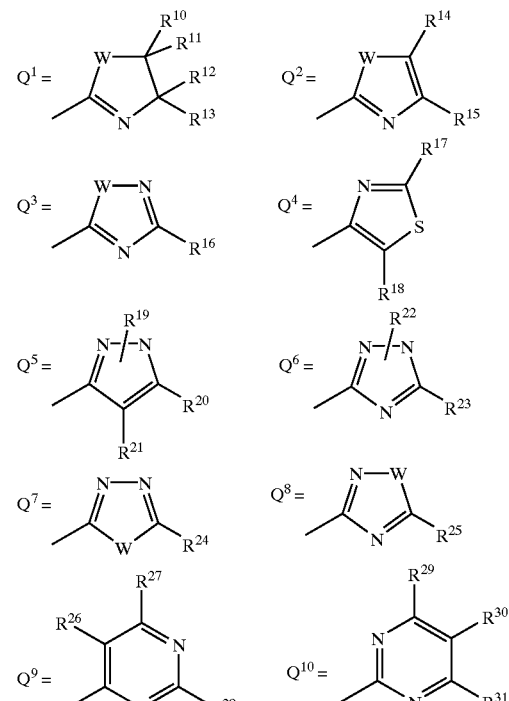

in which W is oxygen or sulfur, R$^{10}$ to R$^{18}$, R$^{20}$ and R$^{21}$, R$^{23}$ to R$^{31}$ are hydrogen, C$_1$–C$_6$-alkyl, C$_3$–C$_7$-cycloalkyl, C$_2$–C$_6$-alkenyl, C$_4$–C$_7$-cycloalkenyl, pyridyl or phenyl, where the C$_1$–C$_6$-alkyl, C$_3$–C$_7$-cycloalkyl, C$_2$–C$_6$-alkenyl and C$_4$–C$_7$-cycloalkenyl radicals are unsubstituted or mono- or polysubstituted, preferably mono-, di- or trisubstituted by halogen, cyano, —OR$^6$, —SR$^6$, —S(O)R$^6$, —S(O)$_2$R$^6$ and/or —NR$^7$R$^8$, where the radicals R$^6$, R$^7$ and R$^8$ are as defined above, and where phenyl and pyridyl are unsubstituted or mono- or polysubstituted, preferably mono-, di- or trisubstituted by halogen, cyano, nitro, —OR$^6$, —SR$^6$, —S(O)R$^6$, —S(O)$_2$R$^6$, —NR$^7$R$^8$, C$_1$–C$_4$-alkyl, C$_1$–C$_4$-haloalkyl, C$_2$–C$_4$-alkenyl and/or C$_2$–C$_4$-haloalkyl.

Preference is given to compounds of the formula I in which B is a group of the formulae P$^1$ to P$^6$ $P^1 = -C(R^{32})_2-$ $P^2 = -[C(R^{32})_2]_i-Y'-[C(R^{32})_2]_j-$

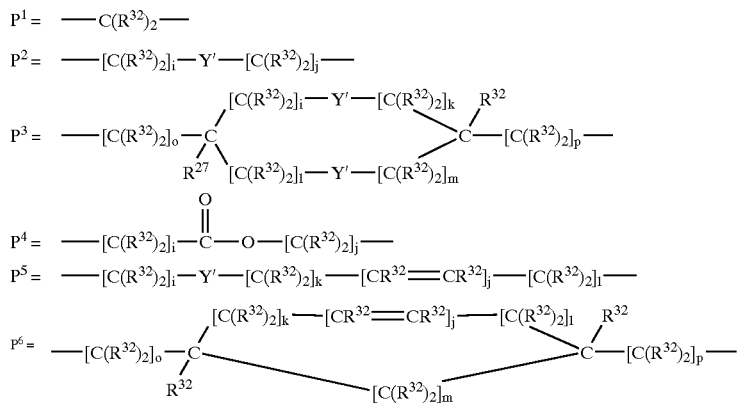

$P^4 = -[C(R^{32})_2]_i-\overset{\overset{O}{\|}}{C}-O-[C(R^{32})_2]_j-$ $P^5 = -[C(R^{32})_2]_i-Y'-[C(R^{32})_2]_k-[CR^{32}=CR^{32}]_j-[C(R^{32})_2]_l-$ in which $R^{32}$ in each case independently of the others is hydrogen, $C_1$–$C_3$-alkyl or trifluoromethyl, Y' in each case independently of the others is a direct C—C bond, —O—, —S— or —NH—, i is an integer from 1 to 6,
j is an integer from 1 to 6,
k is an integer from 0 to 2,
l is an integer from 0 to 2,
m is an integer from 0 to 2,
o is an integer from 0 to 1 and
p is an integer from 0 to 1.

Very particular preference is given to compounds of the formula I in which B is a group of the formula —$C_qH_{2q}$— and q is an integer from 2 to 4, in particular —$(CH_2)_2$—, —$(CH_2)_3$— and —$(CH_2)_4$—.

Preference is furthermore given to compounds of the formula I in which $R^4$ is $C_6$–$C_{14}$-aryl which is unsubstituted or substituted by one or more, preferably by one to three radicals selected from the group consisting of halogen, cyano, nitro, thiocyanato, isocyanato, $C_1$–$C_6$-alkyl, $C_3$–$C_8$-cycloalkyl, $C_2$–$C_8$-alkenyl, $C_4$–$C_8$-cycloalkenyl and $C_2$–$C_8$-alkynyl, where one or more hydrogen atoms of the $C_1$–$C_6$-alkyl, $C_3$–$C_8$-cycloalkyl, $C_2$–$C_8$-alkenyl, $C_4$–$C_8$-cycloalkenyl and/or $C_2$–$C_8$-alkynyl radicals may be substituted by halogen and/or cyano.

Particular preference is given to compounds of the formula I in which $R^4$ is selected from the group consisting of phenyl, pyridyl, pyrimidyl, pyrazynyl, pyrazolyl and naphthyl which are unsubstituted or substituted by one or more radicals selected from the group consisting of halogen, cyano, nitro, $C_1$–$C_3$-alkyl, $C_1$–$C_3$-haloalkyl, $C_1$–$C_3$-alkoxy, $C_1$–$C_3$-haloalkoxy, —C(=Z)-$R^6$, —C(=Z)-O$R^6$, —C(=Z)-S$R^6$, —C(=Z)-N$R^7R^8$, —O—C(=Z)-$R^6$, —O—C(=Z)-O$R^6$, —O—C(=Z)-S$R^6$, —O—C(=Z)-N$R^7R^8$, —S—C(=Z)-$R^6$, —S—C(=Z)-O$R^6$, —S—C(=Z)-S$R^6$, —S—C(=Z)-N$R^7R^8$, —$NR^9$—C(=Z)-$R^6$, —$NR^9$—C(=Z)-O$R^6$, —$NR^9$—C(=Z)-S$R^6$, —$NR^9$—C(=Z)-N$R^7R^8$, —O$R^6$, —S$R^6$, —S(=O)$R^6$ and —S($=$O)$_2R^6$, where Z, $R^6$, $R^7$, $R^8$ and $R^9$ are as defined above.

Very particular preference is given to the formula I in which $R^4$ is phenyl or pyridyl which carries one to three substituents from the group consisting of halogen, cyano, nitro, $C_1$–$C_3$-alkyl and $C_1$–$C_3$-haloalkyl or of combinations of these substituents.

Very particularly preferred radicals $R^4$ are trifluoromethylphenyl, chlorophenyl, nitrophenyl, nitropyridyl, trifluoromethylpyridyl, di(trifluoromethyl)pyridyl, chloropyridyl, dichloropyridyl, chlorotrifluoromethylpyridyl, trifluoromethylpyrimidyl, di(trifluoromethyl)pyrimidyl, methyltrifluoromethylpyrimidyl or trifluoromethylpyrazolyl.

Depending on the nature of the substituents defined above, the compounds of the formula (I) have acidic or basic properties and are capable of forming salts. If, for example, the compounds of the formula (I) carry groups such as hydroxyl, carboxyl or other groups which induce acidic properties, these compounds can be reacted with bases to form salts. Suitable bases are, for example, hydroxides, carbonates and bicarbonates of the alkali metals and alkaline earth metals, in particular those of sodium, potassium, magnesium and calcium, furthermore ammonia, primary, secondary and tertiary amines with ($C_1$–$C_4$) alkyl radicals and mono-, di- and trialkanolamines of ($C_1$–$C_4$)-alkanols. If, for example, the compounds of the formula (I) carry groups such as amino, alkylamino or other groups which induce basic properties, these compounds can be reacted with acids to form salts. Suitable acids are, for example, mineral acids, such as hydrochloric, sulfuric and phosphoric acid, organic acids, such as acetic acid or oxalic acid, and acidic salts, such as $NaHSO_4$ and $KHSO_4$. The salts obtainable in this manner likewise have insecticidal, acaricidal and miticidal properties.

The compounds of the formula (I) can have one or more asymmetrically substituted carbon atoms or stereoisomers on double bonds. Therefore, it is possible for enantiomers or diastereomers to be present. The invention embraces both the pure isomers and their mixtures. The mixtures of diastereomers can be separated into the isomers by customary methods, for example by selective crystallization from suitable solvents or by chromatography. Racemates can be separated into the enantiomers by customary methods.

The preparation of the compounds according to the invention is carried out by methods known per se from the literature, as described in standard works on organic synthesis, for example Houben-Weyl, Methoden der Organischen Chemie [Methods of Organic Chemistry], Georg-Thieme-Verlag, Stuttgart.

The synthesis routes described below employ reaction procedures and work-up and purification methods commonly encountered in the organic or chemical literature. Reactions generally take place in solution where, for example, alcoholic solvents such as methanol or ethanol; hydrocarbons, such as hexane, benzene or toluene; ethers, such as diethyl ether or tetrahydrofuran; chlorinated hydrocarbons, such as dichloromethane, chloroform or tetrachloroethane; amide-containing solvents, such as N,N-dimethylformamide; or sulfur-containing solvents, such as dimethyl sulfoxide or sulfolane, may be employed.

In individual cases, the reactions may also take place in suspension, emulsion or in solid phase.

Suitable reaction temperatures are in the range of from −200° C. to 250° C. However, in general, the reaction temperature is from −78° C. to 150° C.

For work-up, the reaction mixture is usually extracted with two or more solvents which are not miscible with one another. Alternatively, it is possible to use solid-phase extractions (H. G. Kicinski, Chemie in Labor and Biotechnik [Chemistry in the Laboratory and in Biological Engineering], 1996, 47(12), 542–8) or precipitation of the products in a suitable solvent or solvent mixture.

The crude products are usually purified by chromatographic processes, such as column chromatography or HPLC; by distillation or by crystallization from suitable solvents. However, other methods are not excluded.

The present invention also relates to processes for preparing compounds of the formula (I), which processes comprise the steps:

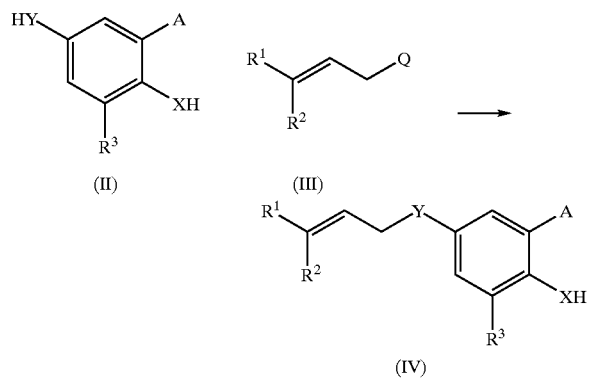

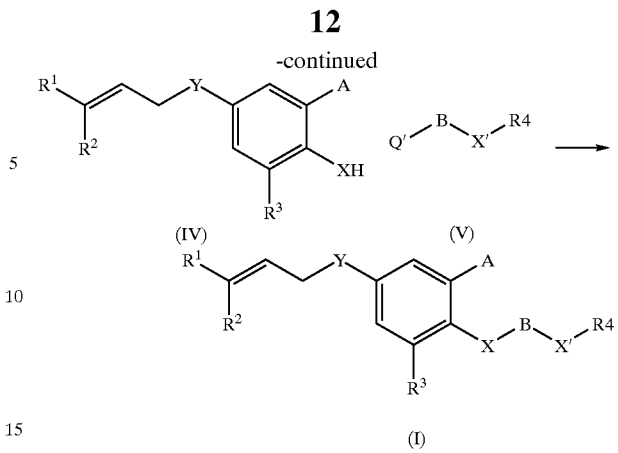

a) a reaction of the compounds of the formulae II and III to give the compound of the formula IV and b) a reaction of the compounds of the formulae IV and V to give the compound of the formula I, where $R^1$, $R^2$, $R^3$, $R^4$, A, Y, X and X' are as defined above and Q and Q' are leaving groups.

To prepare compounds of the formula (I) in which $R^1$, $R^2$, $R^3$, $R^4$, $R^5$ and A have the meanings given for formula (I) and in which Y, X and X' are each O, it is possible, for example, to proceed according to schemes 1 and 2 below.

A general procedure for preparing dihalopropene ether compounds is shown in scheme 1. Analogously, dihalopropene thioethers or amines can be prepared using corresponding thioether and amine starting materials, respectively.

Scheme 1

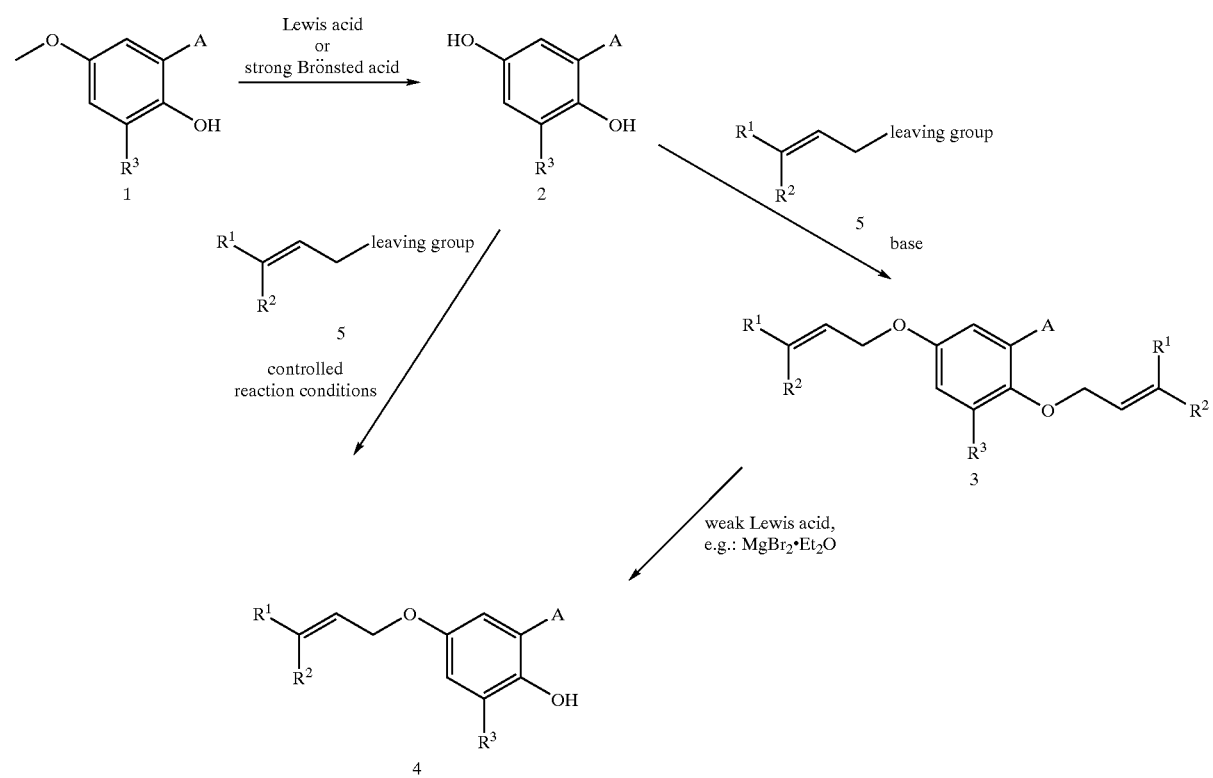

A large number of the compounds claimed herein is accessible via a building block of type 4 in scheme 1 as common intermediate. 4 is generally synthesized from compounds 1 which are commercially available or have been described in the literature. Initially, the methyl ether in 1 is cleaved by reaction with Lewis acids, such as, for example, boron tribromide, or with strong Brönsted acids, such as, for example, hydrobromic acid. The resulting compound 2 is alkylated with 5. This can take place under carefully controlled reaction conditions (for example at low temperatures and substoichiometric amounts of 5), so that the building block 4 is formed in one step. Alternatively, the alkylation may also initially yield 3, which is then converted further into 4 using a weak Lewis acid, such as, for example, magnesium dibromide/diethyl ether complex.

The phenols 4 can, as shown in scheme 2, be reacted in an alkylation reaction with a building block of type 11 or in a condensation reaction with a building block of type 12 to give the compounds 9.

way of example, diethyl azodicarboxylate in combination with triphenylphosphine may be mentioned here.

The preparation of building blocks 11 and 12 follows the procedures described in the literature (for example WO-A-96/11,909). However, it is also possible to initially convert the phenols 4 into the corresponding thiophenols 6. Suitable for this purpose is, for example, a Kwart-Newman rearrangement via a suitable N,N-dialkylthio-carbamoyl derivative of 4 (see K. -D. Gundermann, K. Hümke in Houben-Weyl, "Methoden der Organischen Chemie", Georg-Thieme-Verlag, 4th Edition, 1985, Volume E11, "Organische Schwefelverbindungen Teil I" [Organic Sulfur Compounds Part I], pages 54–55). Further conversion into the claimed compounds 8 is carried out analogously to the conversion of 4 into 9.

It is furthermore possible to convert the phenolic group in 4 into a leaving group suitable for transition-metal-catalyzed reactions (for example a trifluoromethane-sulfonate group), which is subsequently substituted, according to processes

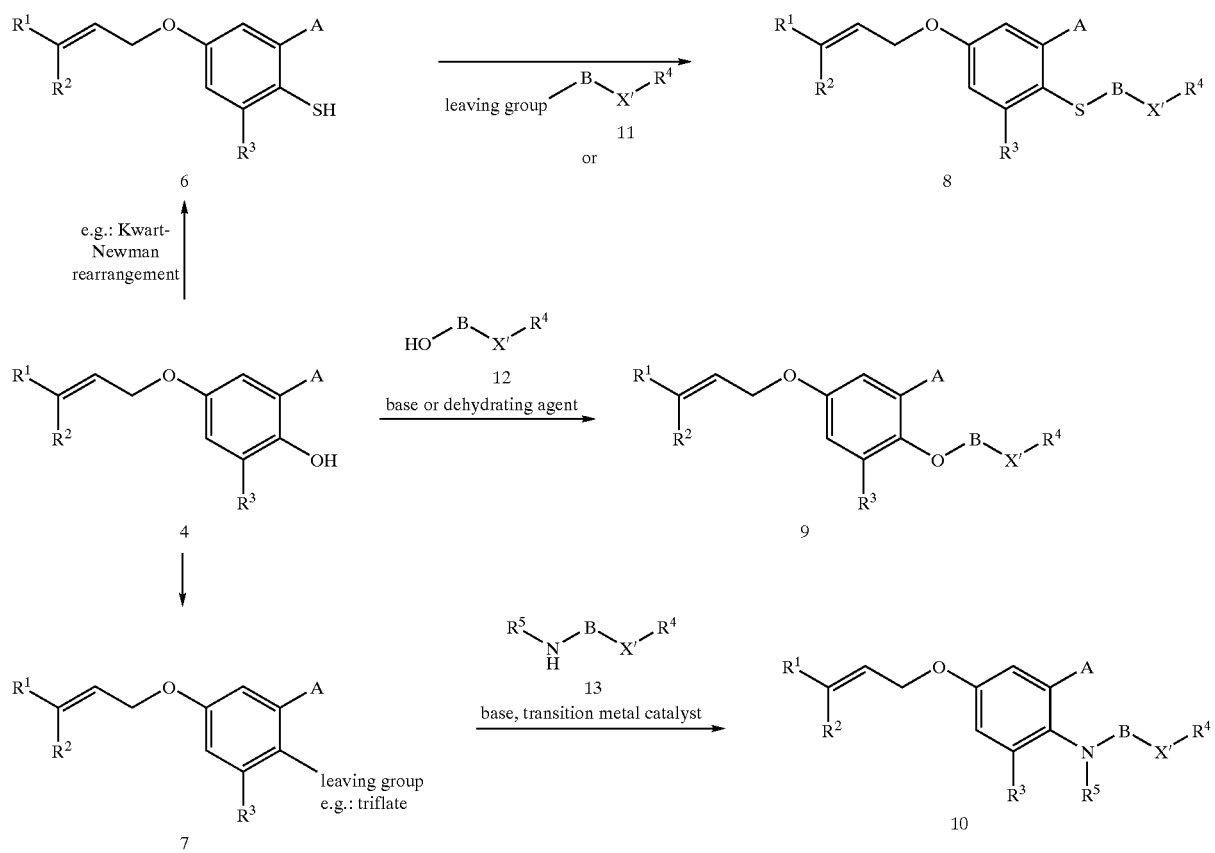

Scheme 2

In the case of an alkylation reaction, the presence of a base may be required, suitable bases being organic bases, such as, for example, triethylamine or dimethylaminopyridine, or else inorganic bases, such as, for example, calcium carbonate. To carry out a condensation, the presence of a dehydrating agent or a dehydrating combination of reagents is required.

The reaction is carried out under Mitsunobu conditions, i.e. by reacting the OH derivative with an alcohol in the presence of an azodicarboxylic diester and a phosphine. By known from the literature, by an amine of type 13 (see, for example, John P. Wolfe et al., J. Org. Chem. 2000, 65(4), 1158–1174).

Suitable transition metal catalysts are, in particular, palladium complexes. This procedure affords the claimed compounds 10.

The claimed compounds in which group A in formula I is an alkynyl or alkenyl group according to structural formulae 19 and 20 are—as shown in scheme 3—obtainable from the monobenzoylated hydroquinones 14, which are known from the literature.

Scheme 3

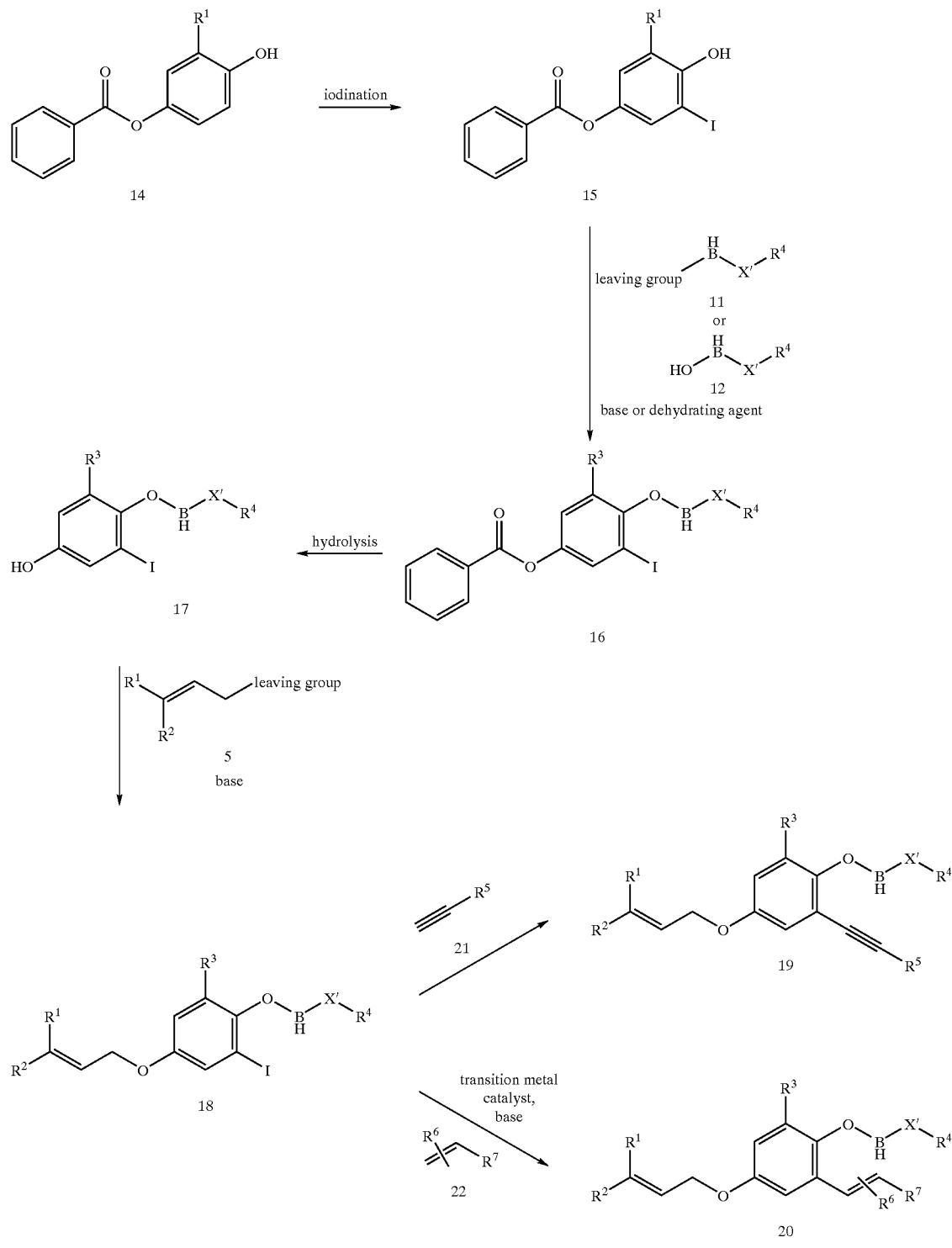

The monobenzoylated hydroquinones 14 are initially selectively brominated or iodinated in the ortho-position to the free phenol group, by action of a suitable reagent. An iodination can be effected, inter alia, with the aid of a mixture of chloramine T and sodium iodide, giving structures 15. 15 is reacted in an alkylation or condensation with building blocks 11 or 12 (analogously to the conversion of 4 into 9), giving the compounds 16. The benzoyl group in 16 is removed hydrolytically in a basic reaction medium. Basic reaction conditions can be established using, in particular, inorganic bases, such as, for example, sodium hydroxide or potassium carbonate. The resulting phenols 17 are alkylated using a building block 5 and any base. Final introduction of an alkynyl group, giving the claimed compounds 19, or an alkenyl group, giving the claimed compounds 20, is carried out by reaction with suitable alkynes 21 and suitable alkenes 22, respectively, a transition metal catalyst and any base. Suitable transition metal catalysts are, in particular, palladium complexes or mixtures of palladium complexes and inorganic copper compounds.

The claimed compounds or intermediates in which group A of formula I or of structures 4, 6 or 7 is an acetyl group or an alkoxycarbonyl group can be used as starting materials for further modifications of group A using standard reactions of organic chemistry. This is shown in an exemplary manner in scheme 4.

It is possible, for example, to alkylate and/or brominate a compound of structure 23 in the α-position to the carbonyl group. The literature mentions a number of suitable alkylation processes, of which the alkylation of metallated hydrazones according to Chem. Ber. 1978, 111, 1337–1361 may be mentioned by way of example. A bromination can be effected by reaction with bromine or a large number of possible brominating agents, in most cases in an inert solvent. The resulting bromoketones can be reacted with primary thioamides, affording thiazoles of the formula 25. The reaction of compounds of the formula 23 with hydroxylamines or salts thereof gives oximes which can be modified further in the α-position, as desired, for example by Scheme 4

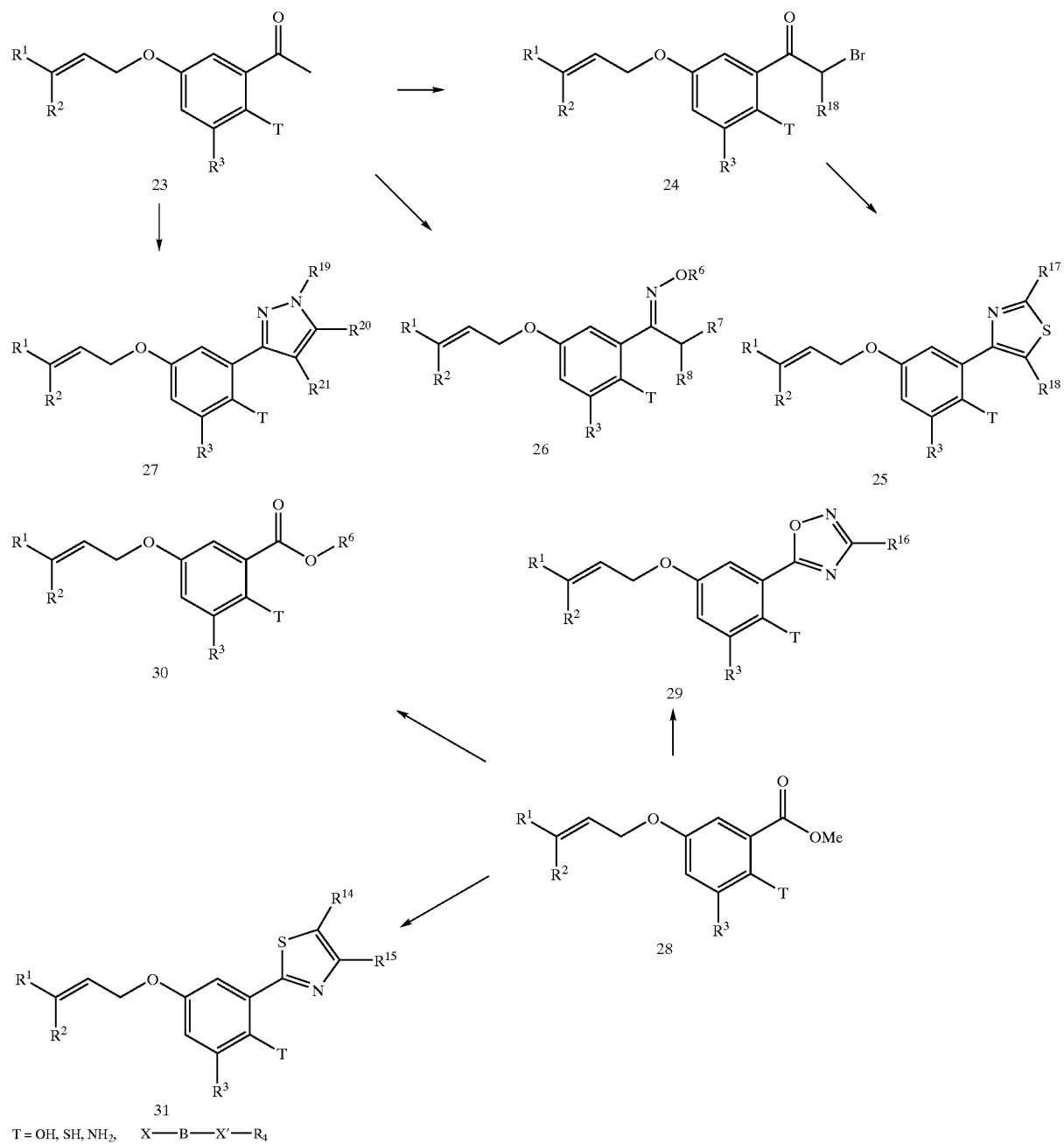

alkylation, furnishing structures of type 26. Reaction of the acyl group in 23 with suitable amide acetals such as, for example, N,N-dimethylformamide O,O-dimethyl acetal affords an enaminoketone as intermediate, further reaction of which with any hydrazines leads to structures of type 27.

Compounds of structure 28 can be reacted with any amidoximes, giving 1,2,4-oxadiazoles of formula 28. This reaction can take place in one step using a strong base, in most cases a protic solvent, or in two steps via the corresponding open-chain O-acylamidoximes as intermediate. Transesterification of 28 with any alcohols according to a standard method as described, for example, in Org. Syn. Coll. Vol. 1955, 3,146, affords the corresponding esters 30. According to the process described in Org. Coll. Vol. 1955, 3, 516, 536 or any equivalent process, the ester in compounds 28 can be converted into a primary amide. With the aid of a suitable thiolating agent, such as, for example, Lawesson's reagent (Tetrahedron 1985, 41, 5061), the corresponding thioamides are obtained, further reaction of which with any α-haloketones or α-haloaldehydes gives the thiazoles of type 31. Hydrolysis of the ester function in 28 under basic or acidic protic conditions gives the corresponding acids, which are degraded, for example in a Curtius rearrangement. Suitable for this purpose is, inter alia, action of diphenylphosphoryl azide (DPPA), as described in J. Am. Chem. Soc. 1972, 94, 6203. If this rearrangement is carried out in the presence of a suitable alcohol $R^3$—OH, the carbamates 32 are obtained. In the presence of a primary or secondary amine, the products are the corresponding ureas.

Collections of compounds of the formula (I) which can be synthesized by the abovementioned scheme may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A series of commercially available apparatuses as are offered by, for example, Stem Corporation, Woodrolfe Road, Tollesbury, Essex, CM98SE, England or H+P Labortechnik GmbH, Bruckmannring 28, 85764 Oberschleißheim, Germany may be used for the parallel procedure of the reaction and work-up. For the parallel purification of compounds of the formula (I), or of intermediates obtained during the preparation, use may be made, inter alia, of chromatography apparatuses, for example those from ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to the methods described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products from IRORI, 11149 North Torrey Pines Road, La Jolla, Calif. 92037, USA are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation by the processes described herein yields compounds of the formula (I) in the form of substance collections which are termed libraries.

The present invention also relates to libraries which comprise at least two compounds of the formula (I).

The compounds of the formula (I) are suitable for controlling animal pests, in particular insects, arachnids, helminthes and mollusks, very especially preferably for controlling insects and arachnids which are encountered in agriculture, in livestock breeding, in forests, in the protection of stored goods and materials, and in the hygiene sector, and have good plant tolerance and favorable toxicity to warm-blooded species. They are active against normally sensitive and resistant species and against all or individual developmental stages. The abovementioned pests include:

From the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Eotetranychus* spp., *Oligonychus* spp., *Eutetranychus* spp.

From the order of the Isopoda, for example, *Oniscus aselus, Armadium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis, Schistocerca gregaria.*

From the order of the Isoptera, for example, *Reticulitermes* spp.

From the order of the Anoplura, for example, *Phylloera vastatrix, Pemphigus* spp., *Pediculus humanus corporis, Haematopinus* spp., *Linognathus* spp.

From the order of the Mallophaga, for example, *Trichodectes* pp., *Damalinea* spp.

From the order of the Thysanoptera, for example, *Hercinothrips femoralis, Thrips tabaci.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum,*

*Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padelia, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylloides chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrynchus assimilis, Hypera postica, Dermestes* spp., *Trogoderma, Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hypobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa.*

From the order of the Siphonaptera, for example, *Xenopsylla cheopsis, Ceratophyllus* spp.

From the order of the Arachnida, for example, *Scorpio maurus, Latrodectus mactans.*

From the class of the helminths, for example, *Haemonchus, Trichostrongulus, Ostertagia, Cooperia, Chabertia, Strongyloides, Oesophagostomum, Hyostrongulus, Ancylostoma, Ascaris* and *Heterakis* and also *Fasciola.*

From the class of the Gastropoda, for example, *Deroceras* spp., *Arion* spp., *Lymnaea* spp., *Galba* spp., *Succinea* spp., *Biomphalaria* spp., *Bulinus* spp., *Oncomelania* spp.

From the class of the Bivalva, for example, *Dreissena* spp.

The plant-parasitic nematodes which can be controlled in accordance with the invention include, for example, the root-parasitic soil-dwelling nematodes such as, for example, those of the genera *Meloidogyne* (root knot nematodes, such as *Meloidogyne incognita, Meloidogyne hapla* and *Meloidogyne javanica*), *Heterodera* and *Globodera* (cyst-forming nematodes, such as *Globodera rostochiensis, Globodera pallida, Heterodera trifolii*) and of the genera *Radopholus,* such as *Radopholus similis, Pratylenchus* such as *Pratylenchus neglectus, Pratylenchus penetrans* and *Pratylenchus curvitatus;*

*Tylenchulus* such as *Tylenchulus semipenetrans, Tylenchorhynchus,* such as *Tylenchorhynchus dubius* and *Tylenchorhynchus claytoni, Rotylenchus* such as *Rotylenchus robustus, Heliocotylenchus* such as *Haliocotylenchus multicinctus, Belonoaimus* such as *Belonoaimus longicaudatus, Longidorus* such as *Longidorus elongatus, Trichodorus* such as *Trichodorus primitivus* and *Xiphinema* such as *Xiphinema index.*

Other nematode genera which can be controlled using the compounds according to the invention are *Ditylenchus* (stem parasites, such as *Ditylenchus dipsaci* and *Ditylenchus destructor*), *Aphelenchoides* (foliar nematodes, such as *Aphelenchoides ritzemabosi*) and *Anguina* (seed nematodes, such as *Anguina tritici*).

The invention also relates to compositions, for example crop protection compositions, preferably insecticidal, acaricidal, ixodicidal, nematicidal, molluscicidal or fungicidal, especially preferably insecticidal and acaricidal, compositions which comprise one or more compounds of the formula (I) in addition to suitable formulation auxiliaries.

To prepare the compositions according to the invention, the active substance and the other additives are combined and brought into a suitable use form.

The invention also relates to compositions, in particular insecticidal and acaricidal compositions, which comprise the compounds of the formula (I) in addition to suitable formulation auxiliaries.

In general, the compositions according to the invention comprise 1 to 95% by weight of the active substances of the formula (I). They can be formulated in various ways, depending on the biological and/or chemical-physical parameters which prevail. The following are examples of possible formulations:

Wettable powders (WP), emulsifiable concentrates (EC), aqueous solutions (SL), emulsions, sprayable solutions, oil- or water-based dispersions (SC), suspo-emulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulations are known in principle and are described, for example, in: Winnacker-Küchler, "Chemische Technologie" [Chemical Technology], Volume 7, C. Hanser Verlag Munich, 4th Edition 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The necessary formulation auxiliaries, i.e. carrier materials and/or surface-active substances such as inert materials, surfactants, solvents and other additives, are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie", Volume 7, C. Hanser Verlag Munich, 4th Edition 1986.

Based on these formulations, it is also possible to prepare combinations with other pesticidally active materials, fertilizers and/or growth regulators, for example in the form of a ready-mix formulation or a tank mix. Wettable powders are preparations which are uniformly dispersible in water which, besides the active substance, also comprise wetters, for example polyoxyethylated alkylphenols, polyoxyethylated fatty alcohols, alkylsulfonates or alkylphenolsulfonates and dispersants, for example sodium lignosulfonate or sodium 2,2'-dinaphthylmethane-6,6'-disulfonate, in addition to a diluent or inert material.

Emulsifiable concentrates are prepared by dissolving the active substance in an organic solvent, for example butanol, cyclohexanone, dimethylformamide, xylene or else higher-boiling aromatics or hydrocarbons, with addition of one or more emulsifiers. As emulsifiers, the following can be used, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained, for example, by grinding the active substance with finely divided solid materials, for example talc or natural clays, such as kaolin, bentonite, pyrophyllite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example polyvinyl alcohol or sodium polyacrylate, or else mineral oils. Suitable active substances can also be granulated in the manner which is customary for the preparation of fertilizer granules, if desired as a mixture with fertilizers.

The active substance concentration in wettable powders is usually approximately 10 to 90% by weight, the remainder to 100% by weight is composed of customary formulation constituents. In the case of emulsifiable concentrates, the active substance concentration may be approximately 5 to 80% by weight. Formulations in the form of dusts usually comprise 5 to 20% by weight of active substance, sprayable solutions approximately 2 to 20% by weight. In the case of granules, the active substance content depends partly on whether the active compound is in liquid or solid form and on which granulation auxiliaries, fillers and the like are being used.

Besides, the abovementioned active substance formulations comprise, if appropriate, the tackifiers, wetters, dispersants, emulsifiers, penetrants, solvents, fillers or carriers which are conventional in each case.

For use, the concentrates, which are present in commercially available form, are, if desired, diluted in the customary manner, for example in the case of wettable powders, emulsifiable concentrates, dispersions and in some cases also microgranules, using water. Preparations in the form of dusts and granules and sprayable solutions are usually not diluted any further with other inert substances prior to use.

The application rate required varies with the external conditions such as, inter alia, temperature and humidity. It may vary within wide limits, for example between 0.0005 and 10.0 kg/ha or more of active substance, but it is preferably between 0.001 and 5 kg/ha of active compound.

The active substances according to the invention, in their commercially available formulations and in the use forms prepared from these formulations, may be present in mixtures with other active substances such as insecticides, attractants, sterilants, acaricides, nematicides, fungicides, growth regulatory substances or herbicides.

The pesticides include, for example, phosphoric esters, carbamates, carboxylic esters, formamidines, tin compounds and materials produced by microorganisms.

Preferred components in mixtures are:
1. from the group of the phosphorus compounds acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phospho-carb (BAS-301), phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;
2. from the group of the carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl (methyl)carbamate, oxamyl, pirimicarb, propoxur, thiodicarb, thiofanox, 1-methylthio(ethylideneamino)-N-methyl-N-(morpholinothio)carbamate (UC 51717), triazamate;
3. from the group of the carboxylic esters acrinathrin, allethrin, alphametrin, 5-benzyl-3-furylmethyl (E)-(1R)-cis-2,2-dimethyl-3-(2-oxothiolan-3-ylidenemethyl)cyclopropanecarboxylate, beta-cyfluthrin, beta-cypermethrin, bioallethrin, bioallethrin ((S)-cyclopentylisomer), bioresmethrin, bifenthrin, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S-41311), lambda-cyhalothrin, permethrin, phenothrin ((R) isomer), prallethrin, pyrethrins (natural products), resmethrin, tefluthrin, tetramethrin, theta-cypermethrin (TD-2344), tralomethrin, transfluthrin, zeta-cypermethrin (F-56701);
4. from the group of the amidines amitraz, chlordimeform;
5. from the group of the tin compounds cyhexatin, fenbutatin oxide;
6. others abamectin, ABG-9008, acetamiprid, *Anagrapha falcitera,* AKD-1022, AKD-3059, ANS-118, *Bacillus thuringiensis, Beauveria bassianea,* bensultap, bifenazate (D-2341), binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chromafenozide (ANS-118), CG-216, CG-217, CG-234, A-184699, 2-naphthylmethyl cyclopropane-carboxylate (Ro12-0470), cyromazin, diacloden (thiamethoxam), diafenthiuron, ethyl N-(3,5-dichloro-4-(1,1,2,3,3,3-hexafluoro-1-propyloxy)phenyl)carbamoyl)-2-chlorobenzocarboximidate, DDT, dicofol, diflubenzuron, N-(2,3-dihydro-3-methyl-1,3-thiazol-2-ylidene)-2,4-xylidine, dinobuton, dinocap, diofenolan, DPX-062, emamectin benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), flonicamid (IKI-220), 2-fluoro-5-(4-(4-fenoxyphenyl)-4-methyl-1-pentyl) diphenylether (MTI 800), granulosis and nuclear polyhedrosis viruses, fenpyroximate, fenthiocarb, flubenzimine, flucycloxuron, flufenoxuron, flufenprox (ICI-A5683), fluproxyfen, gamma-HCH, halfenozide (RH-0345), halofenprox (MTI-732), hexaflumuron (DE_473), hexythiazox, HOI-9004, hydramethylnon (AC 217300), lufenuron, imidacloprid, indoxacarb (DPX-MP062), kanemite (AKD-2023), M-020, MTI-446, ivermectin, M-020, methoxyfenozide (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-196, NC-1111, NNI-9768, novaluron (MCW-275), OK-9701, OK-9601, OK-9602, propargite, pymethrozine, pyridaben, pyridalyl (S-1812), pyrimidifen (SU-8801), RH-0345, RH-2485, RYI-210, S-1283, S-1833, SB7242, SI-8601, silafluofen, silomadine (CG-177), spinosad, SU-9118, spirodiclofen (BAI-2740), spiromesifen, tebufenozide, tebufenpyrad (MK-239), teflubenzuron, tetradifon, tetrasul, thiacloprid, thiocyclam, TI-435, tolfenpyrad (OMI-88), triazamate (RH-7988), triflumuron, verbutin, vertalec (Mykotal), YI-5301.

The abovementioned components for combinations are known active substances, many of which are described in Ch. R Worthing, S. B. Walker, The Pesticide Manual, 11th Edition, British Crop Protection Council, Farnham 1997.

The active substance content of the use forms prepared from the commercially available formulations may range from 0.00000001 up to 95% by weight of active substance, preferably between 0.00001 and 1% by weight.

Application is effected in a customary manner adapted to suit the use forms.

Therefore in further aspects of the invention there are provided the use of the compounds of the formula (I) or salts thereof for controlling animal pests; and a method for controlling animal pests, comprising the step of directly or indirectly applying to the pest a compound of the formula (I) or a salt thereof.

The active substances according to the invention are also suitable for controlling endoparasites and ectoparasites in the human and veterinary medicine sector and/or in the field of animal keeping. The active substances according to the invention are applied here in a known manner, such as by oral administration in the form of, for example, tablets, capsules, drinks or granules, by dermal application in the form of, for example, dipping, spraying, pouring on and spotting on, and dusting, and by parenteral administration in the form of, for example, an injection.

Accordingly, the compounds of the formula (I) according to the invention can also be employed particularly advantageously for the treatment of warm-blooded species, especially in livestock keeping (for example cattle, sheep, pigs and poultry such as chickens, geese and the like). In a preferred embodiment of the invention, the compounds, if appropriate in suitable formulations, are administered orally to the animals, if appropriate together with the drinking water or feed. Since excretion in the feces is efficient, the development of insects in the animals' feces can be prevented very easily in this manner. The dosages and formulations which are suitable in each case depend, in particular, on the species and the developmental stage of the productive livestock and also on the risk of infestation and can be determined readily and established by customary methods. For example, the compounds can be employed in cattle at dosages of 0.01 to 1 mg/kg of bodyweight.

In addition to their lethal effect on pests, the compounds of the formula (I) or their salts also have a pronounced repellant effect.

A repellant for the purpose of the description is a substance or substance mixture which has a warding-off or fending-off effect on other life organisms, in particular harmful pests and nuisance pests. The term also encompasses effects such as the antifeeding effect, where the intake of feed is disturbed or prevented (antifeedant effect), suppression of oviposition, or an effect on the development of the population.

The invention therefore also provides the use of compounds of the formula (I) or their salts for achieving the abovementioned effects, in particular in the case of the pests stated in the biological examples.

The invention also provides a method for fending off, or warding off, harmful organisms, where one or more compounds of the formula (I) or their salts are applied to the site from which the harmful organisms are to be fended off or warded off.

In the case of a plant, application may mean, for example, a treatment of the plant, but also of the seed.

As regards the effect on populations, it is interesting to note that effects can also be observed in succession during the development of a population, where summation may take place. In such a case, the individual effect itself may only have an efficacy of markedly less than 100% but in total an efficacy of 100% is still achieved in the end.

Moreover, the compounds of the formula (I) or their salts are distinguished by the fact that the composition is usually applied earlier than in the case of a direct control, if the abovementioned effects are to be exploited. The effect frequently lasts over a long period, so that a duration of action of over 2 months is achieved.

The effects are observed in insects, arachnids and the other abovementioned pests.

In addition to the abovementioned application methods, the active compounds of the formula (I) according to the invention have excellent systemic action. Accordingly, the active compounds can also be introduced into the plants via parts of the plant, both below ground and above ground (root, stem, leaf), if the active compounds are applied, in liquid or solid form in the direct vicinity of the plant (for example granules in soil application, application in flooded rice paddies).

Furthermore, the active compounds according to the invention are particularly useful for the treatment of vegetative and generative plant propagation material, such as, for example, of seeds, for example of cereals, vegetables, cotton, rice, sugar beet and other crops and ornamental plants, of bulbs, seedlings and tubers of other crops and ornamental plants which are propagated vegetatively. The treatment can be carried out before sowing or before planting (for example by special seed coating techniques, by dressing in liquid or solid form or as a seed box treatment), during sowing or planting or after sowing or planting by special application techniques (for example furrow treatment). The amount of active compound used can vary within a relatively large range, depending on the application. In general, the application rates are between 1 g and 10 kg of active compound per hectare of soil surface.

The compounds of the formula (I) can also be employed for controlling harmful plants in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

The use in economically important transgenic crops of useful plants and ornamentals is preferred, for example of cereals such as wheat, barley, rye, oats, millet, rice, cassava and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

Therefore in further aspects of the invention there are provided the use of the compounds of formula (I) for controlling harmful organisms in transgenic crop plants; and a method for controlling harmful organisms in transgenic crop plants comprising the step of directly or indirectly applying to the pest a compound of the formula (I).

The use of the compounds according to the invention embraces, in addition to direct application onto the pests, any other application in which compounds of the formula (I) act on the pests. Such indirect applications can, for example, be the use of compounds which, for example in the soil, the plant or the pest, decompose into compounds of the formula (I) and/or are degraded into compounds of the formula (I). The examples below serve to illustrate the invention.

A. CHEMICAL EXAMPLES

Example A

3-Acetyl-1-chloro-5-(3,3-dichloroprop-2-enyloxy)-2-[3-(5-trifluoromethyl-pyrid-2-yloxy)propyloxy]benzene (No. 27)

Step 1: 3-acetyl-1-chloro-2,5-dihydroxybenzene 8.7 g of 3-acetyl-1-chloro-2-hydroxy-5-methoxybenzene were taken up in 150 ml of hydrobromic acid (48% strength in water). 1.69 g of red phosphorus were added, and the mixture was then stirred at 85° C. for 15 hours. After cooling, the reaction mixture was poured into about 1 liter of ice-cold water and extracted with ethyl acetate. The crude product obtained after drying and concentration of the ethyl acetate phase was purified by column chromatography. Yield: 2.9 g (36%)

$^1$H-NMR (CDCl$_3$): δ=2.61 (s, 3H); 4.73 (s, 1H); 7.18 (m, 2H), 12.33 (s, 1H).

Step 2: 3-acetyl-2,5-bis-(3,3-dichloroprop-2-enyloxy)-1-chlorobenzene 2.9 g of 3-acetyl-1-chloro-2,5-dihydroxybenzene were dissolved in 29 ml of acetone, and 3.39 g of 1,1,3-trichloropropene, 4.3 g of potassium carbonate and 0.7 g of sodium iodide were added. The mixture was heated under reflux for 5 hours (monitored by TLC). The reaction mixture was then allowed to cool and concentrated using a rotary evaporator, and the resulting crude product was subjected to chromatographic purification. Yield: 6.1 g (99%)

$^1$H-NMR (CDCl$_3$): δ=2.60 (s, 3H); 4.58 (d, 2H); 4.62 (d, 2H); 6.12 (t, 1H); 6.21 (t,1H); 7.01 (d, 1H); 7.09 (d, 1H).

Step 3: 3-acetyl-1-chloro-5-(3,3-dichloroprop-2-enyloxy)-2-hydroxybenzene 6.1 g of 3-acetyl-2,5-bis-(3,3-dichloroprop-2-enyloxy)-1-chlorobenzene were dissolved in 160 ml of toluene. 7.79 g of magnesium dibromide/diethyl ether complex, dissolved in 25 ml of diethyl ether, were added to this solution, and the mixture was then stirred at 85° C. for 6 hours. After the reaction had ended according to TLC, the mixture was allowed to cool, about 300 ml of water were added and the organic phase was separated off. The aqueous phase was re-extracted twice with ethyl acetate, and the combined organic phases were then washed with saturated sodium chloride solution. After drying and concentration of the organic phase, the crude product was purified chromatographically. Yield: 2.86 g (64%)

$^1$H-NMR (CDCl$_3$): δ=2.62 (s, 3H); 4.62 (d, 2H); 6.13 (t, 1H); 7.17 (d, 1H), 7.22 (d, 1H); 12.40 (s, 1H).

Step 4: 3-acetyl-1-chloro-5-(3,3-dichloroprop-2-enyloxy)-2-[3-(5-trifluoromethylpyrid-2-yloxy)propyloxy]benzene Under an atmosphere of protective gas, 1.2 g of 3-acetyl-1-chloro-5-(3,3-dichloroprop-2-enyloxy)-2-hydroxybenzene, 0.9 g of 3-(5-trifluoromethylpyrid-2-yloxy)propan-1-ol and 1.12 g of triphenylphosphine were dissolved in 35 ml of dry tetrahydrofuran (THF). With ice-bath cooling, 0.74 g of diethyl azodicarboxylate was added dropwise. After about 30 minutes, the ice-bath was removed, and the mixture was stirred at room temperature for 15 hours. The mixture was then concentrated under reduced pressure and the residue was taken up in a mixture of ethyl acetate and water. After shaking, the organic phase was isolated, dried and concentrated under reduced pressure. The crude product was purified chromatographically. Yield: 1.52 g (74%)

$^1$H-NMR (CDCl$_3$): δ=2.27 (m, 2H); 2.6 (s, 3H); 4.08 (t, 2H); 4.60 (m, 4H); 6.12 (t, 1H); 6.81 (d, 1H); 6.99 (d, 1H); 7.08 (d, 1H); 7.77 (dd, 1H); 8.42 (br. s, 1H).

Example B 1-chloro-5-(3,3-dichloroprop-2-enyloxy)-3-(3-ethyl-1,2,4-oxadiazol-5-yl)-2-[3-(5-trifluoromethylpyrid-2-yloxy)propyloxy]benzene (No. 356)

Step 1: 3-chloro-2,5-dihydroxybenzoic acid 9.95 g of methyl 3-chloro-2-hydroxy-5-methoxybenzoate were taken up in 300 ml of hydrobromic acid (48% strength in water). 1.79 g of red phosphorus were added, and the mixture was then stirred at 85° C. for 15 hours. After cooling, the reaction mixture was poured into about 1 liter of ice-cold water and extracted with ethyl acetate. The crude product obtained after drying and concentration of the ethyl acetate phase was used for the next step without further purification.

Step 2: methyl 3-chloro-2,5-dihydroxybenzoate 8.65 g of the crude product of the previous step were dissolved in 12 ml of anhydrous methanol, and 0.5 ml of concentrated sulfuric acid was added. The mixture was heated under reflux for 6 hours. After cooling, the reaction mixture was concentrated under reduced pressure, diluted with tert-butyl methyl ether to about 200 ml and washed with water and saturated sodium bicarbonate solution. The ether phase was dried and concentrated and the crude product was purified chromatographically. Yield: 4.85 g (52% over 2 steps)

$^1$H-NMR (CDCl$_3$): δ=3.97 (s, 3H); 4.61 (br. s, 1H); 7.15 (d, 1H); 7.22 (d, 1H); 10.83 (s, 1H).

Step 3: methyl 3-chloro-5-(3,3-dichloroprop-2-enyloxy)-2-hydroxybenzoate 1.67 g of methyl 3-chloro-2,5-dihydroxybenzoate, 2 g of 1,1,3-trichloropropene, 2.27 g of potassium carbonate and 0.37 g of sodium iodide were dissolved in 17 ml acetone, and the mixture was stirred at 50° C. for 16 hours. After cooling, the mixture was concentrated under reduced pressure and the crude product was taken up in ethyl acetate and washed with water. Drying and concentration of the ethyl acetate phase gave a crude product which was dissolved in 65 ml of toluene. 2.95 g of magnesium dibromide/diethyl ether complex, dissolved in 10 ml of diethyl ether, were added using a pipette, and the mixture was heated at 80° C.–85° C. for 20 hours. The mixture was allowed to cool, about 300 ml of water were added and the organic phase was separated off. The aqueous phase was re-extracted twice with ethyl acetate, and the combined organic phases were then washed with saturated sodium chloride solution. After drying and concentration of the organic phase, the crude product was purified chromatographically. Yield: 2.01 g (79%)

$^1$H-NMR (CDCl$_3$): δ=3.99 (s, 3H); 4.60 (d, 2H); 6.12 (t, 1H); 7.20 (d, 1H), 7.25 (d, 1H); 10.95 (s, 1H).

Step 4: methyl 3-chloro-5-(3,3-dichloroprop-2-enyloxy)-2-[3-(5-trifluoromethylpyrid-2-yloxy)propyloxy]benzoate (No. 39)

Under an atmosphere of protective gas, 1.85 g of methyl 3-chloro-5-(3,3-dichloroprop-2-enyloxy)-2-hydroxybenzoate, 1.3 g of 3-(5-trifluoromethylpyrid-2-yloxy)-propan-1-ol and 1.64 g of triphenylphosphine were dissolved in 50 ml of dry tetrahydrofuran (THF). With ice-bath cooling, 1.09 g of diethyl azodicarboxylate were added dropwise. After about 30 minutes, the ice-bath was removed, and the mixture was stirred at room temperature for 15 hours. The mixture was then concentrated under reduced pressure and the residue was taken up in a mixture of ethyl acetate and water. After shaking, the organic phase was isolated, dried and concentrated under reduced pressure. The crude product was purified chromatographically. Yield: 1.79 g (59%)

$^1$H-NMR (CDCl$_3$): δ=2.30 (m, 2H); 3.86 (s, 3H); 4.16 (t, 2H); 4.62 (m, 4H); 6.13 (t, 1H); 6.80 (d, 1H); 7.10 (d, 1H); 7.21 (d, 1H); 7.77 (dd, 1H); 8.42 (br. s, 1H).

Step 5: 1-chloro-5-(3,3-dichloroprop-2-enyloxy)-3-(3-ethyl-1,2,4-oxadiazol-5-yl)-2-[3-(5-trifluoromethylpyrid-2-yloxy)propyloxy]benzene 0.05 g of methyl 3-chloro-5-(3,3-dichloroprop-2-enyloxy)-2-[3-(5-trifluoromethylpyrid-2-yloxy)propyloxy]benzoate and 0.028 g of propionamidoxime were dissolved in 1 ml of anhydrous ethanol. A solution of 0.008 g of sodium in 0.5 ml of ethanol was added to this solution. The mixture was stirred at 40° C. for 2 hours and at room temperature for 20 hours. The mixture was then concentrated, and diethyl ether and water were added. After shaking, the ether phase was isolated, dried and concentrated under reduced pressure, and the crude product was purified chromatographically. Yield: 0.017 g (32%)

$^1$H-NMR (CDCl$_3$): δ=1.40 (t, 3H); 2.38 (m, 2H); 2.82 (q, 2H); 4.19 (t, 2H); 4.66 (m, 4H); 6.15 (t, 1H); 6.80 (d, 1H); 7.17 (d, 1H); 7.47 (d, 1H); 7.76 (dd, 1H); 8.43 (br. s, 1H).

Example C 3-acetyl-1-chloro-5-(3,3-dichloroprop-2-enyloxy)-2-[4-(5-trifluoromethylpyrid-2-yloxy)butyloxy]benzene (No. 59)

Under an atmosphere of protective gas, 0.1 g of 3-acetyl-1-chloro-5-(3,3-dichloroprop-2-enyloxy)-2-hydroxybenzene, 0.08 g of 4-(5-trifluoromethylpyrid-2-yloxy)butan-1-ol and 0.093 g triphenylphosphine were dissolved in 2 ml of dry tetrahydrofuran (THF). With ice-bath cooling, 56 μl of diethyl azodicarboxylate were added dropwise. After about 30 minutes, the ice-bath was removed, and the mixture was stirred at room temperature for 15 hours. The mixture was then concentrated under reduced pressure and the residue was taken up in a mixture of ethyl acetate and water. After shaking, the organic phase was isolated, dried and concentrated under reduced pressure. The crude product was purified chromatographically. Yield: 0.051 g (35%)

$^1$H-NMR (CDCl$_3$): δ=1.96 (m, 4H); 2.6 (s, 3H); 4.02 (m, 2H); 4.41 (m, 2H); 4.59 (d, 2H); 6.12 (t, 1H); 6.80 (d, 1H); 7.00 (d, 1H); 7.08 (d, 1H); 7.78 (dd, 1H); 8.42 (br. s, 1H).

Example D 1-chloro-3-(2-chlorophenylethynyl)-5-(3,3-dichloroprop-2-enyloxy)-2-[3-(5-trifluoromethylpyrid-2-yloxy)propyloxy]benzene (No. 226)

Step 1: 5-benzoyloxy-3-chloro-2-hydroxy-1-iodobenzene 3 g of 5-benzoyloxy-1-chloro-2-hydroxybenzene were dissolved in 35 ml of DMF. 2.17 g of sodium iodide and 3.29 g of chloramin T were added. After one hour of stirring at room temperature, about 500 ml of water were added to the mixture, which was then extracted with ethyl acetate. The organic phase was washed with 5% strength sodium thiosulfate solution, dried and concentrated using a rotary evaporator. The resulting product was clean enough for the next reaction. Yield: 3.81 g (84%)

$^1$H-NMR (CDCl$_3$): δ=4.70 (br. s, 1H); 7.30 (d, 1H); 7.54 (m, 3H); 7.63 (m, 1H); 8.17 (d, 2H).

Step 2: 5-benzoyloxy-3-chloro-1-iodo-2-[3-(5-trifluoromethylpyrid-2-yloxy)propyloxy]-benzene Under an atmosphere of protective gas, 3.5 g of 5-benzoyloxy-3-chloro-2-hydroxy-1-iodobenzene, 2.07 g of 3-(5-trifluoromethylpyrid-2-yloxy)propan-1-ol and 2.57 g of triphenylphosphine were dissolved in 100 ml of dry tetrahydrofuran (THF). With ice-bath cooling, 1.71 g of diethyl azodicarboxylate were added dropwise. After about 30 minutes, the ice-bath was removed, and the mixture was stirred at room temperature for 15 hours. The mixture was then concentrated under reduced pressure and the residue was taken up in a mixture of ethyl acetate and water. After shaking, the organic phase was isolated, dried and concentrated under reduced pressure. The crude product was purified chromatographically. Yield: 3.12 g (58%)

$^1$H-NMR (CDCl$_3$): δ=2.38 (quint., 2H); 4.19 (t, 2H); 4.65 (t, 2H); 6.82 (d, 1H); 7.31 (d, 1H); 7.53 (m, 2H); 7.58 (d, 1H); 7.65 (m, 1H); 7.78 (dd, 1H); 8.16 (d, 1H); 8.43 (br. s, 1H).

Step 3: 3-chloro-5-hydroxy-1-iodo-2-[3-(5-trifluoromethylpyrid-2-yloxy)propyloxy]-benzene 3.12 g of 5-benzoyloxy-3-chloro-1-iodo-2-[3-(5-trifluoromethylpyrid-2-yloxy)propyloxy]benzene were dissolved in 16 ml of tetrahydrofuran and 7.8 ml of methanol, and 3.9 ml of 2N aqueous sodium hydroxide solution were added. After 30 minutes of stirring at room temperature. 3.9 ml of 2N hydrochloric acid were added, and the reaction mixture was concentrated under reduced pressure. Saturated sodium chloride solution and ethyl acetate were added to the residue, and the mixture was shaken. The ethyl acetate phase was isolated, dried and concentrated. The resulting crude product was purified chromatographically. Yield: 2.03 g (80%)

¹H-NMR (CDCl₃): δ=2.34 (quint., 2H); 4.09 (t, 2H); 4.62 (t, 2H); 5.13 (s, 1H); 6.82 (d, 1H); 6.88 (d, 1H); 7.17 (d, 1H); 7.78 (dd, 1H); 8.43 (br. s, 1H).

Step 4: 3-chloro-5-(3,3-dichloroprop-2-enyloxy)-1-iodo-2-[3-(5-trifluoromethylpyrid-2--yloxy)propyloxy]benzene 2.23 g of 3-chloro-5-hydroxy-1-iodo-2-[3-(5-trifluoromethylpyrid-2-yloxy)propyloxy]-benzene were dissolved in 22 ml of acetone, and 0.79 g of 1,1,3-trichloropropene, 1.3 g of potassium carbonate and 0.27 g of sodium iodide were added. The mixture was stirred at room temperature for 20 hours (monitored by TLC). The reaction mixture was then concentrated using a rotary evaporator, and the resulting crude product was subjected to chromatographic purification. Yield: 2.62 g (95%)

¹H-NMR (CDCl₃): δ=2.35 (quint., 2H); 4.12 (t, 2H); 4.58 (d, 2H); 4.62 (t, 2H); 6.10 (t, 1H); 6.81 (d, 1H); 6.92 (d, 1H); 7.20 (d, 1H); 7.78 (dd, 1H); 8.43 (br. s, 1H).

Step 5: 1-chloro-3-(2-chlorophenylethynyl)-5-(3,3-dichloroprop-2-enyloxy)-2-[3-(5-trifluoromethylpyrid-2-yloxy)propyloxy]benzene Under an atmosphere of protective gas, 0.1 g of 3-chloro-5-(3,3-dichloroprop-2-enyloxy)-1-iodo-2-[3-(5-trifluoromethylpyrid-2-yloxy)propyloxy]benzene, 0.03 g of 1-chloro-2-ethynylbenzene and 0.003 g of copper(I) iodide were dissolved in 1 ml of triethylamine. 0.005 g of bis(triphenylphosphine)palladium(II) chloride was added, and the mixture was stirred at 70° C. for 1 hour. The mixture was then allowed to cool and concentrated under reduced pressure, and the resulting residue was subjected to chromatographic purification. Yield: 0.085 g (84%)

¹H-NMR (CDCl₃): δ=2.35 (quint., 2H); 4.31 (t, 2H); 4.61 (m, 4H); 6.14 (t, 1H); 6.73 (d, 1H); 6.95 (m, 2H); 7.2–7.3 (m, 2H); 7.40 (m, 1H); 7.55 (m, 1H); 7.70 (dd, 1H); 8.36 (br. s, 1H).

Example E 1-chloro-5-(3,3-dichloroprop-2-enyloxy)-3-(2Δ-oxazolin-2-yl)-2-[3-(5-trifluoromethylpyrid-2-yloxy)propyloxy]benzene (No. 738)

Step 1: 3-chloro-5-(3,3-dichloroprop-2-enyloxy)-2-[3-(5-trifluoromethylpyrid-2-yloxy)-propyloxy]benzoic acid 1 g of methyl 3-chloro-5-(3,3-dichloroprop-2-enyloxy)-2-[3-(5-trifluoromethylpyrid-2-yloxy)propyloxy]benzoate was dissolved in 20 ml of tetrahydrofuran and 10 ml of methanol, and 2.6 ml of 2N aqueous sodium hydroxide solution were added. After one hour of stirring at room temperature, 2.6 ml of 2N hydrochloric acid were added, and the reaction mixture was concentrated under reduced pressure. Saturated sodium chloride solution and ethyl acetate were added to the residue, and the mixture was shaken. The ethyl acetate phase was isolated, dried and concentrated. The resulting crude product was purified chromatographically. Yield: 0.91 g (94%)

¹H-NMR (CDCl₃): δ=2.39 (m, 2H); 4.32 (t, 2H); 4.62 (m, 4H); 6.16 (t, 1H); 6.83 (d, 1H); 7.18 (d, 1H); 7.52 (d, 1H); 7.78 (dd, 1H); 8.42 (br. s, 1H).

Step 2: N-(2-hydroxyethyl)-3-chloro-5-(3,3-dichloroprop-2-enyloxy)-2-[3-(5-trifluoromethylpyrid-2-yloxy)propyloxy]benzamide (No. 33)

0.2 g of 3-chloro-5-(3,3-dichloroprop-2-enyloxy)-2-[3-(5-trifluoromethylpyrid-2-yloxy)-propyloxy]benzoic acid and 0.065 g of carbonyldiimidazole were allowed to react at room temperature in 4 ml of anhydrous toluene for 1.5 hours. 0.027 g of 2-amino-ethanol was then added, and the mixture was stirred at room temperature for another hour. The reaction mixture was concentrated under reduced pressure and purified by column chromatography. Yield: 0.159 g (73%)

¹H-NMR (CDCl₃): δ=2.36 (m, 2H); 3.23 (br. s, 1H); 3.60 (m, 2H); 3.82 (m, 2H); 4.13 (t, 2H); 4.60 (t, 4H); 4.63 (d, 2H); 6.15 (t, 1H); 6.82 (d, 1H); 7.06 (d, 1H); 7.28 (d, 1H); 7.79 (dd, 1H); 8.20 (br. m, 1H); 8.42 (br. s, 1H).

Step 3: 1-chloro-5-(3,3-dichloroprop-2-enyloxy)-3-(2Δ-oxazolin-2-yl)-2-[3-(5-trifluoromethylpyrid-2-yloxy)propyloxy]benzene 0.099 g of N-(2-hydroxyethyl)-3-chloro-5-(3,3-dichloroprop-2-enyloxy)-2-[3-(5-trifluoromethylpyrid-2-yloxy)propyloxy]benzamide was dissolved in 1 ml of anhydrous toluene, and 0.065 g of (methoxycarbonylsulfamoyl)triethylammonium N-betaine was added. The mixture was stirred at 50° C. for 1.5 hours. The reaction mixture was then allowed to cool, ethyl acetate and water were added and the mixture was shaken. The ethyl acetate phase was isolated, dried and concentrated under reduced pressure. The crude product was purified chromatographically. Yield: 0.018 g (20%)

¹H-NMR (CDCl₃): δ=2.28 (m, 2H); 4.04 (t, 2H); 4.15 (t, 2H); 4.40 (t, 2H); 4.60 (m, 4H); 6.14 (t, 1H); 6.80 (d, 1H); 7.03 (d, 1H); 7.20 (d, 1H); 7.76 (dd, 1H); 8.42 (br. s, 1H).

Example F 1-chloro-5-(3,3-dichloroprop-2-enyloxy)-3-(1-methylpyrazol-3-yl)-2-[3-(5-trifluoromethylpyrid-2-yloxy)propyloxy]benzene (No. 950)

0.3 g of 3-acetyl-1-chloro-5-(3,3-dichloroprop-2-enyloxy)-2-[3-(5-trifluoromethylpyrid-2-yloxy)propyloxy]benzene and 128 μl of N,N-dimethylformamide dimethyl acetal were stirred at 95° C. for 5 hours. The reaction mixture was then concentrated under high vacuum (<1 mbar) and the residue was dissolved in 4 ml of ethanol. 0.015 g of methylhydrazine was added, and the mixture was heated under reflux for 2 hours. After cooling, the mixture was concentrated and the resulting crude product was purified chromatographically. Yield: 0.212 g (66%)

¹H-NMR (CDCl₃): δ=1.98 (m, 2H); 3.73 (t, 2H); 3.77 (s, 3H); 4.34 (t, 2H); 4.62 (d, 2H); 6.15 (t, 1H); 6.27 (m, 1H); 6.73 (d, 1H); 6.76 (d, 1H); 7.01 (d, 1H); 7.42 (m, 1H); 7.78 (dd, 1H); 8.41 (br. s, 1H).

The product was contaminated with less than 10% of the regioisomeric structure 1-chloro-5-(3,3-dichloroprop-2-enyloxy)-3-(1-methylpyrazol-5-yl)-2-[3-(5-trifluoromethylpyrid-2-yloxy)propyloxy]benzene.

The compounds listed in Tables 1 to 11 below can be prepared in an analogous manner. Here, Me is methyl, Et is ethyl, Ph is phenyl, Py is pyridine and m.p. means melting point.

TABLE 1
| Number | Skeleton |
|---|---|
| 1 | 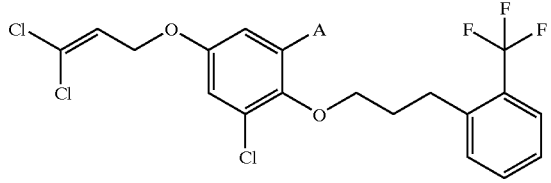 |
| 2 | 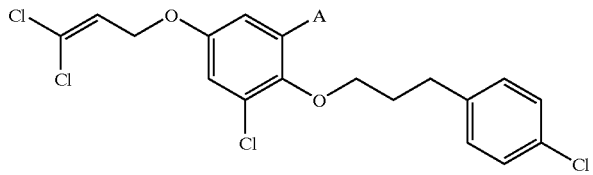 |
| 3 | 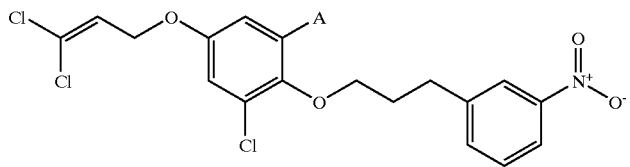 |
| 4 | 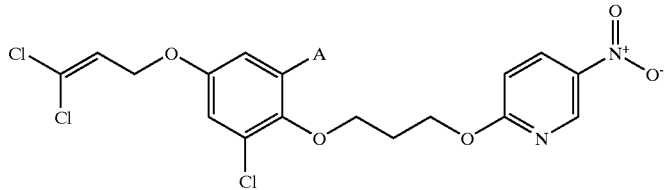 |
| 5 | 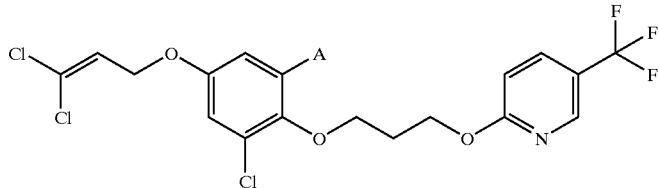 |
| 6 | 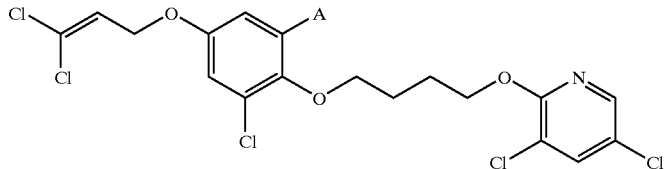 |
| 7 | 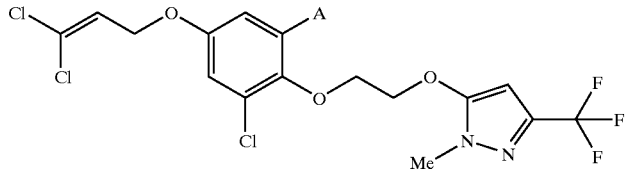 |
| 8 | 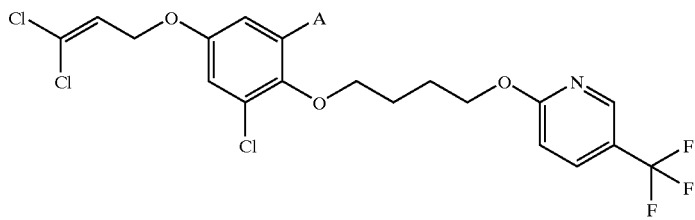 |

TABLE 1-continued
| Number | Skeleton |
|---|---|
| 9 | 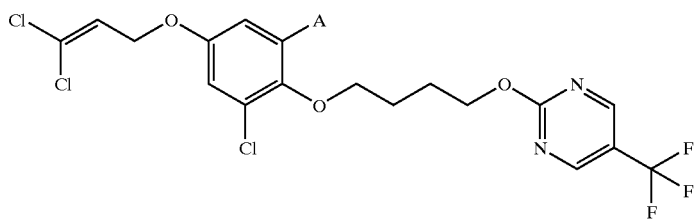 |
| 10 | 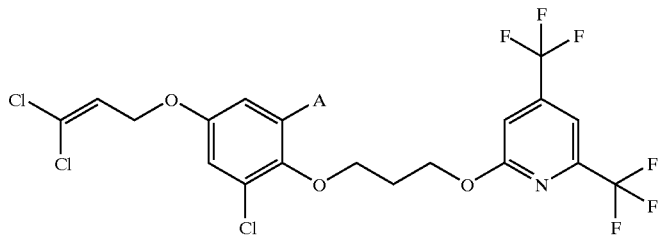 |
| 11 | 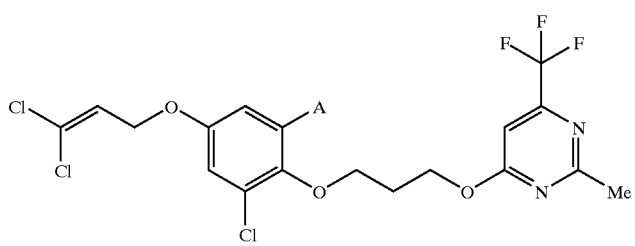 |
| 12 | 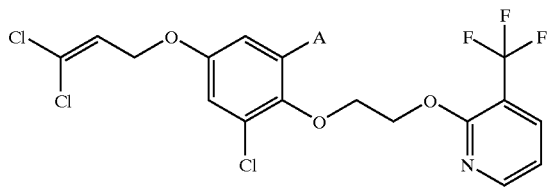 |
| 13 | 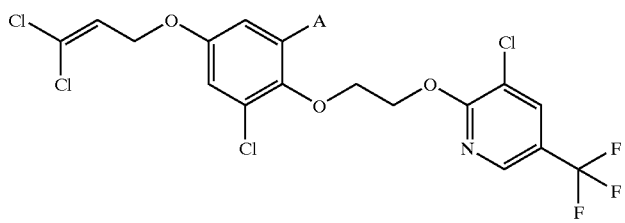 |
| 14 | 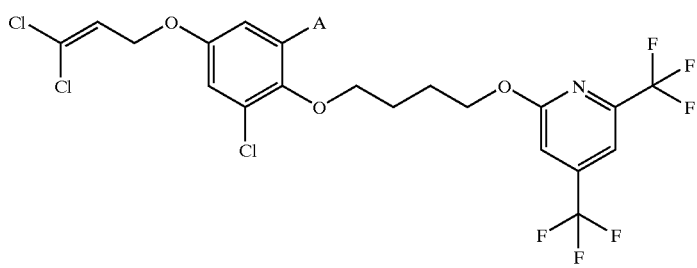 |

TABLE 1-continued
| Number | Skeleton |
|---|---|
| 15 | 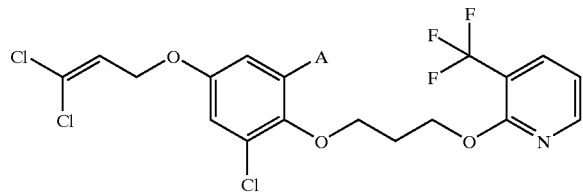 |
| 16 | 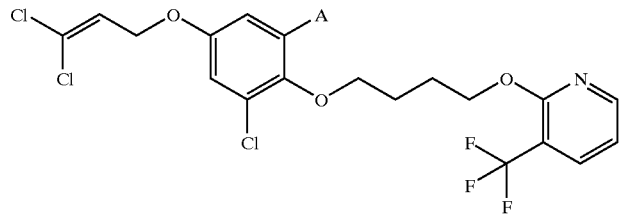 |
| 17 | 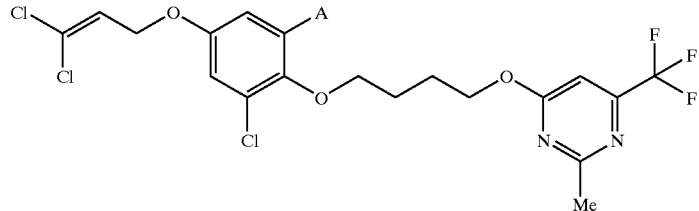 |
| 18 | 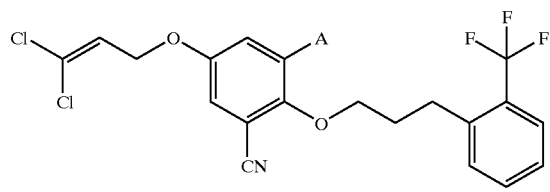 |
| 19 | 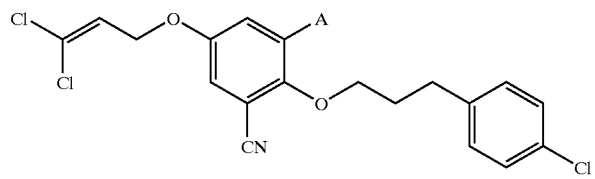 |
| 20 | 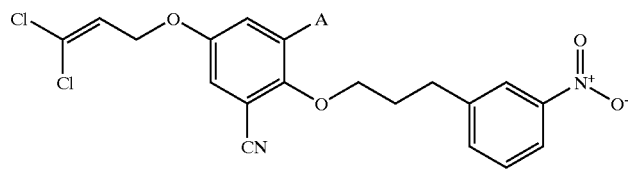 |
| 21 | 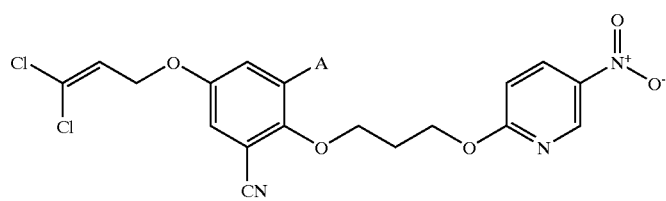 |

TABLE 1-continued

| Number | Skeleton |
|---|---|
| 22 | |
| 23 | |
| 24 | |
| 25 | |
| 26 | |
| 27 | |
| 28 | |

TABLE 1-continued
| Number | Skeleton |
|---|---|
| 29 | 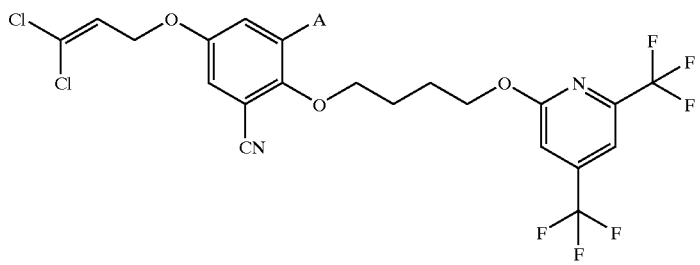 |
| 30 | 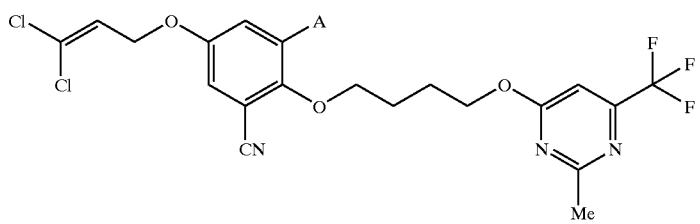 |
| 31 | 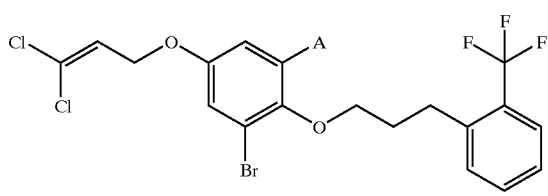 |
| 32 | 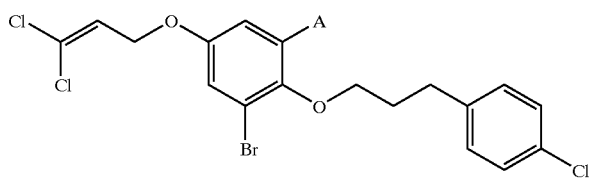 |
| 33 | 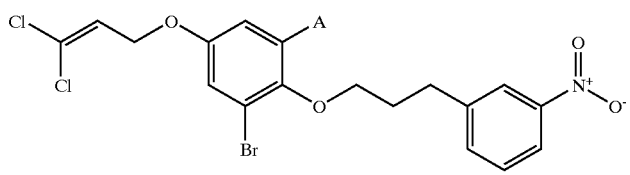 |
| 34 | 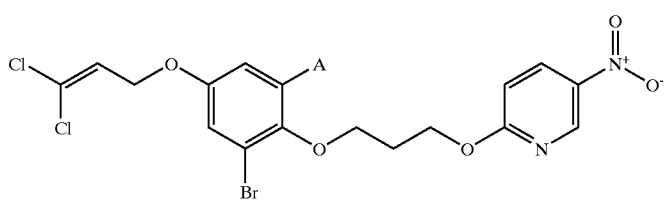 |
| 35 | 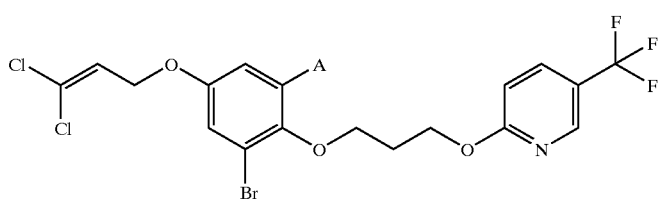 |

TABLE 1-continued
| Number | Skeleton |
|---|---|
| 36 | 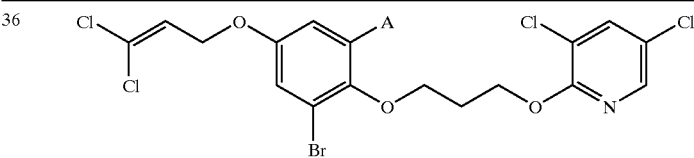 |
| 37 | 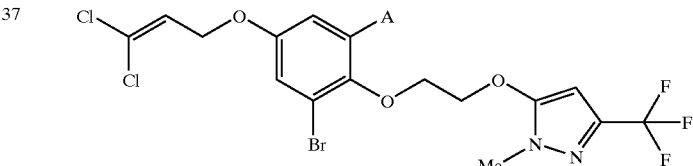 |
| 38 | 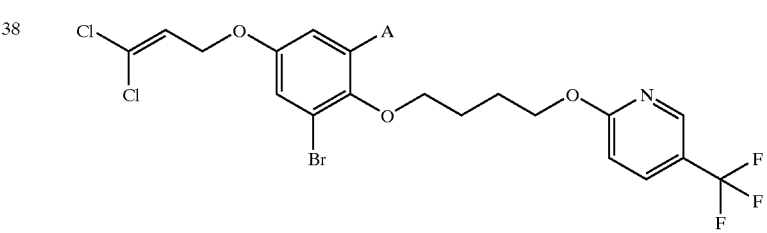 |
| 39 | 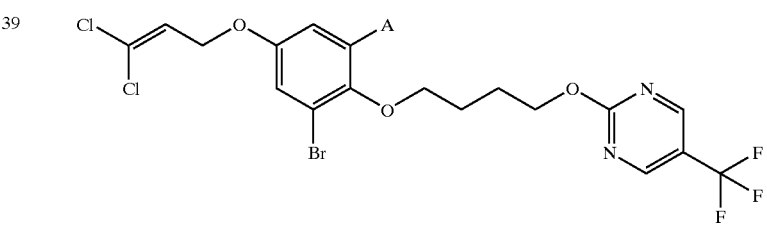 |
| 40 | 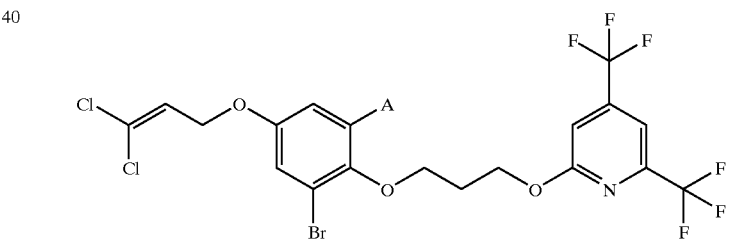 |
| 41 | 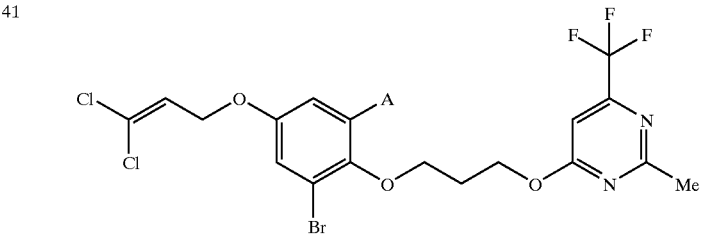 |
| 42 | 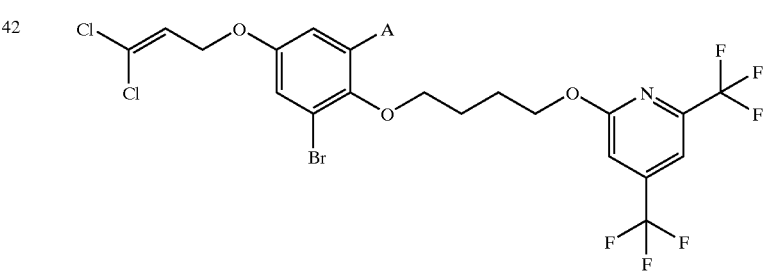 |

TABLE 1-continued
| Number | Skeleton |
|---|---|
| 43 | 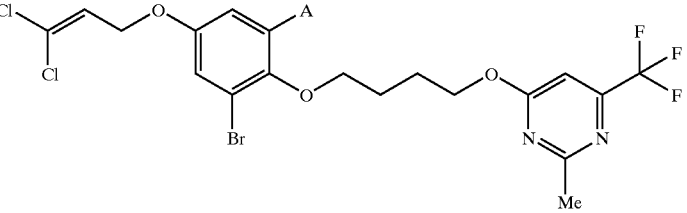 |
| 44 | 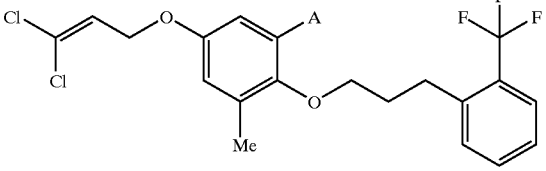 |
| 45 | 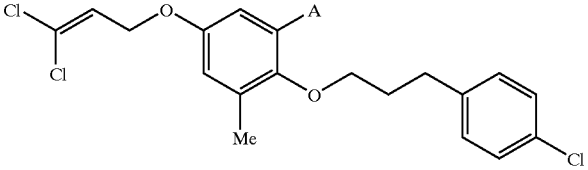 |
| 46 | 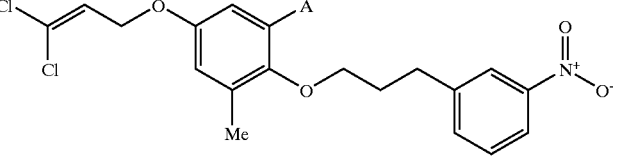 |
| 47 | 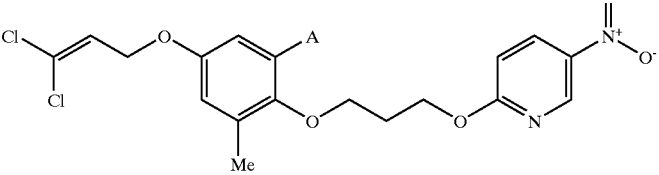 |
| 48 | 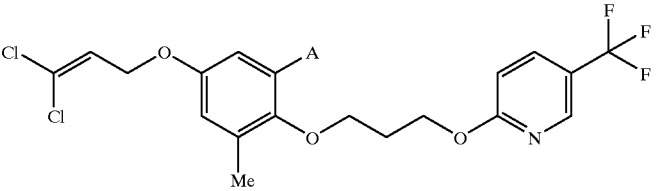 |
| 49 | 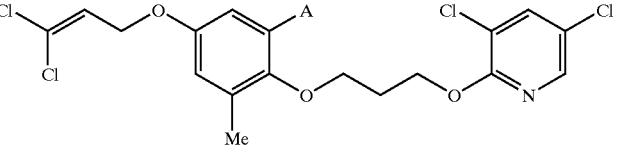 |
| 50 | 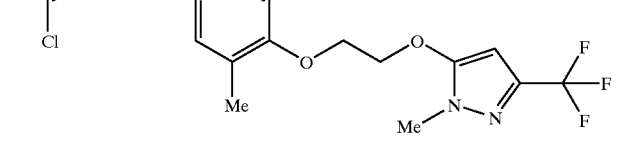 |

TABLE 1-continued
| Number | Skeleton |
|---|---|
| 51 | |
| 52 | |
| 53 | |
| 54 | |
| 55 | |
| 56 | |
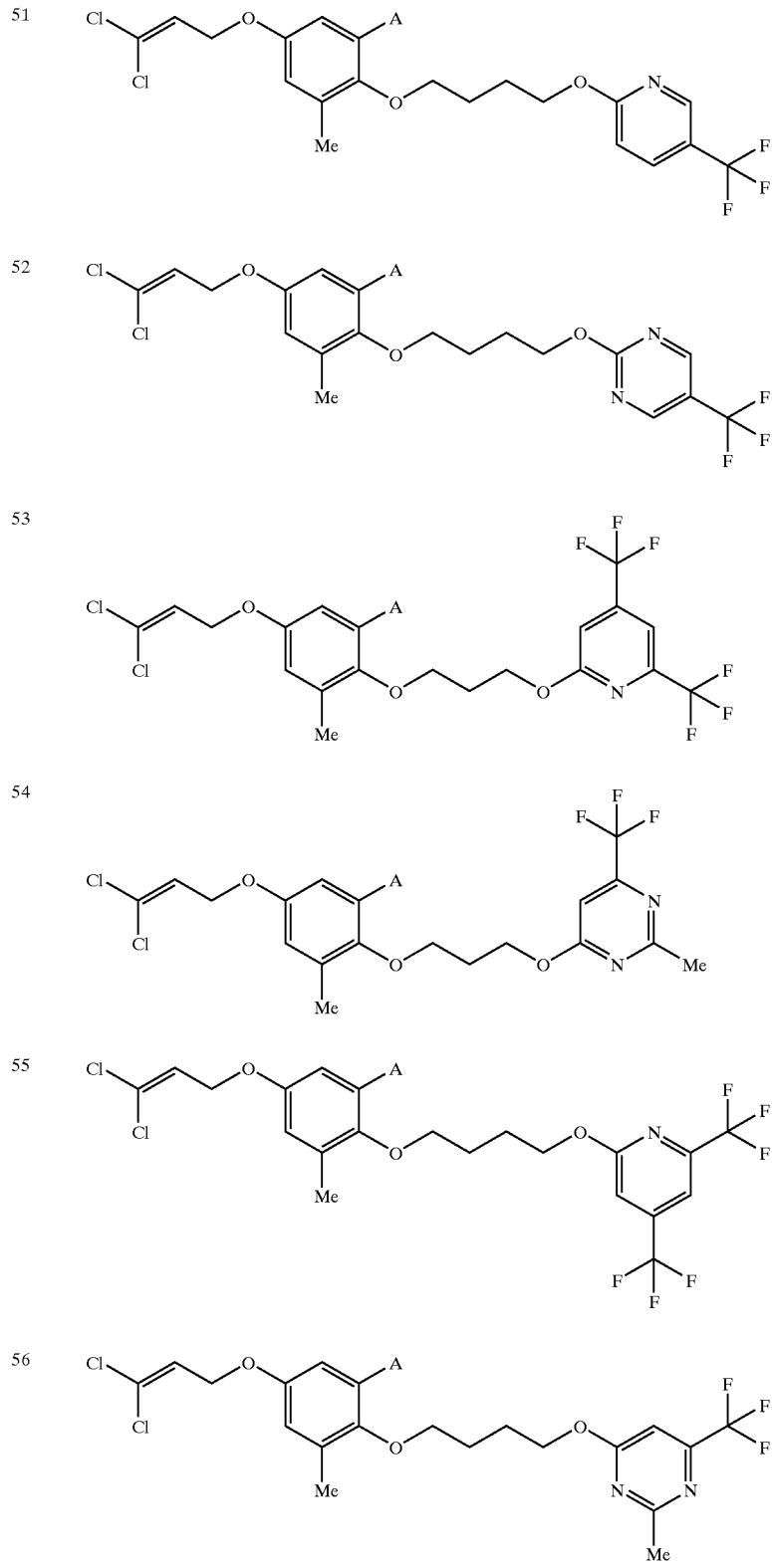

TABLE 2

$$A = \underset{R}{\overset{X}{\|}}{\bigg\backslash}$$

| No. | Skeleton | X | R | m.p. |
|---|---|---|---|---|
| 1 | 1 | O | CH₂CF₃ | |
| 2 | 1 | O | Et | |
| 3 | 1 | O | Me | |
| 4 | 2 | O | CH₂CF₃ | |
| 5 | 2 | O | Et | |
| 6 | 2 | O | Me | oil |
| 7 | 2 | O | OMe | oil |
| 8 | 3 | O | CH₂CF₃ | |
| 9 | 3 | O | Et | |
| 10 | 3 | O | Me | |
| 11 | 4 | O | CH₂CF₃ | |
| 12 | 4 | O | Et | |
| 13 | 4 | O | Me | |
| 14 | 5 | O | ![3-fluoro-N-methylaniline group] | 68° C. |
| 15 | 5 | O | MeO-N=C(iPr)-NH₂ (methoxyimino isopropyl amidine) | oil |
| 16 | 5 | O | MeO-N=C(Et)-NH₂ | oil |
| 17 | 5 | O | MeO-N=C(cyclopentyl)-NH₂ | oil |
| 18 | 5 | O | MeO-N=C(OEt)-NH₂ | oil |
| 19 | 5 | O | MeO-N=C(cyclohexyl)-NH₂ | oil |
| 20 | 5 | O | 1-imidazolyl | oil |
| 21 | 5 | O | CH=CH—NMe₂ | syrup |
| 22 | 5 | O | CH₂CF₃ | |
| 23 | 5 | O | CH₂CH₂CH₃ | |
| 24 | 5 | O | CHBr₂ | oil |
| 25 | 5 | O | Et | oil |
| 26 | 5 | O | H | oil |
| 27 | 5 | O | Me | oil |
| 28 | 5 | N—OH | Me | 66° C. |
| 29 | 5 | N—OMe | Me | oil |
| 30 | 5 | O | NH₂ | 91° C. |
| 31 | 5 | S | NH₂ | 110° C. |
| 32 | 5 | O | NHCH(Me)CH₂OH | 106° C. |
| 33 | 5 | O | NHCH₂CH₂OH | 78° C. |
| 34 | 5 | O | NHEt | 73° C. |
| 35 | 5 | O | NHMe—OMe | oil |
| 36 | 5 | O | NMe₂ | oil |
| 37 | 5 | O | O—CH(Me)₂ | glass-like |

TABLE 2-continued

A = $\overset{X}{\underset{R}{\text{C}}}$

| No. | Skeleton | X | R | m.p. |
|---|---|---|---|---|
| 38 | 5 | O | O—CH$_2$CH$_2$CH$_3$ | oil |
| 39 | 5 | O | OMe | oil |
| 40 | 5 | O | O-phenyl | oil |
| 41 | 6 | O | CH$_2$CF$_3$ | |
| 42 | 6 | O | Et | |
| 43 | 6 | O | Me | oil |
| 44 | 6 | N—OH | Me | 129° C. |
| 45 | 6 | N—OMe | Me | oil |
| 46 | 6 | O | Me | |
| 47 | 7 | O | CH$_2$CF$_3$ | |
| 48 | 7 | O | Et | |
| 49 | 7 | O | Me | |
| 50 | 8 | O | MeO–N=C(NH$_2$)–CH(Me)$_2$ | oil |
| 51 | 8 | O | MeO–N=C(NH$_2$)–CH$_2$Me | oil |
| 52 | 8 | O | MeO–N=C(NH$_2$)–O–CH$_2$Me | oil |
| 53 | 8 | O | MeO–N=C(NH$_2$)–cyclopentyl | oil |
| 54 | 8 | O | MeO–N=C(NH$_2$)–O–CH$_2$Me | oil |
| 55 | 8 | O | MeO–N=C(NH$_2$)–cyclohexyl | oil |
| 56 | 8 | O | CH$_2$CF$_3$ | |
| 57 | 8 | O | Et | |
| 58 | 8 | O | H | |
| 59 | 8 | O | Me | oil |
| 60 | 8 | O | OMe | oil |
| 61 | 9 | O | CH$_2$CF$_3$ | |
| 62 | 9 | O | Et | |
| 63 | 9 | O | Me | |
| 64 | 10 | O | CH$_2$CF$_3$ | |
| 65 | 10 | O | Et | |
| 66 | 10 | O | Me | |
| 67 | 11 | O | CH$_2$CF$_3$ | |
| 68 | 11 | O | Et | |
| 69 | 11 | O | Me | |
| 70 | 11 | O | OMe | 32° C.–35° C. |
| 71 | 12 | O | CH$_2$CF$_3$ | |
| 72 | 12 | O | Et | |
| 73 | 12 | O | Me | 82° C. |
| 74 | 13 | O | CH$_2$CF$_3$ | |
| 75 | 13 | O | Et | |

TABLE 2-continued

A = 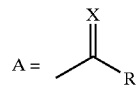

| No. | Skeleton | X | R | m.p. |
|---|---|---|---|---|
| 76 | 13 | O | Me | 110° C. |
| 77 | 14 | O | CH$_2$CF$_3$ | |
| 78 | 14 | O | Et | |
| 79 | 14 | O | Me | |
| 80 | 15 | O | CH$_2$CF$_3$ | |
| 81 | 15 | O | Et | |
| 82 | 15 | O | Me | oil |
| 83 | 15 | N—OH | Me | oil |
| 84 | 15 | N—OMe | Me | oil |
| 85 | 15 | N—OCH$_2$CH=CH$_2$ | Me | oil |
| 86 | 15 | O | OMe | oil |
| 87 | 16 | O | CH$_2$CF$_3$ | |
| 88 | 16 | O | Et | |
| 89 | 16 | O | Me | oil |
| 90 | 16 | N—OH | Me | oil |
| 91 | 16 | N—OMe | Me | oil |
| 92 | 16 | N—OCH$_2$CH=CH$_2$ | Me | oil |
| 93 | 16 | O | OMe | oil |
| 94 | 17 | O | CH$_2$CF$_3$ | |
| 95 | 17 | O | Et | |
| 96 | 17 | O | Me | |
| 97 | 17 | O | OMe | oil |
| 98 | 18 | O | CH$_2$CF$_3$ | |
| 99 | 18 | O | Et | |
| 100 | 18 | O | Me | |
| 101 | 19 | O | CH$_2$CF$_3$ | |
| 102 | 19 | O | Et | |
| 103 | 19 | O | Me | |
| 104 | 20 | O | CH$_2$CF$_3$ | |
| 105 | 20 | O | Et | |
| 106 | 20 | O | Me | |
| 107 | 21 | O | Me | |
| 108 | 22 | O | CH$_2$CF$_3$ | |
| 109 | 22 | O | Et | |
| 110 | 22 | O | H | |
| 111 | 22 | O | Me | |
| 112 | 23 | O | CH$_2$CF$_3$ | |
| 113 | 23 | O | Et | |
| 114 | 23 | O | Me | |
| 115 | 24 | O | CH$_2$CF$_3$ | |
| 116 | 24 | O | Et | |
| 117 | 24 | O | Me | |
| 118 | 25 | O | CH$_2$CF$_3$ | |
| 119 | 25 | O | Et | |
| 120 | 25 | O | H | |
| 121 | 25 | O | Me | |
| 122 | 26 | O | CH$_2$CF$_3$ | |
| 123 | 26 | O | Et | |
| 124 | 26 | O | Me | |
| 125 | 27 | O | CH$_2$CF$_3$ | |
| 126 | 27 | O | Et | |
| 127 | 27 | O | Me | |
| 128 | 28 | O | CH$_2$CF$_3$ | |
| 129 | 28 | O | Et | |
| 130 | 28 | O | Me | |
| 131 | 29 | O | CH$_2$CF$_3$ | |
| 132 | 29 | O | Et | |
| 133 | 29 | O | Me | |
| 134 | 30 | O | CH$_2$CF$_3$ | |
| 135 | 30 | O | Et | |
| 136 | 30 | O | Me | |
| 137 | 31 | O | CH$_2$CF$_3$ | |
| 138 | 31 | O | Et | |
| 139 | 31 | O | Me | |
| 140 | 32 | O | CH$_2$CF$_3$ | |
| 141 | 32 | O | Et | |
| 142 | 32 | O | Me | |
| 143 | 33 | O | CH$_2$CF$_3$ | |
| 144 | 33 | O | Et | |
| 145 | 33 | O | Me | |
| 146 | 34 | O | CH$_2$CF$_3$ | |

TABLE 2-continued

A = (structure with X double-bonded and R single-bonded to central carbon)

| No. | Skeleton | X | R | m.p. |
|---|---|---|---|---|
| 147 | 34 | O | Et | |
| 148 | 34 | O | Me | |
| 149 | 35 | O | CH$_2$CF$_3$ | |
| 150 | 35 | O | Et | |
| 151 | 35 | O | Me | |
| 152 | 36 | O | CH$_2$CF$_3$ | |
| 153 | 36 | O | Et | |
| 154 | 36 | O | Me | |
| 155 | 37 | O | CH$_2$CF$_3$ | |
| 156 | 37 | O | Et | |
| 157 | 37 | O | Me | |
| 158 | 38 | O | CH$_2$CF$_3$ | |
| 159 | 38 | O | Et | |
| 160 | 38 | O | Me | |
| 161 | 39 | O | CH$_2$CF$_3$ | |
| 162 | 39 | O | Et | |
| 163 | 39 | O | Me | |
| 164 | 40 | O | CH$_2$CF$_3$ | |
| 165 | 40 | O | Et | |
| 166 | 40 | O | Me | |
| 167 | 41 | O | CH$_2$CF$_3$ | |
| 168 | 41 | O | Et | |
| 169 | 41 | O | Me | |
| 170 | 42 | O | CH$_2$CF$_3$ | |
| 171 | 42 | O | Et | |
| 172 | 42 | O | Me | |
| 173 | 43 | O | CH$_2$CF$_3$ | |
| 174 | 43 | O | Et | |
| 175 | 43 | O | Me | |
| 176 | 44 | O | CH$_2$CF$_3$ | |
| 177 | 44 | O | Et | |
| 178 | 44 | O | Me | |
| 179 | 45 | O | CH$_2$CF$_3$ | |
| 180 | 45 | O | Et | |
| 181 | 45 | O | Me | |
| 182 | 46 | O | CH$_2$CF$_3$ | |
| 183 | 46 | O | Et | |
| 184 | 46 | O | Me | |
| 185 | 47 | O | CH$_2$CF$_3$ | |
| 186 | 47 | O | Et | |
| 187 | 47 | O | Me | |
| 188 | 48 | O | CH$_2$CF$_3$ | |
| 189 | 48 | O | Et | |
| 190 | 48 | O | H | |
| 191 | 48 | O | Me | |
| 192 | 49 | O | CH$_2$CF$_3$ | |
| 193 | 49 | O | Et | |
| 194 | 49 | O | Me | |
| 195 | 50 | O | CH$_2$CF$_3$ | |
| 196 | 50 | O | Ft | |
| 197 | 50 | O | Me | |
| 198 | 51 | O | CH$_2$CF$_3$ | |
| 199 | 51 | O | Et | |
| 200 | 51 | O | H | |
| 201 | 51 | O | Me | |
| 202 | 52 | O | CH$_2$CF$_3$ | |
| 203 | 52 | O | Et | |
| 204 | 52 | O | Me | |
| 205 | 53 | O | CH$_2$CF$_3$ | |
| 206 | 53 | O | Et | |
| 207 | 53 | O | Me | |
| 208 | 54 | O | CH$_2$CF$_3$ | |
| 209 | 54 | O | Ft | |
| 210 | 54 | O | Me | |
| 211 | 55 | O | CH$_2$CF$_3$ | |
| 212 | 55 | O | Ft | |
| 213 | 55 | O | Me | |
| 214 | 56 | O | CH$_2$CF$_3$ | |
| 215 | 56 | O | Ft | |
| 216 | 56 | O | Me | |
| 1236 | 5 | O | OCH$_2$CF$_3$ | |

TABLE 2-continued

A = (structure with X double-bonded to C, and R substituent)

| No. | Skeleton | X | R | m.p. |
|---|---|---|---|---|
| 1237 | 5 | O | O(3-(OCF$_2$CF$_2$H)—Ph) | |
| 1238 | 5 | O | O(4-F—Ph) | |
| 1239 | 5 | O | O(3-F—Ph) | |
| 1240 | 5 | O | O(3-CF$_3$—Ph) | |
| 1241 | 5 | O | SCH$_2$CF$_3$ | |
| 1242 | 5 | O | O(4-OCF$_3$—Ph) | |
| 1243 | 5 | O | SPh | |
| 1244 | 5 | O | S(3-F—Ph) | |
| 1245 | 5 | O | S(4-CF$_3$—Ph) | |
| 1246 | 5 | O | NHNH(2,6-Cl$_2$—4-CF$_3$—Ph) | |
| 1247 | 5 | O | O(C$_2$H$_4$(2,6-Cl$_2$—4-CF$_3$—Ph) | |
| 1248 | 5 | N | NH(2,6-Cl$_2$—4-CF$_3$—Ph)) | |

TABLE 3

A = (alkynyl group with R substituent)

| No. | Skeleton | R | m.p. |
|---|---|---|---|
| 217 | 1 | H | |
| 218 | 1 | Me | |
| 219 | 2 | H | |
| 220 | 2 | Me | |
| 221 | 3 | H | |
| 222 | 3 | Me | |
| 223 | 4 | H | |
| 224 | 4 | Me | |
| 225 | 5 | 1-hexyl | oil |
| 226 | 5 | 2-chlorophenyl | oil |
| 227 | 5 | CH$_2$OH | 89° C. |
| 228 | 5 | CH$_2$OMe | oil |
| 229 | 5 | H | oil |
| 230 | 5 | Me | |
| 231 | 5 | SiMe$_3$ | oil |
| 232 | 6 | H | |
| 233 | 6 | Me | |
| 234 | 7 | H | |
| 235 | 7 | Me | |
| 236 | 8 | H | |
| 237 | 8 | Me | |
| 238 | 9 | H | |
| 239 | 9 | Me | |
| 240 | 10 | H | |
| 241 | 10 | Me | |
| 242 | 11 | H | |
| 243 | 11 | Me | |
| 244 | 12 | H | |
| 245 | 12 | Me | |
| 246 | 13 | H | |
| 247 | 13 | Me | |
| 248 | 14 | H | |
| 249 | 14 | Me | |
| 250 | 15 | H | |
| 251 | 15 | Me | |
| 252 | 16 | H | |
| 253 | 16 | Me | |
| 254 | 17 | H | |
| 255 | 17 | Me | |
| 256 | 18 | H | |
| 257 | 18 | Me | |
| 258 | 19 | H | |
| 259 | 19 | Me | |
| 260 | 20 | H | |
| 261 | 20 | Me | |
| 262 | 22 | H | |
| 263 | 22 | Me | |
| 264 | 23 | H | |
| 265 | 23 | Me | |
| 266 | 24 | H | |
| 267 | 24 | Me | |
| 268 | 25 | H | |
| 269 | 25 | Me | |
| 270 | 26 | H | |
| 271 | 26 | Me | |
| 272 | 27 | H | |
| 273 | 27 | Me | |
| 274 | 28 | H | |
| 275 | 28 | Me | |
| 276 | 29 | H | |
| 277 | 29 | Me | |
| 278 | 30 | H | |
| 279 | 30 | Me | |
| 280 | 31 | H | |
| 281 | 31 | Me | |
| 282 | 32 | H | |
| 283 | 32 | Me | |
| 284 | 33 | H | |
| 285 | 33 | Me | |
| 286 | 34 | H | |
| 287 | 34 | Me | |
| 288 | 35 | H | |
| 289 | 35 | Me | |
| 290 | 36 | H | |
| 291 | 36 | Me | |
| 292 | 37 | H | |
| 293 | 37 | Me | |
| 294 | 38 | H | |
| 295 | 38 | Me | |
| 296 | 39 | H | |
| 297 | 39 | Me | |
| 298 | 40 | H | |
| 299 | 40 | Me | |
| 300 | 41 | H | |
| 301 | 41 | Me | |
| 302 | 42 | H | |
| 303 | 42 | Me | |
| 304 | 43 | H | |
| 305 | 43 | Me | |
| 306 | 44 | H | |
| 307 | 44 | Me | |
| 308 | 45 | H | |

TABLE 3-continued

| No. | Skeleton | R | m.p. |
|---|---|---|---|
| 309 | 45 | Me | |
| 310 | 46 | H | |
| 311 | 46 | Me | |
| 312 | 47 | H | |
| 313 | 47 | Me | |
| 314 | 48 | H | |
| 315 | 48 | Me | |
| 316 | 49 | H | |
| 317 | 49 | Me | |
| 318 | 50 | H | |
| 319 | 50 | Me | |
| 320 | 51 | H | |
| 321 | 51 | Me | |
| 322 | 52 | H | |
| 323 | 52 | Me | |
| 324 | 53 | H | |
| 325 | 53 | Me | |
| 326 | 54 | H | |
| 327 | 54 | Me | |
| 328 | 55 | H | |
| 329 | 55 | Me | |
| 330 | 56 | H | |
| 331 | 56 | Me | |

TABLE 4

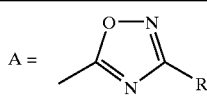

| No. | Skeleton | R | m.p. |
|---|---|---|---|
| 332 | 1 | $CH_2SMe$ | |
| 333 | 1 | Et | |
| 334 | 1 | Me | |
| 335 | 2 | $CH_2SMe$ | |
| 336 | 2 | Et | |
| 337 | 2 | Me | |
| 338 | 3 | $CH_2SMe$ | |
| 339 | 3 | Et | |
| 340 | 3 | Me | |
| 341 | 4 | $CH_2SMe$ | |
| 342 | 4 | Et | |
| 343 | 4 | Me | |
| 344 | 5 | $CH(Me)_2$ | |
| 345 | 5 | $CH_2CF_3$ | |
| 346 | 5 | $CH_2CH_2CH_2OMe$ | |
| 347 | 5 | $CH_2CH_2CH_3$ | oil |
| 348 | 5 | $CH_2CH_2OEt$ | oil |
| 349 | 5 | $CH_2CO_2Me$ | |
| 350 | 5 | $CH_2N(Me)_2$ | |
| 351 | 5 | $CH_2SMe$ | oil |
| 352 | 5 | $CH_2SPh$ | |
| 353 | 5 | $CHMe_2$ | oil |
| 354 | 5 | cyclohexyl | oil |
| 355 | 5 | cyclopentyl | oil |
| 356 | 5 | Et | oil |
| 357 | 5 | Me | oil |
| 358 | 6 | $CH_2SMe$ | |
| 359 | 6 | Et | |
| 360 | 6 | Me | |
| 361 | 7 | $CH(Me)_2$ | |
| 362 | 7 | $CH_2CF_3$ | |
| 363 | 7 | $CH_2CH_2CH_2OMe$ | |
| 364 | 7 | $CH_2CO_2Me$ | |
| 365 | 7 | $CH_2N(Me)_2$ | |
| 366 | 7 | $CH_2SMe$ | |
| 367 | 7 | $CH_2SPh$ | |

TABLE 4-continued

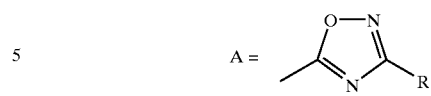

| No. | Skeleton | R | m.p. |
|---|---|---|---|
| 368 | 7 | Et | |
| 369 | 7 | Me | |
| 370 | 8 | $CH(Me)_2$ | |
| 371 | 8 | $CH_2CF_3$ | |
| 372 | 8 | $CH_2CH_2CH_2OMe$ | |
| 373 | 8 | $CH_2CH_2CH_3$ | oil |
| 374 | 8 | $CH_2CH_2OEt$ | oil |
| 375 | 8 | CH2CH3 | oil |
| 376 | 8 | $CH_2CO_2Me$ | |
| 377 | 8 | $CH_2N(Me)_2$ | |
| 378 | 8 | $CH_2SMe$ | |
| 379 | 8 | $CH_2SPh$ | |
| 380 | 8 | $CHMe_2$ | oil |
| 381 | 8 | cyclohexyl | oil |
| 382 | 8 | cyclopentyl | oil |
| 383 | 8 | Me | |
| 384 | 9 | $CH_2SMe$ | |
| 385 | 9 | Et | |
| 386 | 9 | Me | |
| 387 | 10 | $CH_2SMe$ | |
| 388 | 10 | Et | |
| 389 | 10 | Me | |
| 390 | 11 | $CH_2SMe$ | |
| 391 | 11 | Et | |
| 392 | 11 | Me | |
| 393 | 12 | $CH_2SMe$ | |
| 394 | 12 | Et | |
| 395 | 12 | Me | |
| 396 | 13 | $CH_2SMe$ | |
| 397 | 13 | Et | |
| 398 | 13 | Me | |
| 399 | 14 | $CH_2SMe$ | |
| 400 | 14 | Et | |
| 401 | 14 | Me | |
| 402 | 15 | $CH_2SMe$ | |
| 403 | 15 | Et | |
| 404 | 15 | Me | |
| 405 | 16 | $CH_2SMe$ | |
| 406 | 16 | Et | |
| 407 | 16 | Me | |
| 408 | 17 | $CH_2SMe$ | |
| 409 | 17 | Et | |
| 410 | 17 | Me | |
| 411 | 18 | $CH_2SMe$ | |
| 412 | 18 | Et | |
| 413 | 18 | Me | |
| 414 | 19 | $CH_2SMe$ | |
| 415 | 19 | Et | |
| 416 | 19 | Me | |
| 417 | 20 | $CH_2SMe$ | |
| 418 | 20 | Et | |
| 419 | 20 | Me | |
| 420 | 21 | $CH_2SMe$ | |
| 421 | 21 | Et | |
| 422 | 21 | Me | |
| 423 | 22 | $CH(Me)_2$ | |
| 424 | 22 | $CH_2CF_3$ | |
| 425 | 22 | $CH_2CH_2CH_2OMe$ | |
| 426 | 22 | $CH_2CO_2Me$ | |
| 427 | 22 | $CH_2N(Me)_2$ | |
| 428 | 22 | $CH_2SMe$ | |
| 429 | 22 | $CH_2SPh$ | |
| 430 | 22 | Et | |
| 431 | 22 | Me | |
| 432 | 23 | $CH_2SMe$ | |
| 433 | 23 | Et | |
| 434 | 23 | Me | |
| 435 | 24 | $CH_2SMe$ | |
| 436 | 24 | Et | |
| 437 | 24 | Me | |
| 438 | 25 | $CH(Me)_2$ | |

TABLE 4-continued

A = (5-methyl-1,2,4-oxadiazol-3-yl with R at 3-position)

| No. | Skeleton | R | m.p. |
|---|---|---|---|
| 439 | 25 | CH₂CF₃ | |
| 440 | 25 | CH₂CH₂CH₂OMe | |
| 441 | 25 | CH₂CO₂Me | |
| 442 | 25 | CH₂N(Me)₂ | |
| 443 | 25 | CH₂SMe | |
| 444 | 25 | CH₂SPh | |
| 445 | 25 | Et | |
| 446 | 25 | Me | |
| 447 | 26 | CH(Me)₂ | |
| 448 | 26 | CH₂CF₃ | |
| 449 | 26 | CH₂CH₂CH₂OMe | |
| 450 | 26 | CH₂CO₂Me | |
| 451 | 26 | CH₂N(Me)₂ | |
| 452 | 26 | CH₂SMe | |
| 453 | 26 | CH₂SPh | |
| 454 | 26 | Et | |
| 455 | 26 | Me | |
| 456 | 27 | CH₂SMe | |
| 457 | 27 | Et | |
| 458 | 27 | Me | |
| 459 | 28 | CH₂SMe | |
| 460 | 28 | Et | |
| 461 | 28 | Me | |
| 462 | 29 | CH₂SMe | |
| 463 | 29 | Et | |
| 464 | 29 | Me | |
| 465 | 30 | CH₂SMe | |
| 466 | 30 | Et | |
| 467 | 30 | Me | |
| 468 | 31 | CH₂SMe | |
| 469 | 31 | Et | |
| 470 | 31 | Me | |
| 471 | 32 | CH₂SMe | |
| 472 | 32 | Et | |
| 473 | 32 | Me | |
| 474 | 33 | CH₂SMe | |
| 475 | 33 | Et | |
| 476 | 33 | Me | |
| 477 | 34 | CH₂SMe | |
| 478 | 34 | Et | |
| 479 | 34 | Me | |
| 480 | 35 | CH(Me)₂ | |
| 481 | 35 | CH₂CF₃ | |
| 482 | 35 | CH₂CH₂CH₂OMe | |
| 483 | 35 | CH₂CO₂Me | |
| 484 | 35 | CH₂N(Me)₂ | |
| 485 | 35 | CH₂SMe | |
| 486 | 35 | CH₂SPh | |
| 487 | 35 | Et | |
| 488 | 35 | Me | |
| 489 | 36 | CH₂SMe | |
| 490 | 36 | Et | |
| 491 | 36 | Me | |
| 492 | 37 | CH₂SMe | |
| 493 | 37 | Et | |
| 494 | 37 | Me | |
| 495 | 38 | CH(Me)₂ | |
| 496 | 38 | CH₂CF₃ | |
| 497 | 38 | CH₂CH₂CH₂OMe | |
| 498 | 38 | CH₂CO₂Me | |
| 499 | 38 | CH₂N(Me)₂ | |
| 500 | 38 | CH₂SMe | |
| 501 | 38 | CH₂SPh | |
| 502 | 38 | Et | |
| 503 | 38 | Me | |
| 504 | 39 | CH₂SMe | |
| 505 | 39 | Et | |
| 506 | 39 | Me | |
| 507 | 40 | CH(Me)₂ | |
| 508 | 40 | CH₂CF₃ | |
| 509 | 40 | CH₂CH₂CH₂OMe | |
| 510 | 40 | CH₂CO₂Me | |
| 511 | 40 | CH₂N(Me)₂ | |
| 512 | 40 | CH₂SMe | |
| 513 | 40 | CH₂SPh | |
| 514 | 40 | Et | |
| 515 | 40 | Me | |
| 516 | 41 | CH₂SMe | |
| 517 | 41 | Et | |
| 518 | 41 | Me | |
| 519 | 42 | CH₂SMe | |
| 520 | 42 | Et | |
| 521 | 42 | Me | |
| 522 | 43 | CH₂SMe | |
| 523 | 43 | Et | |
| 524 | 43 | Me | |
| 525 | 44 | CH₂SMe | |
| 526 | 44 | Et | |
| 527 | 44 | Me | |
| 528 | 45 | CH₂SMe | |
| 529 | 45 | Et | |
| 530 | 45 | Me | |
| 531 | 46 | CH₂SMe | |
| 532 | 46 | Et | |
| 533 | 46 | Me | |
| 534 | 47 | CH₂SMe | |
| 535 | 47 | Et | |
| 536 | 47 | Me | |
| 537 | 48 | CH(Me)₂ | |
| 538 | 48 | CH₂CF₃ | |
| 539 | 48 | CH₂CH₂CH₂OMe | |
| 540 | 48 | CH₂CO₂Me | |
| 541 | 48 | CH₂N(Me)₂ | |
| 542 | 48 | CH₂SMe | |
| 543 | 48 | CH₂SPh | |
| 544 | 48 | Et | |
| 545 | 48 | Me | |
| 546 | 49 | CH₂SMe | |
| 547 | 49 | Et | |
| 548 | 49 | Me | |
| 549 | 50 | CH₂SMe | |
| 550 | 50 | Et | |
| 551 | 50 | Me | |
| 552 | 51 | CH(Me)₂ | |
| 553 | 51 | CH₂CF₃ | |
| 554 | 51 | CH₂CH₂CH₂OMe | |
| 555 | 51 | CH₂CO₂Me | |
| 556 | 51 | CH₂N(Me)₂ | |
| 557 | 51 | CH₂SMe | |
| 558 | 51 | CH₂SPh | |
| 559 | 51 | Et | |
| 560 | 51 | Me | |
| 561 | 52 | CH₂SMe | |
| 562 | 52 | Et | |
| 563 | 52 | Me | |
| 564 | 53 | CH₂SMe | |
| 565 | 53 | Et | |
| 566 | 53 | Me | |
| 567 | 54 | CH₂SMe | |
| 568 | 54 | Et | |
| 569 | 54 | Me | |
| 570 | 55 | CH₂SMe | |
| 571 | 55 | Et | |
| 572 | 55 | Me | |
| 573 | 56 | CH₂SMe | |
| 574 | 56 | Et | |
| 575 | 56 | Me | |

TABLE 5

A= 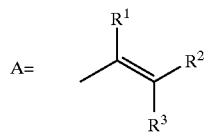

| No. | Skeleton | R¹ | R² | R³ | m.p. |
|---|---|---|---|---|---|
| 576 | 1 | H | Me | H | |
| 577 | 1 | H | Me | Me | |
| 578 | 2 | H | CH₂CF₃ | Me | |
| 579 | 2 | H | CO₂Et | H | |
| 580 | 2 | H | CO₂Me | H | |
| 581 | 2 | H | Et | Me | |
| 582 | 2 | H | H | H | |
| 583 | 2 | H | Me | H | |
| 584 | 2 | H | Me | Me | |
| 585 | 3 | H | Me | H | |
| 586 | 3 | H | Me | Me | |
| 587 | 4 | H | Me | H | |
| 588 | 4 | H | Me | Me | |
| 589 | 5 | H | Br | Br | |
| 590 | 5 | H | CH₂CF₃ | Me | |
| 591 | 5 | H | Cl | Cl | |
| 592 | 5 | H | CO₂Et | H | oil |
| 593 | 5 | H | CO₂Me | H | oil |
| 594 | 5 | H | Et | Me | |
| 595 | 5 | H | H | H | oil |
| 596 | 5 | H | Me | H | oil |
| 597 | 5 | H | Me | Me | |
| 598 | 5 | Me | CF₃ | H | |
| 599 | 6 | H | Me | H | |
| 600 | 6 | H | Me | Me | |
| 601 | 7 | H | Br | Br | |
| 602 | 7 | H | Cl | Cl | |
| 603 | 7 | H | Me | H | |
| 604 | 7 | H | Me | Me | |
| 605 | 7 | Me | CF₃ | H | |
| 606 | 8 | H | Br | Br | |
| 607 | 8 | H | Cl | Cl | |
| 608 | 8 | H | Me | H | |
| 609 | 8 | H | Me | Me | |
| 610 | 8 | Me | CF₃ | H | |
| 611 | 9 | H | Me | H | |
| 612 | 9 | H | Me | Me | |
| 613 | 10 | H | Me | H | |
| 614 | 10 | H | Me | Me | |
| 615 | 11 | H | Me | H | |
| 616 | 11 | H | Me | Me | |
| 617 | 12 | H | Me | H | |
| 618 | 12 | H | Me | Me | |
| 619 | 13 | H | Me | H | |
| 620 | 13 | H | Me | Me | |
| 621 | 14 | H | Me | H | |
| 622 | 14 | H | Me | Me | |
| 623 | 15 | H | Me | H | |
| 624 | 15 | H | Me | Me | |
| 625 | 16 | H | Me | H | |
| 626 | 16 | H | Me | Me | |
| 627 | 17 | H | Me | H | |
| 628 | 17 | H | Me | Me | |
| 629 | 18 | H | Me | H | |
| 630 | 18 | H | Me | Me | |
| 631 | 19 | H | Me | H | |
| 632 | 19 | H | Me | Me | |
| 633 | 20 | H | Me | H | |
| 634 | 20 | H | Me | Me | |
| 635 | 21 | H | Me | H | |
| 636 | 21 | H | Me | Me | |
| 637 | 22 | H | Br | Br | |
| 638 | 22 | H | Cl | Cl | |
| 639 | 22 | H | Me | H | |
| 640 | 22 | H | Me | Me | |
| 641 | 22 | Me | CF₃ | H | |
| 642 | 23 | H | Me | H | |
| 643 | 23 | H | Me | Me | |
| 644 | 24 | H | Me | H | |
| 645 | 24 | H | Me | Me | |
| 646 | 25 | H | Br | Br | |
| 647 | 25 | H | Cl | Cl | |
| 648 | 25 | H | Me | H | |
| 649 | 25 | H | Me | Me | |
| 650 | 25 | Me | CF₃ | H | |
| 651 | 26 | H | Br | Br | |
| 652 | 26 | H | Cl | Cl | |
| 653 | 26 | H | Me | H | |
| 654 | 26 | H | Me | Me | |
| 655 | 26 | Me | CF₃ | H | |
| 656 | 27 | H | Me | H | |
| 657 | 27 | H | Me | Me | |
| 658 | 28 | H | Me | H | |
| 659 | 28 | H | Me | Me | |
| 660 | 29 | H | Me | H | |
| 661 | 29 | H | Me | Me | |
| 662 | 30 | H | Me | H | |
| 663 | 30 | H | Me | Me | |
| 664 | 31 | H | Me | H | |
| 665 | 31 | H | Me | Me | |
| 666 | 32 | H | Me | H | |
| 667 | 32 | H | Me | Me | |
| 668 | 33 | H | Me | H | |
| 669 | 33 | H | Me | Me | |
| 670 | 34 | H | Me | H | |
| 671 | 34 | H | Me | Me | |
| 672 | 35 | H | Br | Br | |
| 673 | 35 | H | Cl | Cl | |
| 674 | 35 | H | Me | H | |
| 675 | 35 | H | Me | Me | |
| 676 | 35 | Me | CF₃ | H | |
| 677 | 36 | H | Me | H | |
| 678 | 36 | H | Me | Me | |
| 679 | 37 | H | Me | H | |
| 680 | 37 | H | Me | Me | |
| 681 | 38 | H | Br | Br | |
| 682 | 38 | H | Cl | Cl | |
| 683 | 38 | H | Me | H | |
| 684 | 38 | H | Me | Me | |
| 685 | 38 | Me | CF₃ | H | |
| 686 | 39 | H | Me | H | |
| 687 | 39 | H | Me | Me | |
| 688 | 40 | H | Br | Br | |
| 689 | 40 | H | Cl | Cl | |
| 690 | 40 | H | Me | H | |
| 691 | 40 | H | Me | Me | |
| 692 | 40 | Me | CF₃ | H | |
| 693 | 41 | H | Me | H | |
| 694 | 41 | H | Me | Me | |
| 695 | 42 | H | Me | H | |
| 696 | 42 | H | Me | Me | |
| 697 | 43 | H | Me | H | |
| 698 | 43 | H | Me | Me | |
| 699 | 44 | H | Me | H | |
| 700 | 44 | H | Me | Me | |
| 701 | 45 | H | Me | H | |
| 702 | 45 | H | Me | Me | |
| 703 | 46 | H | Me | H | |
| 704 | 46 | H | Me | Me | |
| 705 | 47 | H | Me | H | |
| 706 | 47 | H | Me | Me | |
| 707 | 48 | H | Br | Br | |
| 708 | 48 | H | Cl | Cl | |
| 709 | 48 | H | Me | H | |
| 710 | 48 | H | Me | Me | |
| 711 | 48 | Me | CF₃ | H | |
| 712 | 49 | H | Me | H | |
| 713 | 49 | H | Me | Me | |

TABLE 5-continued

A= [structure with R¹, R², R³ on alkene with methyl]

| No. | Skeleton | R¹ | R² | R³ | m.p. |
|---|---|---|---|---|---|
| 714 | 50 | H | Me | H | |
| 715 | 50 | H | Me | Me | |
| 716 | 51 | H | Br | Br | |
| 717 | 51 | H | Cl | Cl | |
| 718 | 51 | H | Me | H | |
| 719 | 51 | H | Me | Me | |
| 720 | 51 | Me | CF₃ | H | |
| 721 | 52 | H | Me | H | |
| 722 | 52 | H | Me | Me | |
| 723 | 53 | H | Me | H | |
| 724 | 53 | H | Me | Me | |
| 725 | 54 | H | Me | H | |
| 726 | 54 | H | Me | Me | |
| 727 | 55 | H | Me | H | |
| 728 | 55 | H | Me | Me | |
| 729 | 56 | H | Me | H | |
| 730 | 56 | H | Me | Me | |
| 1249 | 5 | H | CF₃ | H | |

TABLE 6

A= [oxazoline structure with R¹, R², R³, R⁴]

| No. | Skeleton | R¹ | R² | R³ | R⁴ | m.p. |
|---|---|---|---|---|---|---|
| 731 | 1 | H | H | H | H | |
| 732 | 1 | H | H | Me | H | |
| 733 | 1 | Me | H | H | H | |
| 734 | 3 | H | H | H | H | |
| 735 | 3 | H | H | Me | H | |
| 736 | 3 | Me | H | H | H | |
| 737 | 5 | 4-Cl-phenyl-CH₂ | H | Me | H | |
| 738 | 5 | H | H | H | H | oil |
| 739 | 5 | H | H | Me | H | oil |
| 740 | 5 | H | H | 3-pyridyl | H | |
| 741 | 5 | Me | H | H | H | |
| 742 | 7 | H | H | Me | H | |
| 743 | 7 | H | H | Me | Me | |
| 744 | 7 | Me | H | H | H | |
| 745 | 8 | 4-Cl-phenyl-CH₂ | H | Me | H | |
| 746 | 8 | H | H | H | H | |
| 747 | 8 | H | H | Me | H | |
| 748 | 8 | H | H | 3-pyridyl | H | |
| 749 | 8 | Me | H | H | H | |
| 750 | 14 | H | H | H | H | |
| 751 | 14 | H | H | Me | H | |
| 752 | 14 | Me | H | H | H | |
| 753 | 16 | H | H | H | H | |
| 754 | 18 | H | H | Me | H | |

TABLE 6-continued

A= [oxazoline structure with R¹, R², R³, R⁴]

| No. | Skeleton | R¹ | R² | R³ | R⁴ | m.p. |
|---|---|---|---|---|---|---|
| 755 | 22 | 4-Cl-phenyl-CH₂ | H | Me | H | |
| 756 | 22 | H | H | Me | H | |
| 757 | 22 | H | H | Me | Me | |
| 758 | 22 | H | H | 3-pyridyl | H | |
| 759 | 22 | Me | H | H | H | |
| 760 | 25 | 4-Cl-phenyl-CH₂ | H | Me | H | |
| 761 | 25 | H | H | Me | H | |
| 762 | 25 | H | H | Me | Me | |
| 763 | 25 | H | H | 3-pyridyl | H | |
| 764 | 25 | Me | H | H | H | |
| 765 | 26 | H | H | Me | H | |
| 766 | 26 | H | H | Me | Me | |
| 767 | 26 | Me | H | H | H | |
| 768 | 33 | Me | H | H | H | |
| 769 | 35 | 4-Cl-phenyl-CH₂ | H | Me | H | |
| 770 | 35 | H | H | Me | H | |
| 771 | 35 | H | H | Me | Me | |
| 772 | 35 | H | H | 3-pyridyl | H | |
| 773 | 35 | Me | H | H | H | |
| 774 | 38 | 4-Cl-phenyl-CH₂ | H | Me | H | |
| 775 | 38 | H | H | Me | H | |
| 776 | 38 | H | H | Me | Me | |
| 777 | 38 | H | H | 3-pyridyl | H | |
| 778 | 38 | Me | H | H | H | |
| 779 | 40 | H | H | Me | H | |
| 780 | 40 | H | H | Me | Me | |
| 781 | 40 | Me | H | H | H | |
| 782 | 48 | 4-Cl-phenyl-CH₂ | H | Me | H | |
| 783 | 48 | H | H | Me | H | |
| 784 | 48 | H | H | Me | Me | |
| 785 | 48 | H | H | 3-pyridyl | H | |
| 786 | 48 | Me | H | H | H | |
| 787 | 51 | 4-Cl-phenyl-CH₂ | H | Me | H | |
| 788 | 51 | H | H | Me | H | |
| 789 | 51 | H | H | Me | Me | |

TABLE 6-continued

A= [2-methyl-oxazoline with R¹, R², R³, R⁴ substituents]

| No. | Skeleton | R¹ | R² | R³ | R⁴ | m.p. |
|---|---|---|---|---|---|---|
| 790 | 51 | H | H | 3-pyridyl | H | |
| 791 | 51 | Me | H | H | H | |

TABLE 7

A= [2-methyl-thiazole with R¹ at 5-position, R² at 4-position]

| No. | Skeleton | R¹ | R² | m.p. |
|---|---|---|---|---|
| 792 | 5 | H | CF₃ | |
| 793 | 5 | H | CH₂CH₂OMe | |
| 794 | 5 | H | Me | oil |
| 795 | 5 | Me | 5-methyl-3-(trifluoromethyl)pyridin-3-yl | |
| 796 | 5 | Me | cyclopropyl | |
| 797 | 5 | Me | Me | 105° C. |
| 798 | 7 | H | CF₃ | |
| 799 | 7 | H | CH₂CH₂OMe | |
| 800 | 7 | H | Me | |
| 801 | 7 | Me | 5-methyl-3-(trifluoromethyl)pyridin-3-yl | |
| 802 | 7 | Me | cyclopropyl | |
| 803 | 7 | Me | Me | |
| 804 | 8 | H | CF₃ | |
| 805 | 8 | H | CH₂CH₂OMe | |
| 806 | 8 | H | Me | |
| 807 | 8 | Me | 5-methyl-3-(trifluoromethyl)pyridin-3-yl | |
| 808 | 8 | Me | cyclopropyl | |
| 809 | 8 | Me | Me | |
| 810 | 22 | H | CF₃ | |
| 811 | 22 | H | CH₂CH₂OMe | |
| 812 | 22 | H | Me | |

TABLE 7-continued

| No. | Skeleton | R¹ | R² | m.p. |
|---|---|---|---|---|
| 813 | 22 | Me | 5-methyl-3-(trifluoromethyl)pyridin-3-yl | |
| 814 | 22 | Me | cyclopropyl | |
| 815 | 22 | Me | Me | |
| 816 | 25 | H | CF₃ | |
| 817 | 25 | H | CH₂CH₂OMe | |
| 818 | 25 | H | Me | |
| 819 | 25 | Me | 5-methyl-3-(trifluoromethyl)pyridin-3-yl | |
| 820 | 25 | Me | cyclopropyl | |
| 821 | 25 | Me | Me | |
| 822 | 26 | H | CF₃ | |
| 823 | 26 | H | CH₂CH₂OMe | |
| 824 | 26 | H | Me | |
| 825 | 26 | Me | 5-methyl-3-(trifluoromethyl)pyridin-3-yl | |
| 826 | 26 | Me | cyclopropyl | |
| 827 | 26 | Me | Me | |
| 828 | 35 | H | CF₃ | |
| 829 | 35 | H | CH₂CH₂OMe | |
| 830 | 35 | H | Me | |
| 831 | 35 | Me | 5-methyl-3-(trifluoromethyl)pyridin-3-yl | |
| 832 | 35 | Me | cyclopropyl | |
| 833 | 35 | Me | Me | |
| 834 | 38 | H | CF₃ | |
| 835 | 38 | H | CH₂CH₂OMe | |
| 836 | 38 | H | Me | |
| 837 | 38 | Me | 5-methyl-3-(trifluoromethyl)pyridin-3-yl | |
| 838 | 38 | Me | cyclopropyl | |
| 839 | 38 | Me | Me | |
| 840 | 40 | H | CF₃ | |
| 841 | 40 | H | CH₂CH₂OMe | |
| 842 | 40 | H | Me | |

TABLE 7-continued

A= 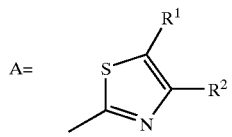

| No. | Skeleton | R¹ | R² | m.p. |
|---|---|---|---|---|
| 843 | 40 | Me | (5-methyl-3-trifluoromethyl-pyridinyl) | |
| 844 | 40 | Me | cyclopropyl | |
| 845 | 40 | Me | Me | |
| 846 | 48 | H | $CF_3$ | |
| 847 | 48 | H | $CH_2CH_2OMe$ | |
| 848 | 48 | H | Me | |
| 849 | 48 | Me | (5-methyl-3-trifluoromethyl-pyridinyl) | |
| 850 | 48 | Me | cyclopropyl | |
| 851 | 48 | Me | Me | |
| 852 | 51 | H | $CF_3$ | |
| 853 | 51 | H | $CH_2CH_2OMe$ | |
| 854 | 51 | H | Me | |
| 855 | 51 | Me | (5-methyl-3-trifluoromethyl-pyridinyl) | |
| 856 | 51 | Me | cyclopropyl | |
| 857 | 51 | Me | Me | |

TABLE 8

A= 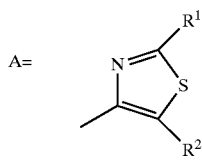

| No. | Skeleton | R¹ | R² | m.p. |
|---|---|---|---|---|
| 858 | 1 | Me | H | |
| 859 | 2 | Me | H | |
| 860 | 3 | Me | H | |
| 861 | 4 | Me | H | |
| 862 | 5 | $CF_3$ | H | |
| 863 | 5 | $CH=CH_2$ | Me | |
| 864 | 5 | H | H | oil |
| 865 | 5 | Me | H | oil |
| 866 | 6 | Me | H | |
| 867 | 7 | $CF_3$ | H | |
| 868 | 7 | $CH=CH_2$ | Me | |
| 869 | 7 | H | H | |
| 870 | 7 | Me | H | |
| 871 | 8 | $CF_3$ | H | |
| 872 | 8 | $CH=CH_2$ | Me | |
| 873 | 8 | H | H | |

TABLE 8-continued

A= 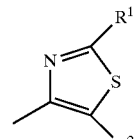

| No. | Skeleton | R¹ | R² | m.p. |
|---|---|---|---|---|
| 874 | 8 | Me | H | |
| 875 | 9 | Me | H | |
| 876 | 10 | Me | H | |
| 877 | 11 | Me | H | |
| 878 | 12 | Me | H | |
| 879 | 13 | Me | H | |
| 880 | 14 | Me | H | |
| 881 | 15 | Me | H | |
| 882 | 16 | Me | H | |
| 883 | 17 | Me | H | |
| 884 | 18 | Me | H | |
| 885 | 19 | Me | H | |
| 886 | 20 | Me | H | |
| 887 | 21 | Me | H | |
| 888 | 22 | $CF_3$ | H | |
| 889 | 22 | $CH=CH_2$ | Me | |
| 890 | 22 | H | H | |
| 891 | 22 | Me | H | |
| 892 | 23 | Me | H | |
| 893 | 24 | Me | H | |
| 894 | 25 | $CF_3$ | H | |
| 895 | 25 | $CH=CH_2$ | Me | |
| 896 | 25 | H | H | |
| 897 | 25 | Me | H | |
| 898 | 26 | $CF_3$ | H | |
| 899 | 26 | $CH=CH_2$ | Me | |
| 900 | 26 | H | H | |
| 901 | 26 | Me | H | |
| 902 | 27 | Me | H | |
| 903 | 28 | Me | H | |
| 904 | 29 | Me | H | |
| 905 | 30 | Me | H | |
| 906 | 31 | Me | H | |
| 907 | 32 | Me | H | |
| 908 | 33 | Me | H | |
| 909 | 34 | Me | H | |
| 910 | 35 | $CF_3$ | H | |
| 911 | 35 | $CH=CH_2$ | Me | |
| 912 | 35 | H | H | |
| 913 | 35 | Me | H | |
| 914 | 36 | Me | H | |
| 915 | 37 | Me | H | |
| 916 | 38 | $CF_3$ | H | |
| 917 | 38 | $CH=CH_2$ | Me | |
| 918 | 38 | H | H | |
| 919 | 38 | Me | H | |
| 920 | 39 | Me | H | |
| 921 | 40 | $CF_3$ | H | |
| 922 | 40 | $CH=CH_2$ | Me | |
| 923 | 40 | H | H | |
| 924 | 40 | Me | H | |
| 925 | 41 | Me | H | |
| 926 | 42 | Me | H | |
| 927 | 43 | Me | H | |
| 928 | 44 | Me | H | |
| 929 | 45 | Me | H | |
| 930 | 46 | Me | H | |
| 931 | 47 | Me | H | |
| 932 | 48 | $CF_3$ | H | |
| 933 | 48 | $CH=CH_2$ | Me | |
| 934 | 48 | H | H | |
| 935 | 48 | Me | H | |
| 936 | 49 | Me | H | |
| 937 | 50 | Me | H | |
| 938 | 51 | $CF_3$ | H | |
| 939 | 51 | $CH=CH_2$ | Me | |
| 940 | 51 | H | H | |
| 941 | 51 | Me | H | |

TABLE 8-continued

A= (thiazole with R¹ at 2-position, methyl at 4-position, R² at 5-position)

| No. | Skeleton | R¹ | R² | m.p. |
|-----|----------|----|----|------|
| 942 | 52 | Me | H | |
| 943 | 53 | Me | H | |
| 944 | 54 | Me | H | |
| 945 | 55 | Me | H | |
| 946 | 56 | Me | H | |

TABLE 9

A= (pyrazole with R¹ on N1, methyl at 3-position, R² at 5-position, R³ at 4-position)

| No. | Skeleton | R¹ | R² | R³ | m.p. |
|-----|----------|----|----|----|------|
| 947 | 5 | 4-CN-C₆H₄-CH₂- | Me | Me | |
| 948 | 5 | CH(Me)₂ | H | Me | |
| 949 | 5 | H | H | H | oil |
| 950 | 5 | Me | H | H | oil |
| 951 | 7 | 4-CN-C₆H₄-CH₂- | Me | Me | |
| 952 | 7 | CH(Me)₂ | H | Me | |
| 953 | 7 | H | H | H | |
| 954 | 7 | Me | H | H | |
| 955 | 8 | 4-CN-C₆H₄-CH₂- | Me | Me | |
| 956 | 8 | CH(Me)₂ | H | Me | |
| 957 | 8 | H | H | H | |
| 958 | 8 | Me | H | H | |
| 959 | 22 | 4-CN-C₆H₄-CH₂- | Me | Me | |
| 960 | 22 | CH(Me)₂ | H | Me | |
| 961 | 22 | H | H | H | |
| 962 | 22 | Me | H | H | |
| 963 | 25 | 4-CN-C₆H₄-CH₂- | Me | Me | |
| 964 | 25 | CH(Me)₂ | H | Me | |
| 965 | 25 | H | H | H | |
| 966 | 25 | Me | H | H | |

TABLE 9-continued

A= (pyrazole with R¹ on N1, methyl at 3-position, R² at 5-position, R³ at 4-position)

| No. | Skeleton | R¹ | R² | R³ | m.p. |
|-----|----------|----|----|----|------|
| 967 | 26 | 4-CN-C₆H₄-CH₂- | Me | Me | |
| 968 | 26 | CH(Me)₂ | H | Me | |
| 969 | 26 | H | H | H | |
| 970 | 26 | Me | H | H | |
| 971 | 35 | 4-CN-C₆H₄-CH₂- | Me | Me | |
| 972 | 35 | CH(Me)₂ | H | Me | |
| 973 | 35 | H | H | H | |
| 974 | 35 | Me | H | H | |
| 975 | 38 | 4-CN-C₆H₄-CH₂- | Me | Me | |
| 976 | 38 | CH(Me)₂ | H | Me | |
| 977 | 38 | H | H | H | |
| 978 | 38 | Me | H | H | |
| 979 | 40 | 4-CN-C₆H₄-CH₂- | Me | Me | |
| 980 | 40 | CH(Me)₂ | H | Me | |
| 981 | 40 | H | H | H | |
| 982 | 40 | Me | H | H | |
| 983 | 48 | 4-CN-C₆H₄-CH₂- | Me | Me | |
| 984 | 48 | CH(Me)₂ | H | Me | |
| 985 | 48 | H | H | H | |
| 986 | 48 | Me | H | H | |
| 987 | 51 | 4-CN-C₆H₄-CH₂- | Me | Me | |
| 988 | 51 | CH(Me)₂ | H | Me | |
| 989 | 51 | H | H | H | |
| 990 | 51 | Me | H | H | |

TABLE 10

A= 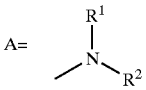

| No. | Skeleton | R¹ | R² | m.p. |
|---|---|---|---|---|
| 991 | 1 | H | C(=O)NMe₂ | |
| 992 | 1 | H | C(=O)OMe | |
| 993 | 2 | H | C(=O)NMe₂ | |
| 994 | 2 | H | C(=O)OMe | |
| 995 | 3 | H | C(=O)NMe₂ | |
| 996 | 3 | H | C(=O)OMe | |
| 997 | 4 | H | C(=O)NMe₂ | |
| 998 | 4 | H | C(=O)OMe | |
| 999 | 5 | H | C(=O)Me | |
| 1000 | 5 | H | C(=O)NMe₂ | 111° C. |
| 1001 | 5 | H | C(=O)OMe | oil |
| 1002 | 5 | Me | C(=O)H | |
| 1003 | 6 | H | C(=O)NMe₂ | |
| 1004 | 6 | H | C(=O)OMe | |
| 1005 | 7 | H | C(=O)Me | |
| 1006 | 7 | H | C(=O)NMe₂ | |
| 1007 | 7 | H | C(=O)OMe | |
| 1008 | 7 | Me | C(=O)Et | |
| 1009 | 8 | H | C(=O)Me | |
| 1010 | 8 | H | C(=O)NMe₂ | |
| 1011 | 8 | H | C(=O)OMe | |
| 1012 | 8 | Me | C(=O)Me | |
| 1013 | 9 | H | C(=O)NMe₂ | |
| 1014 | 9 | H | C(=O)OMe | |
| 1015 | 10 | H | C(=O)NMe₂ | |
| 1016 | 10 | H | C(=O)OMe | |
| 1017 | 11 | H | C(=O)NMe₂ | |
| 1018 | 11 | H | C(=O)OMe | |
| 1019 | 12 | H | C(=O)NMe₂ | |
| 1020 | 12 | H | C(=O)OMe | |
| 1021 | 13 | H | C(=O)NMe₂ | |
| 1022 | 13 | H | C(=O)OMe | |
| 1023 | 14 | H | C(=O)NMe₂ | |
| 1024 | 14 | H | C(=O)OMe | |
| 1025 | 15 | H | C(=O)NMe₂ | |
| 1026 | 15 | H | C(=O)OMe | |
| 1027 | 16 | H | C(=O)NMe₂ | |
| 1028 | 16 | H | C(=O)OMe | |
| 1029 | 17 | H | C(=O)NMe₂ | |
| 1030 | 17 | H | C(=O)OMe | |
| 1031 | 18 | H | C(=O)NMe₂ | |
| 1032 | 18 | H | C(=O)OMe | |
| 1033 | 19 | H | C(=O)NMe₂ | |
| 1034 | 19 | H | C(=O)OMe | |
| 1035 | 20 | H | C(=O)NMe₂ | |
| 1036 | 20 | H | C(=O)OMe | |
| 1037 | 21 | H | C(=O)NMe₂ | |
| 1038 | 21 | H | C(=O)OMe | |
| 1039 | 22 | H | C(=O)Et | |
| 1040 | 22 | H | C(=O)NMe₂ | |
| 1041 | 22 | H | C(=O)OMe | |
| 1042 | 22 | Me | C(=O)CH₂CH₂CH₃ | |
| 1043 | 23 | H | C(=O)NMe₂ | |
| 1044 | 23 | H | C(=O)OMe | |
| 1045 | 24 | H | C(=O)NMe₂ | |
| 1046 | 24 | H | C(=O)OMe | |
| 1047 | 25 | Et | C(=O)F3 | |
| 1048 | 25 | H | C(=O)Me | |
| 1049 | 25 | H | C(=O)NMe₂ | |
| 1050 | 25 | H | C(=O)OMe | |
| 1051 | 26 | Et | C(=O)CF₃ | |
| 1052 | 26 | H | C(=O)Et | |
| 1053 | 26 | H | C(=O)NMe₂ | |
| 1054 | 26 | H | C(=O)OMe | |
| 1055 | 27 | H | C(=O)NMe₂ | |
| 1056 | 27 | H | C(=O)OMe | |
| 1057 | 28 | H | C(=O)NMe₂ | |
| 1058 | 28 | H | C(=O)OMe | |
| 1059 | 29 | H | C(=O)NMe₂ | |
| 1060 | 29 | H | C(=O)OMe | |
| 1061 | 30 | H | C(=O)NMe₂ | |
| 1062 | 30 | H | C(=O)OMe | |
| 1063 | 31 | H | C(=O)NMe₂ | |
| 1064 | 31 | H | C(=O)OMe | |
| 1065 | 32 | H | C(=O)NMe₂ | |
| 1066 | 32 | H | C(=O)OMe | |
| 1067 | 33 | H | C(=O)NMe₂ | |
| 1068 | 33 | H | C(=O)OMe | |
| 1069 | 34 | H | C(=O)NMe₂ | |
| 1070 | 34 | H | C(=O)OMe | |
| 1071 | 35 | Et | C(=O)CF₃ | |
| 1072 | 35 | H | C(=O)Me | |
| 1073 | 35 | H | C(=O)NMe₂ | |
| 1074 | 35 | H | C(=O)OMe | |
| 1075 | 36 | H | C(=O)NMe₂ | |
| 1076 | 36 | H | C(=O)OMe | |
| 1077 | 37 | H | C(=O)NMe₂ | |
| 1078 | 37 | H | C(=O)OMe | |
| 1079 | 38 | Et | C(=O)CF₃ | |
| 1080 | 38 | H | C(=O)Me | |
| 1081 | 38 | H | C(=O)NMe₂ | |
| 1082 | 38 | H | C(=O)OMe | |
| 1083 | 39 | H | C(=O)NMe₂ | |
| 1084 | 39 | H | C(=O)OMe | |
| 1085 | 40 | Et | C(=O)CF₃ | |
| 1086 | 40 | H | C(=O)CH(Me₂) | |
| 1087 | 40 | H | C(=O)NMe₂ | |
| 1088 | 40 | H | C(=O)OMe | |
| 1089 | 41 | H | C(=O)NMe₂ | |
| 1090 | 41 | H | C(=O)OMe | |
| 1091 | 42 | H | C(=O)NMe₂ | |
| 1092 | 42 | H | C(=O)OMe | |
| 1093 | 43 | H | C(=O)NMe₂ | |
| 1094 | 43 | H | C(=O)OMe | |
| 1095 | 44 | H | C(=O)NMe₂ | |
| 1096 | 44 | H | C(=O)OMe | |
| 1097 | 45 | H | C(=O)NMe₂ | |
| 1098 | 45 | H | C(=O)OMe | |
| 1099 | 46 | H | C(=O)NMe₂ | |
| 1100 | 46 | H | C(=O)OMe | |
| 1101 | 47 | H | C(=O)NMe₂ | |
| 1102 | 47 | H | C(=O)OMe | |
| 1103 | 48 | Et | C(=O)CF₃ | |
| 1104 | 48 | H | C(=O)Me | |
| 1105 | 48 | H | C(=O)NMe₂ | |
| 1106 | 48 | H | C(=O)OMe | |
| 1107 | 49 | H | C(=O)NMe₂ | |
| 1108 | 49 | H | C(=O)OMe | |
| 1109 | 50 | H | C(=O)NMe₂ | |
| 1110 | 50 | H | C(=O)OMe | |
| 1111 | 51 | Et | C(=O)CF₃ | |
| 1112 | 51 | H | C(=O)Me | |
| 1113 | 51 | H | C(=O)NMe₂ | |
| 1114 | 51 | H | C(=O)OMe | |
| 1115 | 52 | H | C(=O)NMe₂ | |
| 1116 | 52 | H | C(=O)OMe | |
| 1117 | 53 | H | C(=O)NMe₂ | |
| 1118 | 53 | H | C(=O)OMe | |
| 1119 | 54 | H | C(=O)NMe₂ | |
| 1120 | 54 | H | C(=O)OMe | |
| 1121 | 55 | H | C(=O)NMe₂ | |
| 1122 | 55 | H | C(=O)OMe | |
| 1123 | 56 | H | C(=O)NMe₂ | |
| 1124 | 56 | H | C(=O)OMe | |

TABLE 11

A= $\begin{array}{c} X\diagup R^1 \\ \diagdown R^2 \end{array}$

| No. | Skeleton | X | R¹ | R² | m.p. |
|---|---|---|---|---|---|
| 1125 | 5 | NMe | Me | Me | |
| 1126 | 5 | O | H | Me | oil |
| 1127 | 5 | O | H | H | oil |
| 1128 | 5 | O | H | Et | oil |
| 1129 | 5 | O | C(=O)Me | H | oil |
| 1130 | 5 | O | —CH₂CH(OMe)CH₂O— | | oil |
| 1131 | 5 | O | —CH(Me)CH(Me)O— | | oil |
| 1132 | 5 | O | —CH(Et)CH₂O— | | oil |
| 1133 | 5 | O | —CH(CH₂SEt)CH₂O— | | oil |
| 1134 | 5 | O | —CH₂CH₂O— | | |
| 1135 | 5 | S | —CH₂CH₂CH₂S— | | oil |
| 1136 | 7 | O | —CH₂CH(OMe)CH₂O— | | |
| 1137 | 7 | O | H | Me | |
| 1138 | 7 | O | H | Et | |
| 1139 | 7 | O | —CH(Me)CH(Me)O— | | |
| 1140 | 7 | O | —CH(Et)CH₂O— | | |
| 1141 | 7 | S | —CH₂CH₂CH₂S— | | |
| 1142 | 8 | NMe | Me | Me | |
| 1143 | 8 | O | H | Me | oil |
| 1144 | 8 | O | —CH₂CH(OMe)CH₂O— | | |
| 1145 | 8 | O | H | Me | |
| 1146 | 8 | O | H | Et | |
| 1147 | 8 | O | H | H | |
| 1148 | 8 | O | C(=O)Me | H | |
| 1149 | 8 | O | —CH₂CH₂O— | | |
| 1150 | 8 | O | —CH(Me)CH(Me)O— | | |
| 1151 | 8 | O | —CH(Et)CH₂O— | | |
| 1152 | 8 | S | —CH₂CH₂CH₂S— | | |
| 1153 | 22 | O | —CH₂CH(OMe)CH₂O— | | |
| 1154 | 22 | O | H | Me | |
| 1155 | 22 | O | H | Et | |
| 1156 | 22 | O | —CH(Me)CH(Me)O— | | |
| 1157 | 22 | O | —CH(Et)CH₂O— | | |
| 1158 | 22 | S | —CH₂CH₂CH₂S- | | |
| 1159 | 25 | O | —CH₂CH(OMe)CH₂O— | | |
| 1160 | 25 | O | H | Me | |
| 1161 | 25 | O | H | Et | |
| 1162 | 25 | O | —CH(Me)CH(Me)O— | | |
| 1163 | 25 | O | —CH(Et)CH₂O— | | |
| 1164 | 25 | S | —CH₂CH₂CH₂S— | | |
| 1165 | 26 | O | —CH₂CH(OMe)CH₂O— | | |
| 1166 | 26 | O | H | Me | |
| 1167 | 26 | O | H | Et | |
| 1168 | 26 | O | —CH(Me)CH(Me)O— | | |
| 1169 | 26 | O | —CH(Et)CH₂O— | | |
| 1170 | 26 | S | —CH₂CH₂CH₂S— | | |
| 1171 | 35 | NMe | Me | Me | |
| 1172 | 35 | O | —CH₂CH(OMe)CH₂O— | | |
| 1173 | 35 | O | H | Me | |
| 1174 | 35 | O | H | Et | |
| 1175 | 35 | O | H | H | |
| 1176 | 35 | O | C(=O)Me | H | |
| 1177 | 35 | O | —CH₂CH₂O— | | |
| 1178 | 35 | O | —CH(Me)CH(Me)O— | | |
| 1179 | 35 | O | —CH(Et)CH₂O— | | |
| 1180 | 35 | S | —CH₂CH₂CH₂S— | | |
| 1181 | 38 | NMe | Me | Me | |
| 1182 | 38 | O | —CH₂CH(OMe)CH₂— | | |
| 1183 | 38 | O | H | Me | |
| 1184 | 38 | O | H | Et | |
| 1185 | 38 | O | H | H | |
| 1186 | 38 | O | C(=O)Me | H | |
| 1187 | 38 | O | —CH₂CH₂O— | | |
| 1188 | 38 | O | —CH(Me)CH(Me)O— | | |
| 1189 | 38 | O | —CH(Et)CH₂O— | | |
| 1190 | 38 | S | —CH₂CH₂CH₂S— | | |
| 1191 | 40 | O | —CH₂CH(OMe)CH₂O— | | |
| 1192 | 40 | O | H | Me | |
| 1193 | 40 | O | H | Et | |
| 1194 | 40 | O | —CH(Me)CH(Me)O— | | |
| 1195 | 40 | O | —CH(Et)CH₂O— | | |
| 1196 | 40 | S | —CH₂CH₂CH₂S— | | |
| 1197 | 48 | O | —CH₂CH(OMe)CH₂O— | | |
| 1198 | 48 | O | H | Me | |
| 1199 | 48 | O | H | Et | |
| 1200 | 48 | O | —CH(Me)CH(Me)O— | | |
| 1201 | 48 | O | —CH(Et)CH₂O— | | |
| 1202 | 48 | S | —CH₂CH₂CH₂S— | | |
| 1203 | 51 | O | —CH₂CH(OMe)CH₂O— | | |
| 1204 | 51 | O | H | Me | |
| 1205 | 51 | O | H | Et | |
| 1206 | 51 | O | —CH(Me)CH(Me)O— | | |
| 1207 | 51 | O | —CH(Et)CH₂O— | | |
| 1208 | 51 | S | —CH₂CH₂CH₂S— | | |
| 1209 | 5 | O | CO(2,4,6-Cl₃—Ph) | H | |
| 1210 | 5 | O | CO(3-CF₃—Ph) | H | |
| 1211 | 5 | O | CO(2-OCF₃—Ph) | H | |
| 1212 | 5 | O | CO(2-F-4-Cl—Ph) | H | |
| 1213 | 5 | O | CO(2,6-F₂—Ph) | H | |
| 1214 | 5 | O | CO(2,6-Cl₂—Ph) | H | |
| 1215 | 5 | O | CO(2,6-Cl₂-4-CF₃—Ph) | H | |
| 1216 | 5 | O | CO(2,3-Cl₂—Ph) | H | |
| 1217 | 5 | O | CO(3-CF₃-5-NO₂Ph) | H | |
| 1218 | 5 | S | CH₂CF₃ | H | |
| 1219 | 5 | O | 4-OCF₃—Ph | H | |
| 1220 | 5 | O | 3-(OCF₂CF₂H)—Ph | H | |
| 1221 | 5 | O | 4-F—Ph | H | |
| 1222 | 5 | O | 3-CF₃—Ph | H | |
| 1223 | 5 | O | 3-F—Ph | H | |
| 1224 | 5 | O | OCH₂CF₃ | H | |
| 1225 | 5 | S | 4-CF₃—Ph | H | |
| 1226 | 5 | S | 4-F—Ph | H | |
| 1227 | 5 | S | Ph | H | |
| 1228 | 5 | O | SO₂Me | H | |
| 1229 | 5 | SO | CH₂CF₃ | H | |
| 1230 | 5 | SO₂ | CH₂CF₃ | H | |
| 1231 | 5 | O | CH₂CHCCl₂ | H | |
| 1232 | 5 | O | C₂H₄O(4-CF₃Py-2-yl) | H | |
| 1233 | 5 | SO | C₂H₄O(4-CF₃Py-2-yl) | H | |
| 1234 | 5 | SO₂ | C₂H₄O(4-CF₃Py-2-yl) | H | |
| 1235 | 5 | S | C₂H₄O(4-CF₃Py-2-yl) | H | |

B. FORMULATION EXAMPLES a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water and grinding the mixture in a ball mill to a fineness of below 5 microns.

d) An emulsifiable concentrate can be prepared from 15 parts by weight of active substance, 75 parts by weight of cyclohexane as solvent and 10 parts by weight of oxyethylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, and these are dried and mixed intimately. The wettable powder amounts to approx. 5% by weight and the inert carrier material to approx. 95% by weight of the finished granules.

C. BIOLOGICAL EXAMPLES

In Examples A to L below, compounds are considered to be active when, at a concentration of 500 ppm or less, their action on the harmful organisms is 50% or more.

Example A

Cut stems of bean plants (*Phaseolus vulgaris*) carrying one leaf were transferred into brown glass bottles filled with tap water and subsequently populated with approximately 100 spider mites (*Tetranychus urticae*). The plant leaf and the spider mites were then dipped for 5 seconds into an aqueous solution of the formulated preparation to be examined. After the solution had run off, plants and animals were stored in a climatized chamber (16 hours of light/day, 25° C., 40–60% relative atmospheric humidity). After 6 days of storage, the effect of the preparation on all stages of the spider mites was determined. The following examples were active: Nos. 43, 45, 97, 1132.

Example B

Germinated field bean seeds (*Vicia faba*) with radicles were transferred into brown glass bottles filled with tap water and subsequently populated with approximately 100 black bean aphids (*Aphis fabae*). Plants and aphids were then dipped for 5 seconds into an aqueous solution of the formulated preparation to be examined. After the solution had run off, plants and animals were stored in an acclimatized chamber (16 hours of light/day, 25° C., 40–60% relative atmospheric humidity). After 3 and 6 days of storage, the effect of the preparation on the aphids (mortality) was determined. The following examples were active: Nos. 33, 36, 357, 1126.

Example C

A Petri dish whose bottom was covered with filter paper and which contained about 5 ml of culture medium was prepared. Pieces of filter paper with about 30, one-day-old eggs of the American tobacco budworm (*Heliothis virescens*) were dipped for 5 seconds into an aqueous solution of the formulated preparation to be examined and subsequently placed in a Petri dish. A further 200 µl of the aqueous solution were spread over the culture medium. The Petri dish was closed and then stored at about 25° C. in a climatized chamber. After 6 days of storage, the effect of the preparation on the eggs and any larvae which may have hatched from these (mortality) was determined. The following examples were active: Nos. 6, 27, 28, 29, 31, 35, 39, 43, 45, 59, 97, 226, 227, 228, 229, 351, 356, 357, 592, 593, 595, 949, 1001, 1126, 1129, 1132.

Example D

A Petri dish whose bottom was covered with filter paper and which contained about 5 ml of culture medium was prepared. Five L2 larvae of the Egyptian cotton leaf worm (*Spodoptera littoralis*) were counted into small beakers. 200 µl of an aqueous solution of the formulated preparation to be examined were pipetted into the beaker. The treated larvae were then poured into the Petri dish, and a further 200 µl of the aqueous solution were distributed over the culture medium. The Petri dish was closed and then stored at about 25° C. in a climatized chamber. After 6 days of storage, the effect of the preparation on the larvae (mortality) was determined. The following examples were active: Nos. 27, 28, 29, 39, 43, 45, 59.

Example E

A Petri dish, half of whose bottom was covered with filter paper and which contained a germinated maize corn on a moist cotton pad, was prepared. About 50, 4–5 day-old eggs of the corn rootworm (*Diabrotica undecimpunctata*) were transferred onto the filter paper. Three drops of 200 µl of an aqueous solution of the formulated preparation to be examined were pipetted onto the eggs, and the rest was pipetted onto the maize corn. The Petri dish was closed and then stored at about 25° C. in a climatized chamber. After 6 days of storage, the effect of the preparation on the eggs and any larvae which may have hatched from these (mortality) was determined. The following examples were active: No. 7.

Example F

Part A of the examination (contact action): in a glass vessel, an aqueous solution of the formulated preparation to be examined was added to about 5000 freshly hatched active (mobile) larvae (2nd development stage) of the root gall nematode (*Meloidogyne incognita*) (final volume 20 ml). After 6 days of permanent exposure of the nematode larvae, the percentage of the individual larvae immobilized by the action of the preparation was determined in comparison to the untreated controls (nematicidal contact action in percent).

Part B of the examination (soil drench action): to this end, the entire solution from part A of the examination (active compound and pre-treated nematode larvae) was poured into a pot, filled with 60 ml of soil, into which three 9-day-old cucumber plants (*Cucumis sativus*) had been planted. This drench application reduced the active compound content based on the soil volume to one third of the active compound content in part A of the examination. After 2 weeks in a greenhouse at about 26° C. (watering: twice a day), the root balls of the cucumber plants were carefully washed out of the soil mixture contaminated with nematodes. The number of root galls per plant was counted and compared to the infection of untreated control plants. The reduction of the infection in percent as a criterion for the assessment of the activity was calculated using Abbott's formula (nematicidal soil drench action). The following examples were active: Nos. 6, 7, 29, 32, 34, 44, 356.

Example G

Germinated field bean seeds (*Vicia faba*) with radicles were transferred into brown glass bottles filled with tap water. Four milliliters of an aqueous solution of the formulated preparation to be examined were pipetted into the brown glass bottle. The field bean was then heavily infested with approximately 100 black bean aphids (*Aphis fabae*). Plants and animals were then stored in a climatized chamber (16 hours of light/day, 25° C., 40–60% relative atmospheric humidity). After 3 and 6 days of storage, the root-systemic effect of the preparation on the aphids (mortality) was determined. The following examples were active: No. 1126.

Example H

A Petri dish whose bottom was covered with filter paper and which contained about 5 ml of culture medium was prepared. Five L2 larvae of the sugar beet armyworm (*Spodoptera exigua*) were counted into a small beaker. 200 μl of an aqueous solution of the formulated preparation to be examined were pipetted into the beaker. The treated larvae were then poured into the Petri dish and a further 200 μl of the aqueous solution were distributed over the culture medium. The Petri dish was closed and then stored at 25° C. in a climatized chamber. After 6 days of storage, the effect of the preparation on the larvae (mortality) was determined. The following examples were active: Nos. 31, 97, 226, 227, 228, 229, 351, 356, 357, 592, 593, 595, 949, 1001, 1126, 1129, 1132.

Example I

Cotton plants were sprayed with an aqueous solution of the formulated preparation to be examined. After drying, leaves were cut off, placed into a Petri dish and populated with 5 L2 larvae of the sugar beet armyworm (*Spodoptera exigua*). After 4 days of storage at about 23° C., the effect of the preparation on the larvae (mortality) was determined. The following examples were active: Nos. 27, 28, 45, 59.

Example J

Culture medium was mixed with an aqueous solution of the formulated preparation to be examined and populated with 10 L1 larvae of the codling moth (*Carpocapsa pomonella*). After 14 days of storage at about 23° C., the effect of the preparation on the larvae (mortality) was determined. The following examples were active: Nos. 28, 59.

Example K

Cotton leaves were placed into a Petri dish, populated with in each case 5 L1, L2, L3 and L4 larvae of the American tobacco budworm (*Heliothis virescens*) and sprayed with an aqueous solution of the formulated preparation to be examined. After 4 days of storage at about 25° C., the effect of the preparation on the larvae (mortality) was determined. The following examples were active: No. 27

Example L

A cabbage leaf was sprayed with an aqueous solution of the formulated preparation to be examined. After drying, the treated leaf was populated with larvae of the diamondback moth (*Plutella xylostella*). After 4 days of storage at about 25° C., the effect of the preparation on the larvae (mortality) was determined. The following examples were active: Nos. 27, 28, 45.

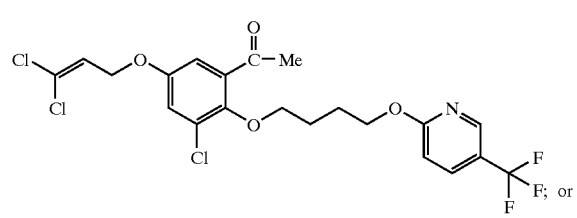

What is claimed is:

1. A compound of the formula (I)

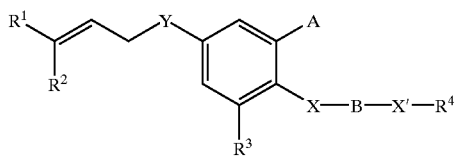

or a salt thereof, in which $R^1$ and $R^2$ independently of one another are halogen, Y is —O—, —S— or —NH—, X is —O—, —S(O)$_r$— or —NR$^5$—, where r=0, 1 or 2 and $R^5$ is hydrogen or $C_1$–$C_8$-alkyl, X' is a direct bond, —O—, —S(O)$_r$— or —NR$^5$—, where r and $R^5$ are as defined above, $R^3$ is hydrogen, halogen, nitro, cyano, $C_1$–$C_8$-alkyl, $C_1$–$C_8$-haloalkyl, $C_1$–$C_8$-alkoxy, $C_1$–$C_8$-haloalkoxy or $C_3$–$C_{10}$-cycloalkyl, A is one of the groups —C(=Z)-R$^6$, —C(=Z)-OR$^6$, —C(=Z)-SR$^6$, —C(=Z)-NR$^7$R$^8$, or —C(=Z)-O—N=C(NH$_2$)—R$^6$, Z is O, S, N—R$^{33}$, N—O—R$^{33}$ or N—NR$^{33}$R$^{34}$, $R^6$, $R^7$, and $R^8$, $R^{33}$ and $R^{34}$ independently of one another are hydrogen, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl, $C_4$–$C_{10}$-cycloalkynyl, $C_6$–$C_{14}$-aryl or heteroaryl having one to three ring heteroatoms which for their part may be substituted by halogen, hydroxyl, cyano, nitro, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl, $C_4$–$C_{10}$-cycloalkynyl, $C_6$–$C_{14}$-aryl, halogen-substituted $C_6$–$C_{14}$-aryl, heteroaryl having one to three ring heteroatoms or halogen-substituted heteroaryl having one to three ring heteroatoms, amino, N—($C_1$–$C_8$-alkyl)amino, N,N-bis-($C_1$–$C_8$-alkyl)amino, tri-($C_1$–$C_8$-alkyl)silyl, aryl-($C_1$–$C_8$)-dialkylsilyl, diaryl-($C_1$–$C_8$)-alkylsilyl, triarylsilyl, $C_1$–$C_8$-alkoxy and/or $C_1$–$C_8$-haloalkoxy, B is a divalent bridge and is alkylene having one to twelve carbon atoms, cycloalkylene having three to fourteen carbon atoms, alkylene-cycloalkylene having four to twenty-six carbon atoms, alkylene-cycloalkylene-alkylene having five to thirty-eight carbon atoms, where these bridges may have one to three ethylenically unsaturated bonds and/or may be interrupted by —O—, —S—, —C(=O)O— or —NR$^5$— groups, where $R^5$ is as defined above and where the bridge may be unsubstituted or substituted by one to ten substituents selected from the group consisting of $C_1$–$C_3$-alkyl, trifluoromethyl and trichloromethyl, and $R^4$ is a monovalent $C_6$–$C_{14}$-aryl radical or nitrogen-containing heteroaryl radical having at least one ring heteroatom which is unsubstituted or substituted by one to four radicals selected from the group consisting of halogen, cyano, nitro, thiocyanato, isocyanato, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl, $C_4$–$C_{10}$-cycloalkynyl, $C_6$–$C_{14}$-aryl, nitrogen-containing heteroaryl having one to three ring heteroatoms, where these substituents for their part may be substituted by radicals selected from the group consisting of halogen, cyano, nitro, $C_1$–$C_8$-alkyl, $C_1$–$C_8$-haloalkyl, $C_1$–$C_8$-alkoxy, $C_1$–$C_8$-haloalkoxy, —C(=Z)-R$^6$, —C(=Z)-OR$^6$, —C(=Z)-SR$^6$, —C(=Z)-NR$^7$R$^8$, —C(=Z)-O—N=C(NH$_2$)—R$^6$, —O—C(=Z)-R$^6$, —O—C(=Z)-OR$^6$, —O—C(=Z)-SR$^6$, —O—C(=Z)-NR$^7$R$^8$, —S—C(=Z)-R$^6$, —S—C(=Z)-OR$^6$, —S—C(=Z)-SR$^6$, —S—C(=Z)-NR$^7$R$^8$, —NR$^9$—C(=Z)-R$^6$, —NR$^9$—C(=Z)-OR$^6$, —NR$^9$—C(=Z)-SR$^6$, —NR$^9$—C(=Z)-NR$^7$R$^8$, —OR$^6$, —SR$^6$, —S(=O)R$^6$, —S(=O)$_2$R$^6$, —NR$^7$R$^8$, where Z, $R^6$, $R^7$, and $R^8$ are as defined above and $R^9$ is independently any group defined above for $R_6$.

2. A compound of the formula (I) as claimed in claim 1 wherein $R^1$ and $R^2$ are each chlorine or bromine.

3. A compound of the formula (I) as claimed in claim 1 wherein Y is —O—.

4. A compound of the formula (I) as claimed in claim 1 wherein $R^1$ and $R^2$ are each chlorine and Y is —O—.

5. A compound of the formula (I) as claimed in claim 1 wherein X is —O—, —S— or —NH— and X' is a direct bond, —O—, —S— or —NH—.

6. A compound of the formula (I) as claimed in claim 5 wherein X and X' are each —O— or X is —O— and X' is a direct bond.

7. A compound of the formula (I) as claimed in claim 1 wherein $R^3$ is hydrogen, fluorine, chlorine, bromine, methyl, trifluoromethyl, monochloromethyl, dichloromethyl, trichloromethyl, methoxy, trifluoromethoxy, monochloromethoxy, dichloromethoxy, trichloromethoxy, nitro, cyano, or cyclohexyl.

8. A compound of the formula (I) as claimed in claim 1 wherein $R^3$ is methyl, trifluoromethyl, cyano, chlorine or bromine.

9. A compound of the formula (I) as claimed in claim 1 wherein Z is O, N—OH, N—OCH$_3$ or N—CH$_2$—CH=CH$_2$.

10. A compound of the formula (I) as claimed in claim 1 wherein A is a group of the formula —C(=O)—CH$_3$, —C(=N—OCH$_3$)—CH$_3$, —C(=N—OH)—CH$_3$, —C(=O)—OCH$_3$, —C(=O)—CH=CH—N(CH$_3$)$_2$, —C(=O)—NH—C$_2$H$_5$, —C(=O)—NH$_2$, —C(=O)—N(CH$_3$)$_2$, —C(=O)—NH—CH$_2$—CH$_2$—OH, —C(=O)—NH—CH(CH$_3$)—CH$_2$—OH, —C(=O)—CHBr$_2$, —C(=O)—N(CH$_3$)—O—CH$_3$, —C(=N—O—CH$_2$—CH=CH$_2$)—CH$_3$, —C(=S)—NH$_2$, —C(=O)—O—C$_6$H$_5$, —C(=O)—O—C$_3$H$_7$, —C(=O)-imidazolyl, —C(=O)-3-ethyl-1,2,4-oxadiazol-5-yl, —C(=O)-2-Δ-oxazolin-2-yl, —C(=O)-1-methylpyrazol-3-yl, —C(=O)-ethyn-2-yl, —C(=O)-1-hydroxyethyn-2-yl, —C(=O)-1-trimethylsilylethyn-2-yl, —C(=O)-1-hexylethyn-2-yl, —C(=O)-1-(2-chlorophenyl)ethyn-2-yl, —C(=O)-1-methoxyethyn-2-yl or —C(=O)-ethen-2-yl.

11. A compound of the formula (I) as claimed in claim 1 wherein A is —C(=Z)-R$^6$, —C(=Z)-OR$^6$, —C(=Z)-SR$^6$, or —C(=Z)-NR$^7$R$^8$, where Z, R$^6$, R$^7$, and R$^8$ are as defined in claim 1.

12. A compound of the formula (I) as claimed in claim 1 wherein B is a group of the formulae P$^1$ to P$^6$ P$^1$ = 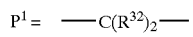

P$^2$ = 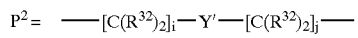

P$^3$ = 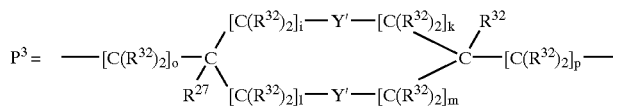

P$^4$ = 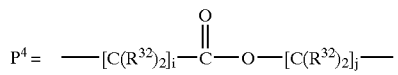

P$^5$ = 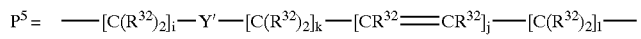

P$^6$ = 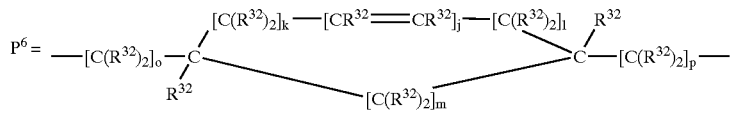

in which R$^{32}$ in each case independently of the others is hydrogen, C$_1$–C$_3$-alkyl or trifluoromethyl, Y' in each case independently of the others is a direct C—C bond, —O—, —S— or —NH—, i is an integer from 1 to 6,
j is an integer from 1 to 6,
k is an integer from 0 to 2,
l is an integer from 0 to 2,
m is an integer from 0 to 2,
o is an integer from 0 to 1 and
p is an integer from 0 to 1.

13. A compound of the formula (I) as claimed in claim 1 wherein B is a group of the formula —C$_q$H$_{2q}$- and q is an integer from 2 to 4.

14. A compound of the formula (I) as claimed in claim 1 wherein R$^4$ is C$_6$–C$_{14}$-aryl which is unsubstituted or substituted by one to three radicals selected from the group consisting of halogen, cyano, nitro, thiocyanato, isocyanato, C$_1$–C$_6$-alkyl, C$_3$–C$_8$-cycloalkyl, C$_2$–C$_8$-alkenyl, C$_4$–C$_8$-cycloalkenyl and C$_2$–C$_8$-alkynyl, where one or more hydrogen atoms of the C$_1$–C$_6$-alkyl, C$_3$–C$_8$-cycloalkyl, C$_2$–C$_8$-alkenyl, C$_4$–C$_8$-cycloalkenyl and/or C$_2$–C$_8$-alkynyl radicals may be substituted by halogen and/or cyano.

15. A compound of the formula (I) as claimed in claim 1 wherein R$^4$ is selected from the group consisting of phenyl, pyridyl, pyrimidyl, pyrazynyl, pyrazolyl and naphthyl which are unsubstituted or substituted by one or more radicals selected from the group consisting of halogen, cyano, nitro, C$_1$–C$_3$-alkyl, C$_1$–C$_3$-haloalkyl, C$_1$–C$_3$-alkoxy, C$_1$–C$_3$-haloalkoxy, —C(=Z)-R$^6$, —C(=Z)-OR$^6$, —C(=Z)-SR$^6$, —C(=Z)-NR$^7$R$^8$, —O—C(=Z)-R$^6$, —O—C(=Z)-OR$^6$, —O—C(=Z)-SR$^6$, —O—C(=Z)-NR$^7$R$^8$, —S—C(=Z)-R$^6$, —S—C(=Z)OR$^6$, —S—C(=Z)-SR$^6$, —S—C(=Z)-NR$^7$R$^8$, —NR$^9$—C(=Z)-R$^6$, —NR$^9$—C(=Z)-OR$^6$, —NR$^9$—C(=Z)-SR$^6$, —NR$^9$—C(=Z)-NR$^7$R$^8$, —OR$^6$, —SR$^6$, —S(=O)R$^6$ and —S(=O)$_2$R$^6$, where Z, R$^6$, R$^7$, R$^8$ and R$^9$ are as defined in claim 1.

16. A compound of the formula (I) as claimed in claim 1 wherein R$^4$ is phenyl or pyridyl which carries one to three substituents from the group consisting of halogen, cyano, nitro, C$_1$–C$_3$-alkyl and C$_1$–C$_3$-haloalkyl or of combinations of these substituents.

17. A compound of the formula (I) as claimed in claim 1 wherein R$^4$ is trifluoromethylphenyl, chlorophenyl, nitrophenyl, nitropyridyl, trifluoromethylpyridyl, di(trifluoromethyl)pyridyl, chloropyridyl, dichloropyridyl, chlorotrifluoromethylpyridyl, trifluoromethylpyrimidyl, di(trifluoromethyl)pyrimidyl, methyltrifluoromethylpyrimidyl or trifluoromethylpyrazolyl.

18. A process for preparing compounds of the formula (I) as claimed in claim 1, which process comprises the following steps:

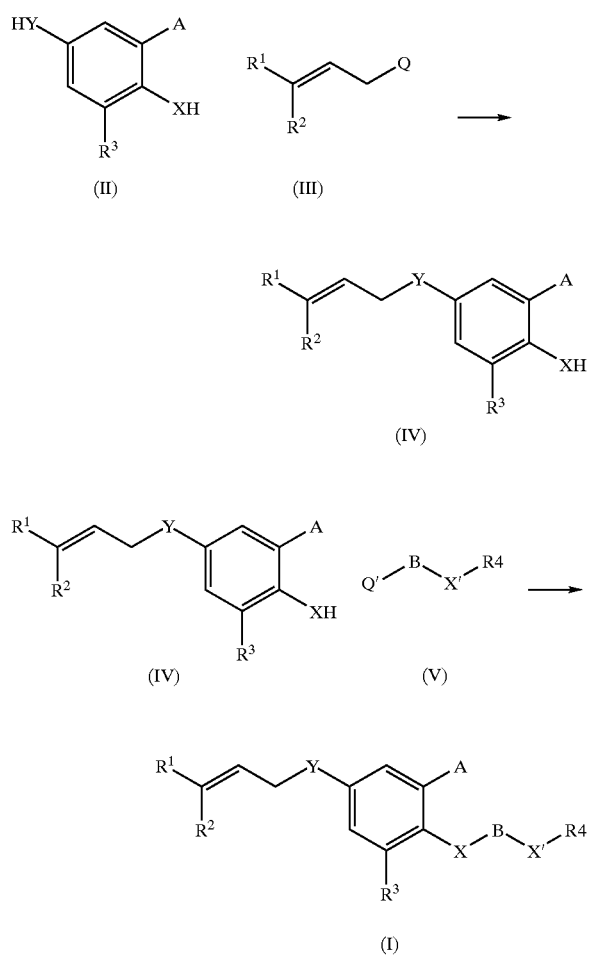

a) reacting the compounds of the formulae II and III to give the compound of the formula IV and
b) reacting the compounds of the formulae IV and V to give the compound of the formula I,
where $R^1$, $R^2$, $R^3$, $R^4$, A, Y, X and X' are as defined in claim 1 and Q and Q' are leaving groups.

19. A composition having insecticidal, acaricidal, ixodicidal, nematicidal, molluscicidal and/or fungicidal action, which comprises a pesticidally effective amount of one or more compounds of the formula (I) or salts thereof as claimed in claim 1 and one or more formulation auxiliaries therefor.

20. A composition as claimed in claim 19 comprising a mixture of carriers and/or surfactants.

21. A method for controlling animal pests comprising the step of directly or indirectly applying to the pest a pesticidally effective amount of a compound of the formula (I) or a salt thereof as claimed in claim 1.

22. A method for controlling harmful organisms in transgenic crop plants comprising the step of directly or indirectly applying to the pest a pesticidally effective amount of a compound of the formula (I) as claimed in claim 1.

23. A veterinary medicament comprising a pesticidally effective amount of a compound of the formula (I) as claimed in claim 1 and one or more veterinarily acceptable formulation auxiliaries therefor.

24. A medicament against endo- and ectoparasites comprising an endo- or ectoparasiticidally effective amount of a compound of the formula (I) as claimed in claim 1 and one or more veterinarily acceptable formulation auxiliaries therefor.

25. A compound as claimed in claim 1, having the formula:

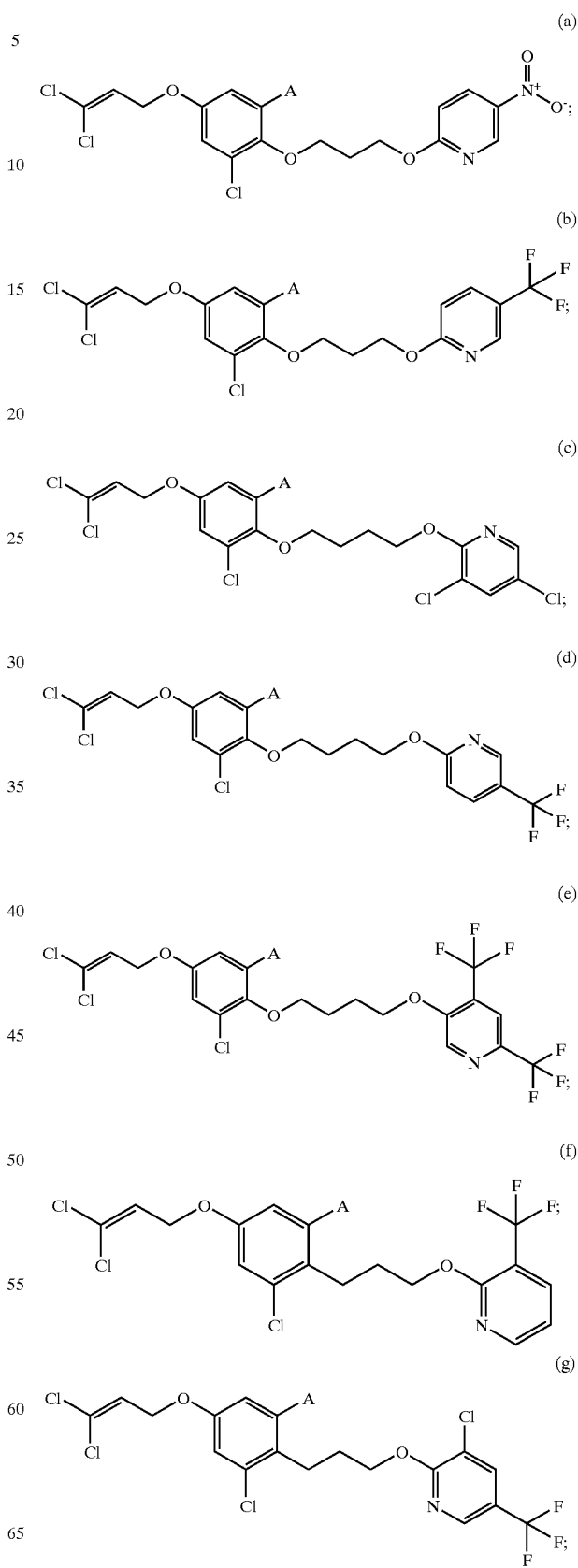

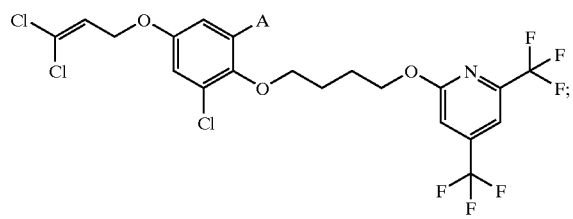 (h)
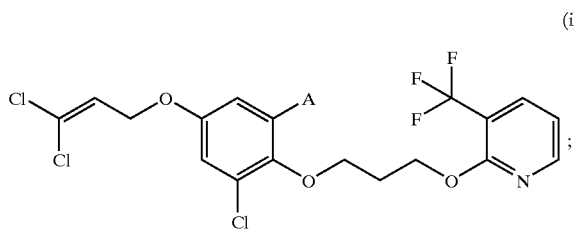 (i)
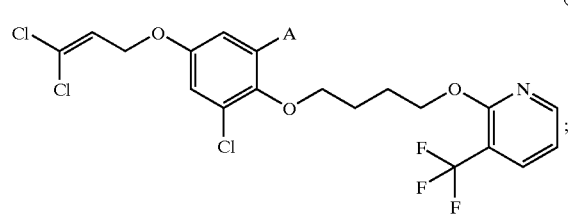 (j)
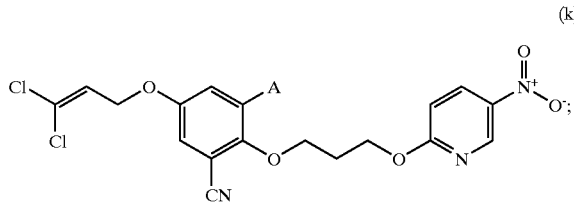 (k)
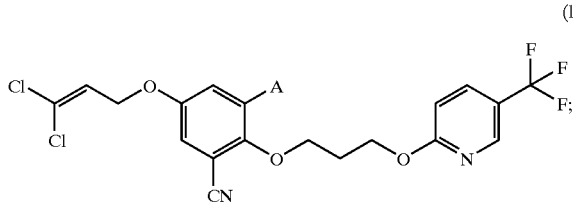 (l)
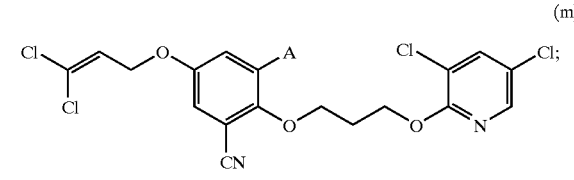 (m)
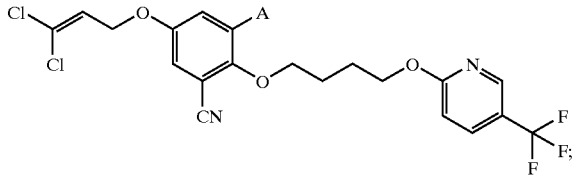 (n)
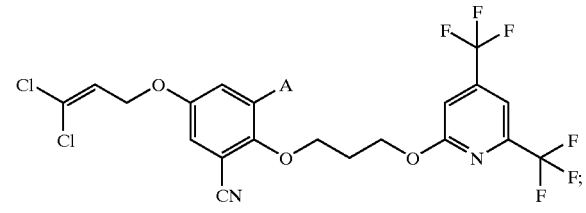 (o)
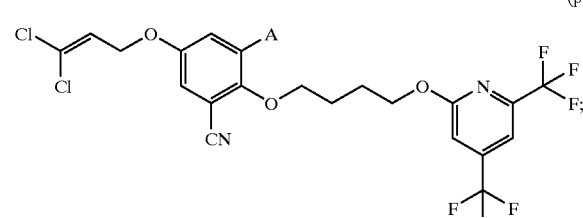 (p)
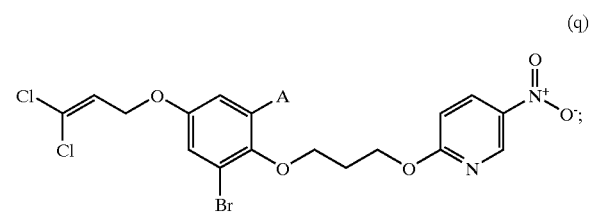 (q)
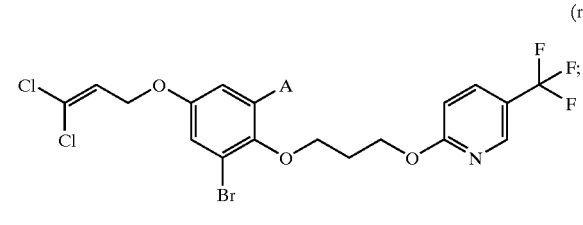 (r)
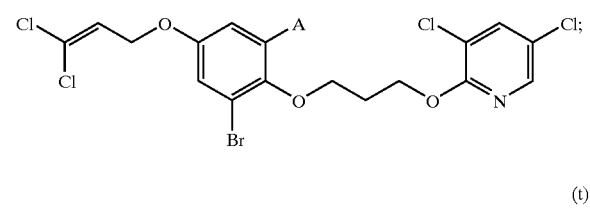 (s)
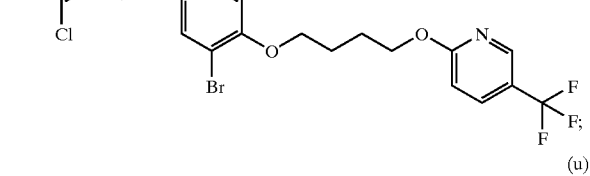 (t)
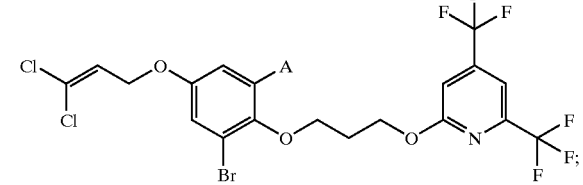 (u)

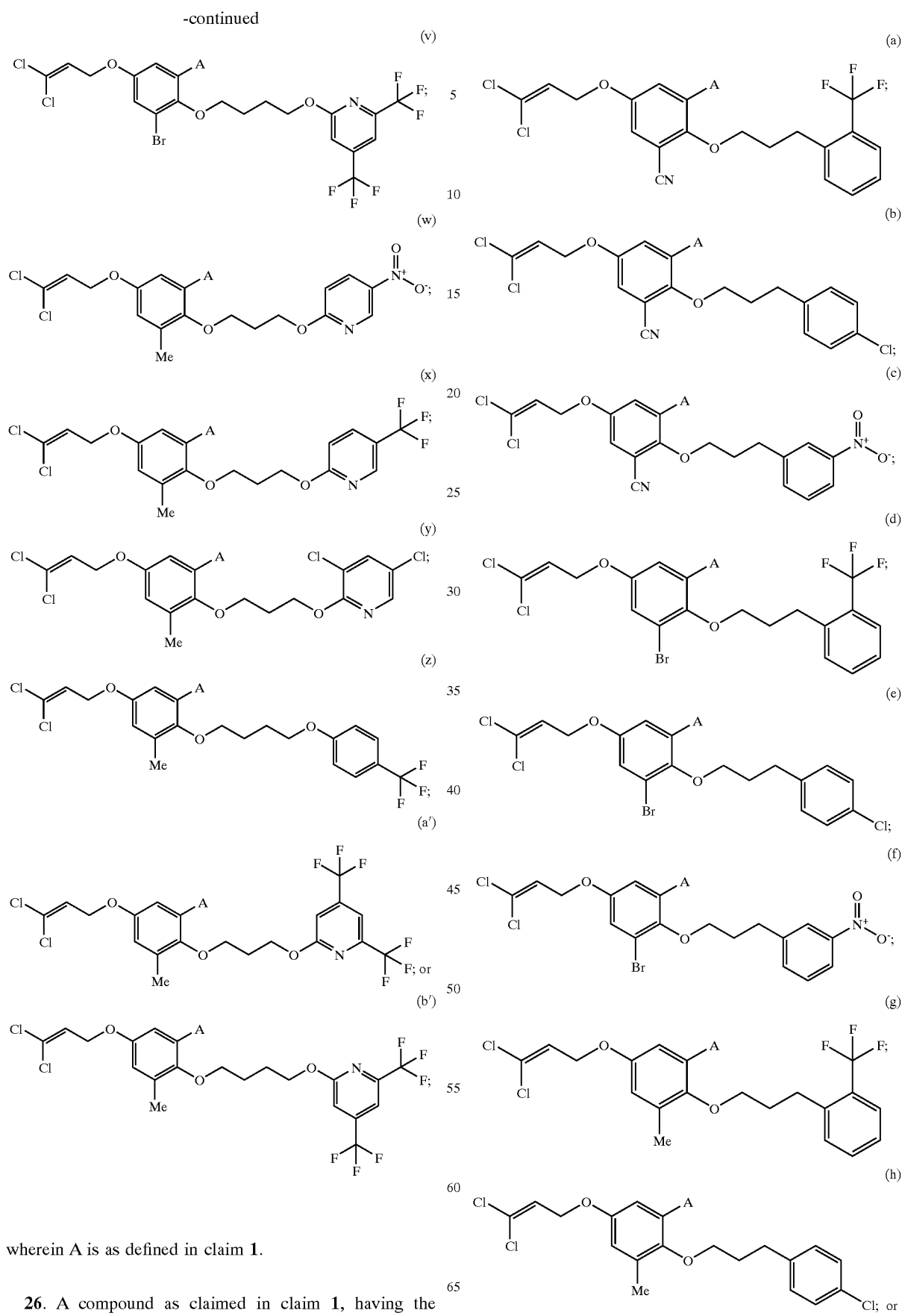
wherein A is as defined in claim 1.
26. A compound as claimed in claim 1, having the formula:

-continued
(i)
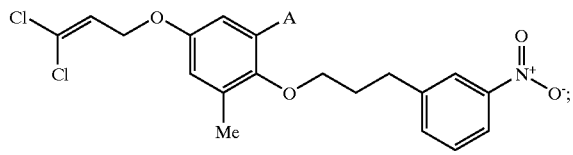
wherein A is as defined in claim 1.
27. A compound as claimed in claim 1, having the formula:
(a)
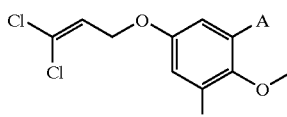
(b)
(c)
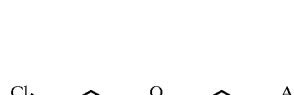
(d)
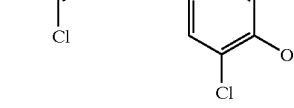
(e)
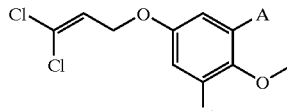
(f)
-continued
(g)
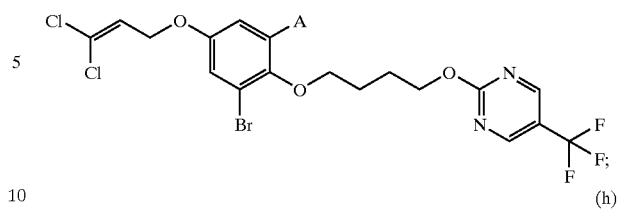
(h)
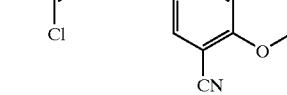
(i)
(j)
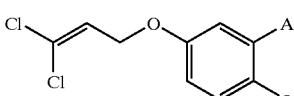
(k)
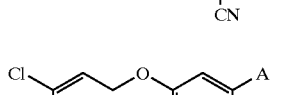
(l)
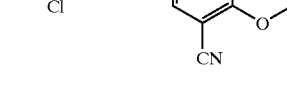
wherein A is as defined in claim 1.
28. A compound as claimed in claim 1, wherein A is
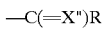
wherein
X″ is O and R is
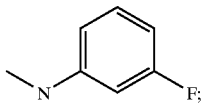

X" is O and R is

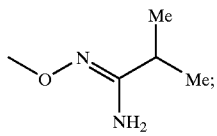

X" is O and R is

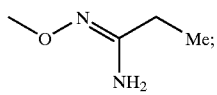

X" is O and R is

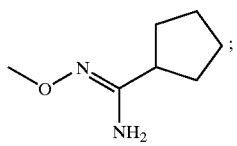

X" is O and R is

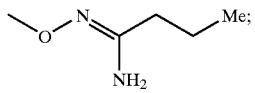

X" is O and R is

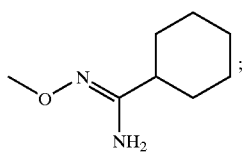

X" is O and R is 1-imidazolyl;
X" is O and R is CH=CH—NMe$_2$;
X" is O and R is CH$_2$CF$_3$;
X" is O and R is CH$_2$CH$_2$CH$_3$;
X" is O and R is CHBr$_2$;
X" is O and R is Et;
X" is O and R is H;
X" is O and R is Me;
X" is N—OH and R is Me;
X" is N—OMe and R is Me;
X" is O and R is NH$_2$;
X" is S and R is NH$_2$;
X" is O and R is NHCH(Me)CH$_2$OH;
X" is O and R is NHCH$_2$CH$_2$OH;
X" is O and R is NHEt;
X" is O and R is NHMe-OMe;
X" is O and R is NMe$_2$;
X" is O and R is O—CH(Me)$_2$;
X" is O and R is O—CH$_2$CH$_2$CH$_3$;
X" is O and R is OMe; or
X" is O and R is O-phenyl.

29. A compound as claimed in claim 28, wherein X" is O and R is Me, X" is N—OH and R is Me, X" is N—OMe and R is Me or X" is O and R is O-Me.

30. The compound having the formula:

(a)

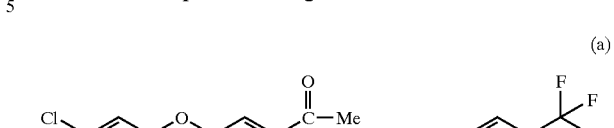

(b)

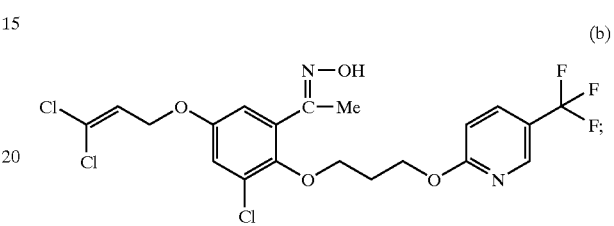

(c)

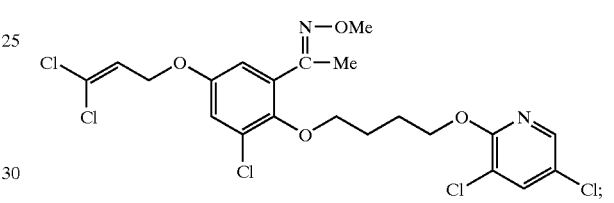

(d)

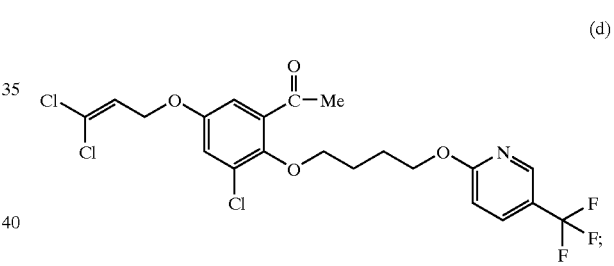

(e)

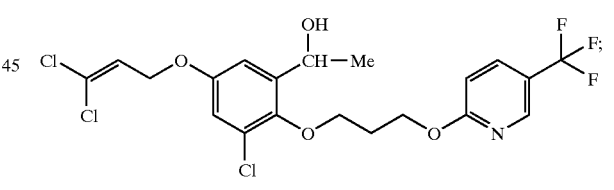

(f)

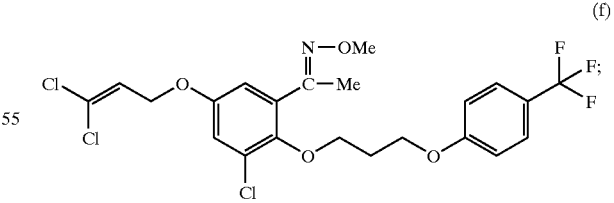

(g)

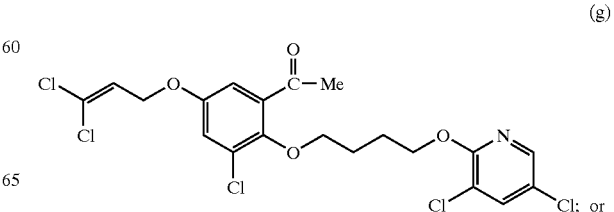

or (h)

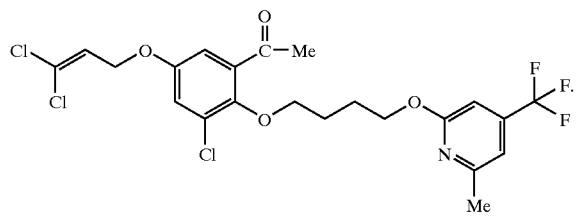

31. The compound according to claim 30, having the formula:

(a)

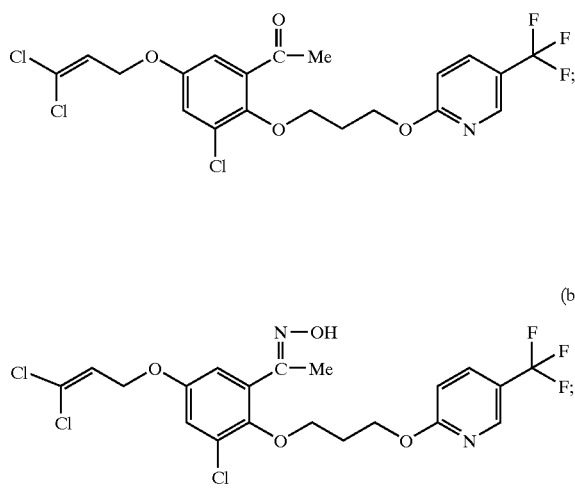

(b)

(c)

(d)

(e)

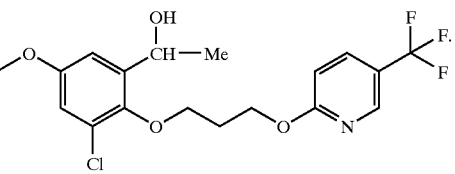

32. The compound according to claim 31, having the formula:

(a)

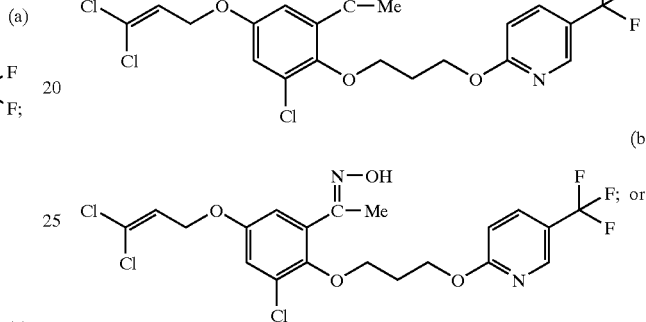

(b)

(c)

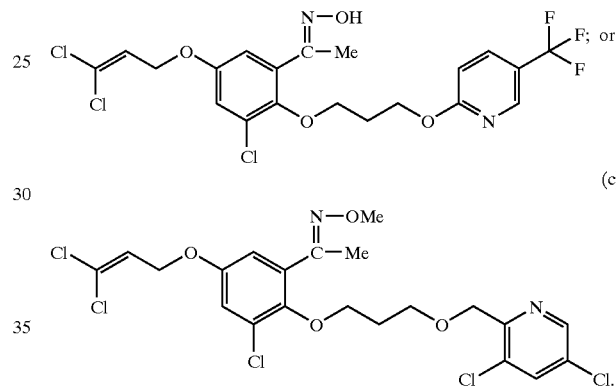

33. The compound according to claim 32, which has the formula:

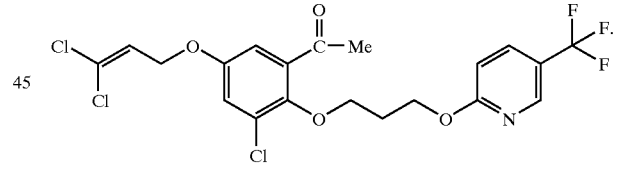

34. A compound as claimed in claim 1, wherein $R^6$, $R^7$, and $R^8$, independently of one another are hydrogen, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl, $C_4$–$C_{10}$-cycloalkynyl, phenyl, imidazolyl, oxadiazolyl, $\Delta^2$-oxazolinyl or pyrazolyl, wherein each of phenyl, imidazolyl, oxadiazolyl, $\Delta^2$-oxazolinyl and pyrazolyl is optionally substituted by halogen, hydroxyl, cyano, nitro, $C_1$–$C_8$-alkyl, $C_2$–$C_8$-alkenyl, $C_2$–$C_8$-alkynyl, $C_3$–$C_{10}$-cycloalkyl, $C_4$–$C_{10}$-cycloalkenyl or $C_4$–$C_{10}$-cycloalkynyl.

35. A compound as claimed in claim 13, wherein B is —(CH$_2$)$_2$—, —(CH$_2$)$_3$— or —(CH$_2$)$_4$—.

* * * * *